US006403360B1

(12) United States Patent
Blanar et al.

(10) Patent No.: US 6,403,360 B1
(45) Date of Patent: Jun. 11, 2002

(54) KCNQ POTASSIUM CHANNELS AND METHODS OF MODULATING SAME

(75) Inventors: Michael A. Blanar, Malvern; Paul C. Levesque, Yardley; Wayne A. Little, Pottstown, all of PA (US); Michael G. Neubauer, Skillman; Wen-Pin Yang, Princeton, both of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/105,058

(22) Filed: Jun. 26, 1998

Related U.S. Application Data

(60) Provisional application No. 60/055,599, filed on Aug. 12, 1997.

(51) Int. Cl.⁷ .......................... C12N 15/11; C12N 15/63; C12N 5/10
(52) U.S. Cl. ................. 435/243; 435/252.3; 435/320.1; 435/325; 536/23.5
(58) Field of Search ................. 435/69.1, 325, 435/320.1, 252.3, 243; 536/23.5, 23.1

(56) References Cited

FOREIGN PATENT DOCUMENTS

JP          9191882          7/1997

OTHER PUBLICATIONS

Yokoyama et al. (1996) DNA Research 3: 311–320.*
Barhanin et al. (1996) Nature 384:78–80.
Sanguinetti et al. (1996) Nature 384:80–83.
Yang et al. (1997) Proc. Natl. Acad. Sci. USA 94:4017–22.
Wang et al. (1996) Nature Genetics 12:17–23.
Wei et al. (1996) Neuropharmacology 35:805–29.
Halliwell (1990) Potassium Channels–Structure, Classification, Function and Therapeutic Potential (N.S. Cook, ed.) 384:381.
Pongs (1992) Physiol. Rev. 72:S69–S88.
Biervert et al. (1998) Science 279:403–406.
Charlier et al. (1998) Nature Genetics 18:53–55.
Singh et al. (1998) Nature Genetics 18:25–29.
Jan, L.Y. and Jan, Y.N. (1992) Ann. Rev. Physiol. 54:537–55.
Catterall (1995) Ann. Rev. Biochem. 64:493–531.
D82346 Homo sapiens mRNA for HNSPC, complete cds, Yokoyama et al., Sequence Submitted Dec. 21, 1995; Released to public: Feb. 14, 1997; National Center for Biotechnology Information (NCBI).

* cited by examiner

*Primary Examiner*—Michael Pak
(74) *Attorney, Agent, or Firm*—Briana C. Buchholz; Christopher A. Klein

(57) ABSTRACT

The present invention relates to KCNQ proteins defining potassium channels. In particular, the invention concerns the human KCNQ2, human KCNQ3, murine KCNQ2, and rat KCNQ2 proteins reported herein. KCNQ2 and KCNQ3 proteins are nervous system-selective and may be involved in neurotransmission and neuroprotection. The KCNQ2 and KCNQ3 of the present invention can be used to assay for modulators of the proteins, which would be useful in treatment of such disorders as ataxia, myokymia, seizures, Alzheimer's disease, Parkinson's disease, age-associated memory loss, learning deficiencies, motor neuron diseases, epilepsy, stroke, and the like.

11 Claims, 42 Drawing Sheets

```
CCCCCGCGCTCCGCCCCCGCTGAGCCTGAGCCCGACCCGGGGCGCCTCCCGCCAGGCACCATGGTGCAGAAGTCG
GGGGGCGCGAGGCGGGGGCGACTCGGACTCGGGCTGGGCCCCGCGGAGGGCGGTCCGTGGTACCACGTCTTCAGC
                                                        M  V  Q  K  S
                   100                                                    150
                    *                                                      *
CGCAACGGCGGCGTATACCCCGGCCCGAGCGGGGAGAAGAAGCTGAAGGTGGGCTTCGTGGGGCTGGACCCCGGC
GCGTTGCCGCCGCATATGGGGCCGGGCTCGCCCCTCTTCTTCGACTTCCACCCGAAGCACCCCGACCTGGGGCCG
 R  N  G  G  V  Y  P  G  P  S  G  E  K  K  L  K  V  G  F  V  G  L  D  P  G>

200
                           *
GCGCCCGACTCCACCCGGGACGGGGCGCTGCTGATCGCCGGCTCCGAGGCCCCCAAGCGCGGCAGCATCCTCAGC
CGCGGGCTGAGGTGGGCCCTGCCCCGCGACGACTAGCGGCCGAGGCTCCGGGGGTTCGCGCCGTCGTAGGAGTCG
 A  P  D  S  T  R  D  G  A  L  L  I  A  G  S  E  A  P  K  R  G  S  I  L  S 250                                                    300
                    *                                                      *
AAACCTCGCGCGGGCGGCGCGGGCGCCGGGAAGCCCCCCAAGCGCAACGCCTTCTACCGCAAGCTGCAGAATTTC
TTTGGAGCGCGCCCGCCGCGCCCGCGGCCCTTCGGGGGGTTCGCGTTGCGGAAGATGGCGTTCGACGTCTTAAAG
 K  P  R  A  G  G  A  G  A  G  K  P  P  K  R  N  A  F  Y  R  K  L  Q  N  F>

350
                           *
CTCTACAACGTGCTGGAGCGGCCGCGCGGCTGGGCGTTCATCTACCACGCCTACGTGTTCCTCCTGGTTTTCTCC
GAGATGTTGCACGACCTCGCCGGCGCGCCGACCCGCAAGTAGATGGTGCGGATGCACAAGGAGGACCAAAAGAGG
 L  Y  N  V  L  E  R  P  R  G  W  A  F  I  Y  H  A  Y  V  F  L  L  V  F  S 400                                                    450
                    *                                                      *
TGCCTCGTGCTGTCTGTGTTTTCCACCATCAAGGAGTATGAGAAGAGCTCGGAGGGGGCCCTCTACATCCTGGAA
ACGGAGCACGACAGACACAAAAGGTGGTAGTTCCTCATACTCTTCTCGAGCCTCCCCCGGGAGATGTAGGACCTT
 C  L  V  L  S  V  F  S  T  I  K  E  Y  E  K  S  S  E  G  A  L  Y  I  L  E>

500
                           *
ATCGTGACTATCGTGGTGTTTGGCGTGGAGTACTTCGTGCGGATCTGGGCCGCAGGCTGCTGCTGCCGGTACCGT
TAGCACTGATAGCACCACAAACCGCACCTCATGAAGCACGCCTAGACCCGGCGTCCGACGACGACGGCCATGGCA
 I  V  T  I  V  V  F  G  V  E  Y  F  V  R  I  W  A  A  G  C  C  C  R  Y  R 550                                                    600
                    *                                                      *
GGCTGGAGGGGGCGGCTCAAGTTTGCCCGGAAACCGTTCTGTGTGATTGACATCATGGTGCTCATCGCCTCCATT
CCGACCTCCCCCGCCGAGTTCAAACGGGCCTTTGGCAAGACACACTAACTGTAGTACCACGAGTAGCGGAGGTAA
 G  W  R  G  R  L  K  F  A  R  K  P  F  C  V  I  D  I  M  V  L  I  A  S  I>
```

FIG. 2A

```
                              650
GCGGTGCTGGCCGCCGGCTCCCAGGGCAACGTCTTTGCCACATCTGCGCTCCGGAGCCTGCGCTTCCTGCAGATT
CGCCACGACCGGCGGCCGAGGGTCCCGTTGCAGAAACGGTGTAGACGCGAGGCCTCGGACGCGAAGGACGTCTAA
 A  V  L  A  A  G  S  Q  G  N  V  F  A  T  S  A  L  R  S  L  R  F  L  Q  I 700                                                    750
CTGCGGATGATCCGCATGGACCGGCGGGGAGGCACCTGGAAGCTGCTGGGCTCTGTGGTCTATGCCCACAGCAAG
GACGCCTACTAGGCGTACCTGGCCGCCCCTCCGTGGACCTTCGACGACCCGAGACACCAGATACGGGTGTCGTTC
 L  R  M  I  R  M  D  R  R  G  G  T  W  K  L  L  G  S  V  V  Y  A  H  S  K>

800
GAGCTGGTCACTGCCTGGTACATCGGCTTCCTTTGTCTCATCCTGGCCTCGTTCCTGGTGTACTTGGCAGAGAAG
CTCGACCAGTGACGGACCATGTAGCCGAAGGAAACAGAGTAGGACCGGAGCAAGGACCACATGAACCGTCTCTTC
 E  L  V  T  A  W  Y  I  G  F  L  C  L  I  L  A  S  F  L  V  Y  L  A  E  K 850                                                    900
GGGGAGAACGACCACTTTGACACCTACGCGGATGCACTCTGGTGGGGCCTGATCACGCTGACCACCATTGGCTAC
CCCCTCTTGCTGGTGAAACTGTGGATGCGCCTACGTGAGACCACCCCGGACTAGTGCGACTGGTGGTAACCGATG
 G  E  N  D  H  F  D  T  Y  A  D  A  L  W  W  G  L  I  T  L  T  T  I  G  Y>

950
GGGGACAAGTACCCCCAGACCTGGAACGGCAGGCTCCTTGCGGCAACCTTCACCCTCATCGGTGTCTCCTTCTTC
CCCCTGTTCATGGGGGTCTGGACCTTGCCGTCCGAGGAACGCCGTTGGAAGTGGGAGTAGCCACAGAGGAAGAAG
 G  D  K  Y  P  Q  T  W  N  G  R  L  L  A  A  T  F  T  L  I  G  V  S  F  F 1000                                                   1050
GCGCTGCCTGCAGGCATCTTGGGGTCTGGGTTTGCCCTGAAGGTTCAGGAGCAGCACAGGCAGAAGCACTTTGAG
CGCGACGGACGTCCGTAGAACCCCAGACCCAAACGGGACTTCCAAGTCCTCGTCGTGTCCGTCTTCGTGAAACTC
 A  L  P  A  G  I  L  G  S  G  F  A  L  K  V  Q  E  Q  H  R  Q  K  H  F  E>

1100
AAGAGGCGGAACCCGGCAGCAGGCCTGATCCAGTCGGCCTGGAGATTTTACGCCACCAACCTCTCGCGCACAGAC
TTCTCCGCCTTGGGCCGTCGTCCGGACTAGGTCAGCCGGACCTCTAAAATGCGGTGGTTGGAGAGCGCGTGTCTG
 K  R  R  N  P  A  A  G  L  I  Q  S  A  W  R  F  Y  A  T  N  L  S  R  T  D 1150                                                   1200
CTGCACTCCACGTGGCAGTACTACGAGCGAACGGTCACCGTGCCCATGTACAGTTCGCAAACTCAAACCTACGGG
GACGTGAGGTGCACCGTCATGATGCTCGCTTGCCAGTGGCACGGGTACATGTCAAGCGTTTGAGTTTGGATGCCC
 L  H  S  T  W  Q  Y  Y  E  R  T  V  T  V  P  M  Y  S  S  Q  T  Q  T  Y  G>
```

FIG. 2B

```
                                    1250
GCCTCCAGACTTATCCCCCCGCTGAACCAGCTGGAGCTGCTGAGAAACCTCAAGAGTAAATCTGGACTCGCTTTC
CGGAGGTCTGAATAGGGGGGCGACTTGGTCGACCTCGACGACTCTTTGGAGTTCTCATTTAGACCTGAGCGAAAG
  A  S  R  L  I  P  P  L  N  Q  L  E  L  L  R  N  L  K  S  K  S  G  L  A  F 1300                                                              1350
AGGAAGGACCCCCCGCCGGAGCCGTCTCCAAGTAAAGGCAGCCCGTGCAGAGGGCCCCTGTGTGGATGCTGCCCC
TCCTTCCTGGGGGGCGGCCTCGGCAGAGGTTCATTTCCGTCGGGCACGTCTCCCGGGGACACACCTACGACGGGG
   R  K  D  P  P  P  E  P  S  P  S  K  G  S  P  C  R  G  P  L  C  G  C  C  P>

1400
GGACGCTCTAGCCAGAAGGTCAGTTTGAAAGATCGTGTCTTCTCCAGCCCCCGAGGCGTGGCTGCCAAGGGGAAG
CCTGCGAGATCGGTCTTCCAGTCAAACTTTCTAGCACAGAAGAGGTCGGGGGCTCCGCACCGACGGTTCCCCTTC
  G  R  S  S  Q  K  V  S  L  K  D  R  V  F  S  S  P  R  G  V  A  A  K  G  K 1450                                                              1500
GGGTCCCCGCAGGCCCAGACTGTGAGGCGGTCACCCAGCGCCGACCAGAGCCTCGAGGACAGCCCCAGCAAGGTG
CCCAGGGGCGTCCGGGTCTGACACTCCGCCAGTGGGTCGCGGCTGGTCTCGGAGCTCCTGTCGGGGTCGTTCCAC
  G  S  P  Q  A  Q  T  V  R  R  S  P  S  A  D  Q  S  L  E  D  S  P  S  K  V>

1550
CCCAAGAGCTGGAGCTTCGGGGACCGCAGCCGGGCACGCCAGGCTTTCCGCATCAAGGGTGCGGCGTCACGGCAG
GGGTTCTCGACCTCGAAGCCCCTGGCGTCGGCCCGTGCGGTCCGAAAGGCGTAGTTCCCACGCCGCAGTGCCGTC
  P  K  S  W  S  F  G  D  R  S  R  A  R  Q  A  F  R  I  K  G  A  A  S  R  Q 1600                                                              1650
AACTCAGAAGCAAGCCTCCCCGGAGAGGACATTGTGGATGACAAGAGCTGCCCCTGCGAGTTTGTGACCGAGGAC
TTGAGTCTTCGTTCGGAGGGGCCTCTCCTGTAACACCTACTGTTCTCGACGGGGACGCTCAAACACTGGCTCCTG
  N  S  E  A  S  L  P  G  E  D  I  V  D  D  K  S  C  P  C  E  F  V  T  E  D>
```

FIG. 2C

```
                                    1700
CTGACCCCGGGCCTCAAAGTCAGCATCAGAGCCGTGTGTGTCATGCGGTTCCTGGTGTCCAAGCGGAAGTTCAAG
GACTGGGGCCCGGAGTTTCAGTCGTAGTCTCGGCACACACAGTACGCCAAGGACCACAGGTTCGCCTTCAAGTTC
 L  T  P  G  L  K  V  S  I  R  A  V  C  V  M  R  F  L  V  S  K  R  K  F  K 1750                                                        1800
GAGAGCCTGCGGCCCTACGACGTGATGGACGTCATCGAGCAGTACTCAGCCGGCCACCTGGACATGCTGTCCCGA
CTCTCGGACGCCGGGATGCTGCACTACCTGCAGTAGCTCGTCATGAGTCGGCCGGTGGACCTGTACGACAGGGCT
 E  S  L  R  P  Y  D  V  M  D  V  I  E  Q  Y  S  A  G  H  L  D  M  L  S  R>

1850
ATTAAGAGCCTGCAGTCCAGAGTGGACCAGATCGTGGGGCGGGGCCCAGCGATCACGGACAAGGACCGCACCAAG
TAATTCTCGGACGTCAGGTCTCACCTGGTCTAGCACCCCGCCCCGGGTCGCTAGTGCCTGTTCCTGGCGTGGTTC
 I  K  S  L  Q  S  R  V  D  Q  I  V  G  R  G  P  A  I  T  D  K  D  R  T  K 1900                                                        1950
GGCCCGGCCGAGGCGGAGCTGCCCGAGGACCCCAGCATGATGGGACGGCTCGGGAAGGTGGAGAAGCAGGTCTTG
CCGGGCCGGCTCCGCCTCGACGGGCTCCTGGGGTCGTACTACCCTGCCGAGCCCTTCCACCTCTTCGTCCAGAAC
 G  P  A  E  A  E  L  P  E  D  P  S  M  M  G  R  L  G  K  V  E  K  Q  V  L>

2000
TCCATGGAGAAGAAGCTGGACTTCCTGGTGAATATCTACATGCAGCGGATGGGCATCCCCCCGACAGAGACCGAG
AGGTACCTCTTCTTCGACCTGAAGGACCACTTATAGATGTACGTCGCCTACCCGTAGGGGGGCTGTCTCTGGCTC
 S  M  E  K  K  L  D  F  L  V  N  I  Y  M  Q  R  M  G  I  P  P  T  E  T  E 2050                                                        2100
GCCTACTTTGGGGCCAAAGAGCCGGAGCCGGCGCCGCCGTACCACAGCCCGGAAGACAGCCGGGAGCATGTCGAC
CGGATGAAACCCCGGTTTCTCGGCCTCGGCCGCGGCGGCATGGTGTCGGGCCTTCTGTCGGCCCTCGTACAGCTG
 A  Y  F  G  A  K  E  P  E  P  A  P  P  Y  H  S  P  E  D  S  R  E  H  V  D>
```

FIG. 2D

```
                                        2150
AGGCACGGCTGCATTGTCAAGATCGTGCGCTCCAGCAGCTCCACGGGCCAGAAGAACTTCTCGGCGCCCCCGGCC
TCCGTGCCGACGTAACAGTTCTAGCACGCGAGGTCGTCGAGGTGCCCGGTCTTCTTGAAGAGCCGCGGGGGCCGG
  R  H  G  C  I  V  K  I  V  R  S  S  S  S  T  G  Q  K  N  F  S  A  P  P  A 2200                                                     2250
GCGCCCCCTGTCCAGTGTCCGCCCTCCACCTCCTGGCAGCCACAGAGCCACCCGCGCCAGGGCCACGGCACCTCC
CGCGGGGGACAGGTCACAGGCGGGAGGTGGAGGACCGTCGGTGTCTCGGTGGGCGCGGTCCCGGTGCCGTGGAGG
  A  P  P  V  Q  C  P  P  S  T  S  W  Q  P  Q  S  H  P  R  Q  G  H  G  T  S>

2300
CCCGTGGGGGACCACGGCTCCCTGGTGCGCATCCCGCCGCCCGCCTGCCCACGAGCGGTCGCTGTCCGCCTACGGC
GGGCACCCCCTGGTGCCGAGGGACCACGCGTAGGGCGGCGGCGGACGGGTGCTCGCCAGCGACAGGCGGATGCCG
  P  V  G  D  H  G  S  L  V  R  I  P  P  P  P  A  H  E  R  S  L  S  A  Y  G 2350                                                     2400
GGGGGCAACCGCGCCAGCATGGAGTTCCTGCGGCAGGAGGACACCCCGGGCTGCAGGCCCCCCGAGGGGACCCTG
CCCCCGTTGGCGCGGTCGTACCTCAAGGACGCCGTCCTCCTGTGGGGCCCGACGTCCGGGGGGCTCCCCTGGGAC
  G  G  N  R  A  S  M  E  F  L  R  Q  E  D  T  P  G  C  R  P  P  E  G  T  L>

2450
CGGGACAGCGACACGTCCATCTCCATCCCGTCCGTGGACCACGAGGAGCTGGAGCGTTCCTTCAGCGGCTTCAGC
GCCCTGTCGCTGTGCAGGTAGAGGTAGGGCAGGCACCTGGTGCTCCTCGACCTCGCAAGGAAGTCGCCGAAGTCG
  R  D  S  D  T  S  I  S  I  P  S  V  D  H  E  E  L  E  R  S  F  S  G  F  S 2500                                                     2550
ATCTCCCAGTCCAAGGAGAACCTGGATGCTCTCAACAGCTGCTACGCGGCCGTGGCGCCTTGTGCCAAAGTCAGG
TAGAGGGTCAGGTTCCTCTTGGACCTACGAGAGTTGTCGACGATGCGCCGGCACCGCGGAACACGGTTTCAGTCC
  I  S  Q  S  K  E  N  L  D  A  L  N  S  C  Y  A  A  V  A  P  C  A  K  V  R>

2600
CCCTACATTGCGGAGGGAGAGTCAGACACCGACTCCGACCTCTGTACCCCGTGCGGGCCCCCGCCACGCTCGGCC
GGGATGTAACGCCTCCCTCTCAGTCTGTGGCTGAGGCTGGAGACATGGGGCACGCCCGGGGGCGGTGCGAGCCGG
  P  Y  I  A  E  G  E  S  D  T  D  S  D  L  C  T  P  C  G  P  P  P  R  S  A 2650                                                     2700
ACCGGCGAGGGTCCCTTTGGTGACGTGGGCTGGGCCGGGCCCAGGAAGTGAGGCGGCGCTGGGCCAGTGGACCCG
TGGCCGCTCCCAGGGAAACCACTGCACCCGACCCGGCCCGGGTCCTTCACTCCGCCGCGACCCGGTCACCTGGGC
  T  G  E  G  P  F  G  D  V  G  W  A  G  P  R  K>
```

FIG. 2E

```
                                  2750
CCCGCGGCCCTCCTCAGCACGGTGCCTCCGAGGTTTTGAGGCGGGAACCCTTTGGGGCCCTTTTCTTACAGTAAC
GGGCGCCGGGAGGAGTCGTGCCACGGAGGCTCCAAAACTCCGCCCTTGGGAAACCCCGGGAAAAGAATGTCATTG
              2800                                                2850
TGAGTGTGGCGGGAAGGGTGGGCCCTGGAGGGGCCCATGTGGGCTGAAGGATGGGGGCTCCTGGCAGTGACCTTT
ACTCACACCGCCCTTCCCACCCGGGACCTCCCCGGGTACACCCGACTTCCTACCCCCGAGGACCGTCACTGGAAA
                                  2900
TACAAAAGTTATTTTCCAACAGGGGCTGGAGGGCTGGGCAGGGCCCTGTGGCTCCAGGAGCAGCGTGCAGGAGCA
ATGTTTTCAATAAAAGGTTGTCCCCGACCTCCCGACCCGTCCCGGGACACCGAGGTCCTCGTCGCACGTCCTCGT
              2950                                                3000
AGGCTGCCCTGTCCACTCTGCTCAGGGCCGCGGCCGACATCAGCCCGGTGTGAGGAGGGGCGGGAGTGATGACGG
TCCGACGGGACAGTTGAGACGAGTCCCGGCGCCGGCTGTAGTCGGGCCACACTCCTCCCCGCCCTCACTACTGCC
                                  3050
GGTGTTGCCAGCGTGGCAACAGGCGGGGGGTTGTTTCAGCCGAGCCCAGGGGAGGCACAAAGGGCAGGCCTGTTC
CCACAACGGTCGCACCGTTGTCCGCCCCCCAACAAAGTCGGCTCGGGTCCCCTCCGTGTTTCCCGTCCGGACAAG
              3100                                                3150
CCTGAGGACCTGCGCAAAGGGCGGGCCTGTTTGGTGAGGACCTGCGGCCTTGGGTCCCGGTGGGGTTTCCGGGCA
GGACTCCTGGACGCGTTTCCCGCCCGGACAAACCACTCCTGGACGCCGGAACCCAGGGCCACCCCAAAGGCCCGT
                                  3200
GCTACAGGCGGGTGTGGCCGGCCGCTGTGCGTGGCCTCTGCCTTCACACCTGACCTGCCCGGCGGGCTTTCCTGT
CGATGTCCGCCCACACCGGCCGGCGACACGCACCGGAGACGGAAGTGTGGACTGGACGGGCCGCCCGAAAGGACA
              3250
TCCCCACCTCAGGGGCGCCCAAATACAGAGCTATTGGTTGGCGTCTTAAAAAAAAAAAAAAAA
AGGGGTGGAGTCCCCGCGGGTTTATGTCTCGATAACCAACCGCAGAATTTTTTTTTTTTTTTT
```

FIG. 2F

```
KVLQT1                                                           MAAASSPPRAERKRWGWGRLPGARRGSAGLAKKCPFSLELAEGGPAGGALYAPIA    55
KVLR1                                                                            MVQKSRNGGVYPGPSGEKKLKVGFVGLD    28

S1
KVLQT1    PGAPGPAPPAS--PAAPAAPPVASDLGPRPPVSLDPRVSIYSTRRPVLARTHVQGRVYNFLERPTGWKCFVYHFAVF   130
KVLR1     PGAPDSTRDGALLIAGSEAPKRGSIL-SKPRAG-GAGAGK--PPKRNAFYR-KLQNFLYNVLERPRGWA-FIYHAYVF    100

S1                              S2                                     S3
KVLQT1    LIVLVCLIFSVLSTIEQYAALATGTLFWMEIVLVVFFGTEYVVRLWSAGCRSKYVGLWGRLRFARKPISIIDLIVVV   207
KVLR1     LLVFSCLVLSVFSTIKEYEKSSEGALYILEIVTIVVFGVEYFVRIWAAGCCCRYRGRLKFARKPFCVIDIMVLI     177

S4                                          Pore                          S5
KVLQT1    ASMVVTLCVGSKGQVFATSAIRGIRFLQILRMLHVDRQGGTWRLLGSVVFIHRQELITTLYIGFLGLIFSSYFVVLAE   284
KVLR1     ASIAVLAAGSQGNVFATSALRFLQILRMIRMDRRGGTWKLLGSVVYAHSKELVTAWYIGFLCLILASFLVYLAE       254

S6
KVLQT1    KDAVNESGRVEFGSYADALWWGVVTVTTIGYGDKVPQTWVGKTIASCFSVFAISFFALPAGILGSGFALKVQQKQRQ   361
KVLR1     K---GENDH--FDTYADALWWGLITLTTIGYGDKYPQTWNGRLLAATFTLIGVSFFALPAGILGSGFALKVQEQHRQ    326

KVLQT1    KHFNRQIPAAASLIQTAWRCYAAE--NPD-SSTWKIYIRKAPRSHTLLSPSPKPKKSVVVKKKKFKLDKDNG//     430
KVLR1     KHFEKRRNPAAGLIQSAWRFYATNLSRTDLHSTWQYYERTVTVPMYS-SQTQTYGASRLIPPLNQLELLRNL//     398
```

FIG. 3

| | | |
|---|---|---|
| KvLQT1 | MAAASSPPPRAERKRWGWGRLPGARRGSAGLAKKCPFSLELAEGGPAGGALYAPIA | 55 |
| KvLR2 | PAGGDAAAAGDEERKVGLAPGDVEQVTLA | 29 |
| KvLQT1 | PGAPGPAPPAS--PAAPAAPPVASDLGPRPPVSLDPRVSIYSTRRPVLARTHVQGRVYNFLERPTGWKCFVYHFAVF | 130 |
| KvLR2 | LGA-GADKDGTLLEGGRDEGQRRTPQGIGLLAKTPLSRPVKRNNAKYR-RIQTLIYDALERPRGWALL-YHALVF | 103 |

S1                                                                                  S2                                                         S3

| | | |
|---|---|---|
| KvLQT1 | LIVLVCLIFSVLSTIEQYAALATGTLFWMEIVLVVFFGTEYVVRLWSAGCRSKYVGLWGRLRFARKPISIIDLIVVV | 207 |
| KvLR2 | LIVLGCLILAVLTTFKEYETVSGDWLLLLETFAIFIFGAEFALRIWAAGCCCRYKGWRGRLKFARKPLCMLDIFVLI | 180 |

S4                                                             S5

| | | |
|---|---|---|
| KvLQT1 | ASMVVLCVGSKGQVFATSAIRGIRFLQIILRMLFVDRQGGTWRLLGSVVFIHRQELITTLYIGFLGLIFSSYFVYLAE | 284 |
| KvLR2 | ASVPVVAVGNQGNVLATSL--RSLRFLQILRMLRMDRGGTWKLLGSAICAHSKELITAWYIGFLTLILSSFLVLVE | 256 |

Pore                                                S6

| | | |
|---|---|---|
| KvLQT1 | KD-----AVNESGRVEFGSYADALWWGVVTVTTIGYGDKVPQTWVGKTIASCFSVFAISFFALPAGILGSGFALKVQ | 356 |
| KvLR2 | KDVPEVDAQGEEMKEFETYADALWWGLITLATIGYGDKTPKTWEGRLIAATFSLIGVSFFALPAGILGSGLALKVQ | 333 |

| | | |
|---|---|---|
| KvLQT1 | QKQRQKHFN-RQIPAAASLIQTAWRCYAAENPDSSTW// | 392 |
| KvLR2 | EQHRQKHFEKRRKPAAE-LIQAAWRYYAT-NPNRIDLVGDM// | 372 |

FIG. 4

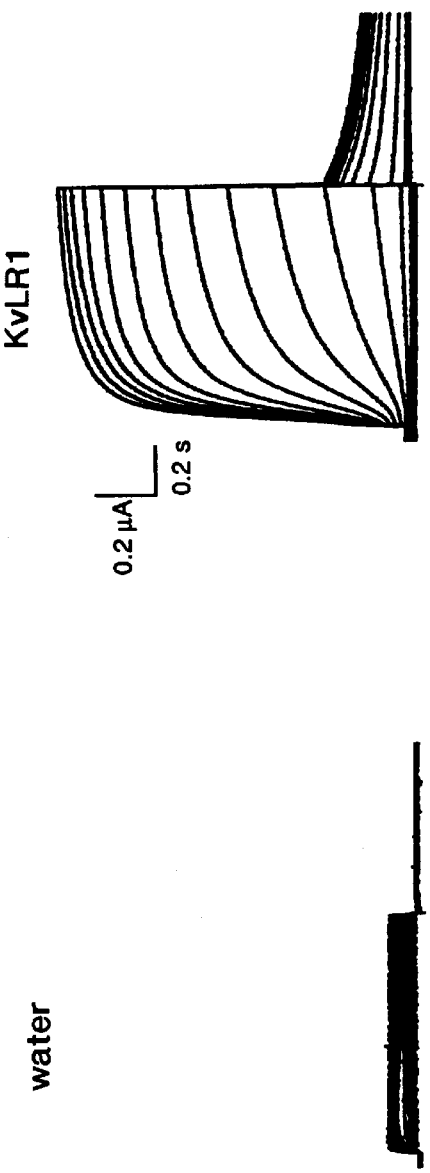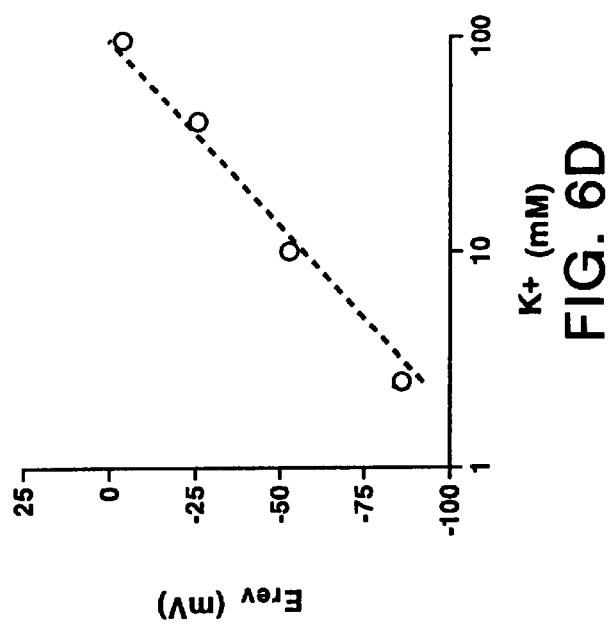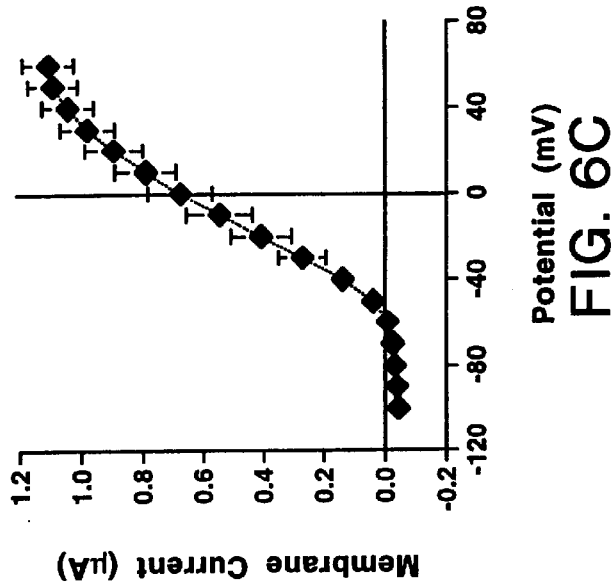

```
                                                   30                        60                        90
                                                    *                         *                         *
GAGCAGCACAGGCAGAGAAACACTTTGAGAAAACGGGCGGAACCCTGCGCCTGGAGATTCTATGCTACTAACCTC
CTCGTCGTGTCCGTCTTTGTGAAACTCTTTGCCGCCTTGGGACGCCGTCCAGACTAGGTCAGACGGACCTCGAAGATACGATGATTGGAG
 E  Q  H  R  Q  K  H  F  E  K  R  R  N  P  A  A  G  L  I  Q  S  A  W  R  F  Y  A  T  N  L>
                                                  120                       150                       180
                                                    *                         *                         *
TTACGCACCGACCTGCACTCCACGTGGCAGTACTACGAGCGGACAGTCACTGTCCCCATGTACAGCTCACAAACTCAAACCTATGGGCC
AATGCGTGGCTGGACGTGAGGTGCACCGTCATGATGCTCGCCTGTCAGTCAGAGTTCGAGTGTTGAGTTTGAGTTTGGATACCCCGG
 L  R  T  D  L  H  S  T  W  Q  Y  Y  E  R  T  V  T  V  P  M  Y  S  S  Q  T  Q  T  Y  G  A>
                                                  210
                                                    *
TCCAGAGACTCATCCCACCTCTGAACCAGCTGGAGCTGCTGAGAAACA
AGGTCTGAGTAGGGTGGAGACTTGGTCGACCTCGACGACTCTTTGT
 S  R  L  I  P  P  L  N  Q  L  E  L  L  R  N>
```

FIG. 9C

```
ATG GTG CAG AAG TCG CGC AAC GGT GGC GTG TAC CCC GGC ACC AGC  45
 M   V   Q   K   S   R   N   G   G   V   Y   P   G   T   S
             5                       10                  15

GGG GAA AAG AAG CTC AAG GTG GGC TTC GTG GGG CTG GAC CCC GGC  90
 G   E   K   K   L   K   V   G   F   V   G   L   D   P   G
            20                       25                  30

GCG CCC GAC TCC ACA CGC GAC GGC GCG CTA CTC ATC GCG GGC TCC 135
 A   P   D   S   T   R   D   G   A   L   L   I   A   G   S
            35                       40                  45

GAG GCC CCC AAG CGC GGC AGC GTT TTG AGC AAG CCG CGG ACG GGC 180
 E   A   P   K   R   G   S   V   L   S   K   P   R   T   G
            50                       55                  60

GGC GCG GGA GCC GGG AAG CCC CCG AAG CGC AAC GCC TTC TAC CGC 225
 G   A   G   A   G   K   P   P   K   R   N   A   F   Y   R
            65                       70                  75

AAG CTG CAG AAT TTC CTC TAC AAC GTG CTA GAG CGG CCC CGC GGC 270
 K   L   Q   N   F   L   Y   N   V   L   E   R   P   R   G
            80                       85                  90

TGG GCG TTC ATC TAC CAC GCC TAC GTG TTC CTT TTA GTC TTC TCC 315
 W   A   F   I   Y   H   A   Y   V   F   L   L   V   F   S
            95                      100                 105

TGC CTT GTG CTT TCT GTG TTT TCC ACC ATC AAG GAG TAC GAG AAG 360
 C   L   V   L   S   V   F   S   T   I   K   E   Y   E   K
           110                      115                 120

AGC TCT GAG GGG GCC CTC TAC ATC TTG GAA ATC GTG ACT ATC GTG 405
 S   S   E   G   A   L   Y   I   L   E   I   V   T   I   V
           125                      130                 135

GTA TTC GGT GTT GAG TAC TTT GTG AGG ATC TGG GCT GCA GGC TGC 450
 V   F   G   V   E   Y   F   V   R   I   W   A   A   G   C
           140                      145                 150

TGT TGC CGG TAT CGA GGC TGG AGG GGC AGG CTC AAG TTT GCC AGG 495
 C   C   R   Y   R   G   W   R   G   R   L   K   F   A   R
           155                      160                 165

AAG CCG TTC TGT GTG ATT GAT ATC ATG GTG CTG ATT GCC TCC ATT 540
 K   P   F   C   V   I   D   I   M   V   L   I   A   S   I
           170                      175                 180

GCT GTG CTG GCT GCT GGT TCC CAG GGC AAT GTC TTT GCC ACA TCT 585
 A   V   L   A   A   G   S   Q   G   N   V   F   A   T   S
           185                      190                 195
```

FIG. 10A

```
GCG CTT CGG AGC TTG CGG TTC TTG CAA ATC TTG CGG ATG ATC CGT   630
 A   L   R   S   L   R   F   L   Q   I   L   R   M   I   R
             200                 205                 210

ATG GAC CGG AGG GGT GGC ACC TGG AAG CTC TTG GGA TCG GTA GTC   675
 M   D   R   R   G   G   T   W   K   L   L   G   S   V   V
             215                 220                 225

TAC GCT CAC AGC AAG GAG CTG GTG ACT GCC TGG TAC ATT GGC TTC   720
 Y   A   H   S   K   E   L   V   T   A   W   Y   I   G   F
             230                 235                 240

CTC TGC CTC ATC CTG GCC TCA TTT CTG GTG TAC TTG GCA GAA AAG   765
 L   C   L   I   L   A   S   F   L   V   Y   L   A   E   K
             245                 250                 255

GGT GAG AAT GAC CAC TTT GAC ACC TAC GCA GAT GCA CTC TGG TGG   810
 G   E   N   D   H   F   D   T   Y   A   D   A   L   W   W
             260                 265                 270

GGT CTG ATC ACC CTG ACG ACC ATT GGC TAC GGG GAC AAG TAC CCT   855
 G   L   I   T   L   T   T   I   G   Y   G   D   K   Y   P
             275                 280                 285

CAG ACC TGG AAC GGG AGG CTG CTG GCA GCG ACC TTT ACC CTC ATT   900
 Q   T   W   N   G   R   L   L   A   A   T   F   T   L   I
             290                 295                 300

GGT GTC TCG TTC TTT GCT CTT CCT GCT GGC ATT TTG GGA TCC GGC   945
 G   V   S   F   F   A   L   P   A   G   I   L   G   S   G
             305                 310                 315

TTT GCC CTG AAA GTC CAA GAG CAG CAT CGG CAA AAA CAC TTT GAG   990
 F   A   L   K   V   Q   E   Q   H   R   Q   K   H   F   E
             320                 325                 330

AAA CGG CGG AAC CCT GCG GCA GGT CTG ATC CAG TCT GCC TGG AGA  1035
 K   R   R   N   P   A   A   G   L   I   Q   S   A   W   R
             335                 340                 345

TTC TAT GCT ACT AAC CTC TCA CGC ACC GAC CTG CAC TCC ACG TGG  1080
 F   Y   A   T   N   L   S   R   T   D   L   H   S   T   W
             350                 355                 360

CAG TAC TAC GAG CGG ACA GTC ACT GTC CCC ATG TAC AGA CTC ATC  1125
 Q   Y   Y   E   R   T   V   T   V   P   M   Y   R   L   I
             365                 370                 375

CCA CCT CTG AAC CAG CTG GAG CTG CTG AGG AAT CTC AAG AGC AAA  1170
 P   P   L   N   Q   L   E   L   L   R   N   L   K   S   K
             380                 385                 390
```

FIG. 10B

```
TCT GGA CTC ACC TTC AGG AAG GAG CCA CAG CCA GAG CCA TCA CCA  1215
 S   G   L   T   F   R   K   E   P   Q   P   E   P   S   P
             395                 400                 405

AGT CAG AAG GTC AGT TTG AAA GAT CGT GTC TTC TCC AGC CCC CGA  1260
 S   Q   K   V   S   L   K   D   R   V   F   S   S   P   R
             410                 415                 420

GGC ATG GCT GCC AAG GGA AAG GGG TCT CCC CAG GCC CAG ACG GTC  1305
 G   M   A   A   K   G   K   G   S   P   Q   A   Q   T   V
             425                 430                 435

CGG CGG TCC CCC AGT GCG GAT CAG AGT CTT GAT GAC AGC CCG AGC  1350
 R   R   S   P   S   A   D   Q   S   L   D   D   S   P   S
             440                 445                 450

AAG GTG CCC AAG AGC TGG AGC TTT GGT GAC CGC AGC CGC ACA CGC  1395
 K   V   P   K   S   W   S   F   G   D   R   S   R   T   R
             455                 460                 465

CAG GCT TTC CGC ATC AAG GGT GCT GCA TCC CGG CAG AAT TCA GAA  1440
 Q   A   F   R   I   K   G   A   A   S   R   Q   N   S   E
             470                 475                 480

GCA AGC CTC CCT GGG GAG GAC ATC GTA GAG GAC AAC AAG AGC TGT  1485
 A   S   L   P   G   E   D   I   V   E   D   N   K   S   C
             485                 490                 495

AAC TGC GAG TTT GTG ACT GAA GAT CTT ACC CCT GGC CTC AAA GTT  1530
 N   C   E   F   V   T   E   D   L   T   P   G   L   K   V
             500                 505                 510

AGC ATC AGA GCT GTG TGT GTT ATG CGG TTC TTG GTA TCT AAG CGA  1575
 S   I   R   A   V   C   V   M   R   F   L   V   S   K   R
             515                 520                 525

AAG TTC AAA GAG AGT CTG CGC CCA TAT GAT GTG ATG GAC GTC ATC  1620
 K   F   K   E   S   L   R   P   Y   D   V   M   D   V   I
             530                 535                 540

GAA CAG TAC TCG GCT GGA CAC TTG GAT ATG TTG TCC CGC ATC AAG  1665
 E   Q   Y   S   A   G   H   L   D   M   L   S   R   I   K
             545                 550                 555

AGC CTG CAG TCC AGA GTG GAC CAG ATT GTG GGG CGG GGC CCA ACA  1710
 S   L   Q   S   R   V   D   Q   I   V   G   R   G   P   T
             560                 565                 570

ATA ACG GAT AAG GAT CGC ACC AAA GGC CCA GCG GAA ACG GAG CTG  1755
 I   T   D   K   D   R   T   K   G   P   A   E   T   E   L
             575                 580                 585
```

FIG. 10C

```
CCC GAA GAC CCC AGC ATG ATG GGA CGG CTT GGG AAG GTG GAG AAA  1800
 P   E   D   P   S   M   M   G   R   L   G   K   V   E   K
            590                 595                 600

CAG GTC TTG TCC ATG GAA AAG AAG CTC GAC TTC TTG GTG AGC ATC  1845
 Q   V   L   S   M   E   K   K   L   D   F   L   V   S   I
            605                 610                 615

TAT ACA CAG AGA ATG GGC ATC CCA CCA GCA GAG ACA GAG GCC TAT  1890
 Y   T   Q   R   M   G   I   P   P   A   E   T   E   A   Y
            620                 625                 630

TTT GGG GCC AAG GAG CCT GAG CCG GCA CCA CCC TAC CAC AGC CCA  1935
 F   G   A   K   E   P   E   P   A   P   P   Y   H   S   P
            635                 640                 645

GAG GAC AGC CGT GAC CAT GCA GAC AAG CAT GGC TGT ATC ATT AAG  1980
 E   D   S   R   D   H   A   D   K   H   G   C   I   I   K
            650                 655                 660

ATC GTC CGC TCC ACC AGC TCT ACG GGC CAG AGG AAC TAC GCA GCA  2025
 I   V   R   S   T   S   S   T   G   Q   R   N   Y   A   A
            665                 670                 675

CCC CCA GCC ATC CCC CCT GCC CAG TGT CCT CCC TCC ACC TCG TGG  2070
 P   P   A   I   P   P   A   Q   C   P   P   S   T   S   W
            680                 685                 690

CAG CAG AGC CAC CAG CGC CAT GGC ACC TCC CCT GTG GGA GAC CAT  2115
 Q   Q   S   H   Q   R   H   G   T   S   P   V   G   D   H
            695                 700                 705

GGC TCA CTG GTC CTG CGA CTG GAG AGG AGT GCT GGC ATG ATG AGC  2160
 G   S   L   V   L   R   L   E   R   S   A   G   M   M   S
            710                 715                 720

TGT CAC TAG                                                   2169
 C   H   *
```

FIG. 10D

```
brainKvLQT-R    1   MVQKSRNGGVYPGTSGEKKLKVGFVGLDPGAPDSTRDGALLIAGSEAPKRGSVLSKPRTG
heartKvLQT      1   M----STPVSPAPAPADLGPRPRVSLDPRV-----------------SIYSARRPLLARTHIQ 61   GAGAGKPPKRNAFYRKLQNFLYNVLERPRGWA-FIYHAYFLLVESCLVLSVFSTIKEYE
               43   GR---------------VYNFLERPTGWKCEVYHFTVFLIVLVCLIFSVLSTIEQYA
                                                                              S1

120   KSSEGALYILEIVTIIVFGGVEFVRIWAAGCCCRYRGLRKFECVIDIMVLIAS
               85   ALATGTLFWMEIVLVVFFGTEYVVRLWSAGCRSKYVGIWGRLREARKPISILDLIVVVAS
                                  S2                                          S3

180   IAVLAAGSQGNVFATSALRSLRFLQILRMIRMDRRGGTWKLLGSVVYAHSKELVTAWYIG
              145   MVVLCVGSKGQVFATSAIRGIRFLQILRMLHVDRQGGTWRLLGSVVFIHRQELITLYIG
                                                      S4

240   FLCLILASFLVYLAEKGENDH------EDTYADALWWGLITLTTIGYGDKYPQTWNGRLLA
              205   FLGLIFSSYFVVLAEKDAVNESGRIEFGSYADALWWGVVTTTTIGYGDKVPQTWVGKTIA
                                      S5                    Pore 295   ATFTLIGVSFFALPAGILGSGFAIKVQEQHRQKHFEKRRNPAAGLIQSAWRFYATNLSRT
              265   SCFAISFFALPAGILGSGFALKVQQKQRQKHENRQIPAAASLIQTAWRCYAAENPDS
                                S6

355   DLHSTWQYERTVTVPMYRLIPPLNQLELLRNLKSKSGLTERKEPQPEPSPSQKVSLKDR
              325   ----ATWKIYVRKPARSHTLLSPSPKPKKSVMVKKKK---EKLDKDNGMSPGEKM-----

415   VFSSPRGMAAKGKGSPQAQTVRRSPSADQSLDDSPSKVPKSWSFGDRSRTRQAFRIKGAA
              373   -ENVPH-----ITYDPPEDRRPDHFSIDGYDSSVRKSPTLLELS------ITPHFLRTNSFA

475   SRQNSEASLPGEDIVEDNKSCNCEFVTEDLTPGLKVSIRAVCVMRFLVSKRKFKESLRPY
              422   ----EDLDLEGETLLTPITH-----VSQLRDHHRATHKVIRRMQYFVAKKKFQQARKPY

535   DVMDVIEQYSAGHLLDMLSRIKSLQSRVDQIVGRGP---THTDKDRTKGPAETELPEDPSM
              472   DVRDVIEQYSQGHLNLMVRIKELQRRLDQSIGKPSLFIPHSEKSKDRGSNTIG-----

592   MGRIGKVEKQVLSMEKKLDFLVSIYTQRMGIPPAETEAYFGAKEPEPAPPYHSPEDSRDH
              525   -ARLNRVEDKVTQLDQRLVIITDMLHQLLSM-----------------------Q

652   ADKHGCIIKIVRSTSSTGQRNYAAPPATPPAQCPPSTWQQSHQRHGTSPVGDHGSLVLR
              556   QGGPTCNSRSQVVASNEGG------SHNPELFLPSNSLPTYEQLTVPQTGPDEGS----

712   LERSAGMMSCH
              605   ---------S
```

FIG. 11

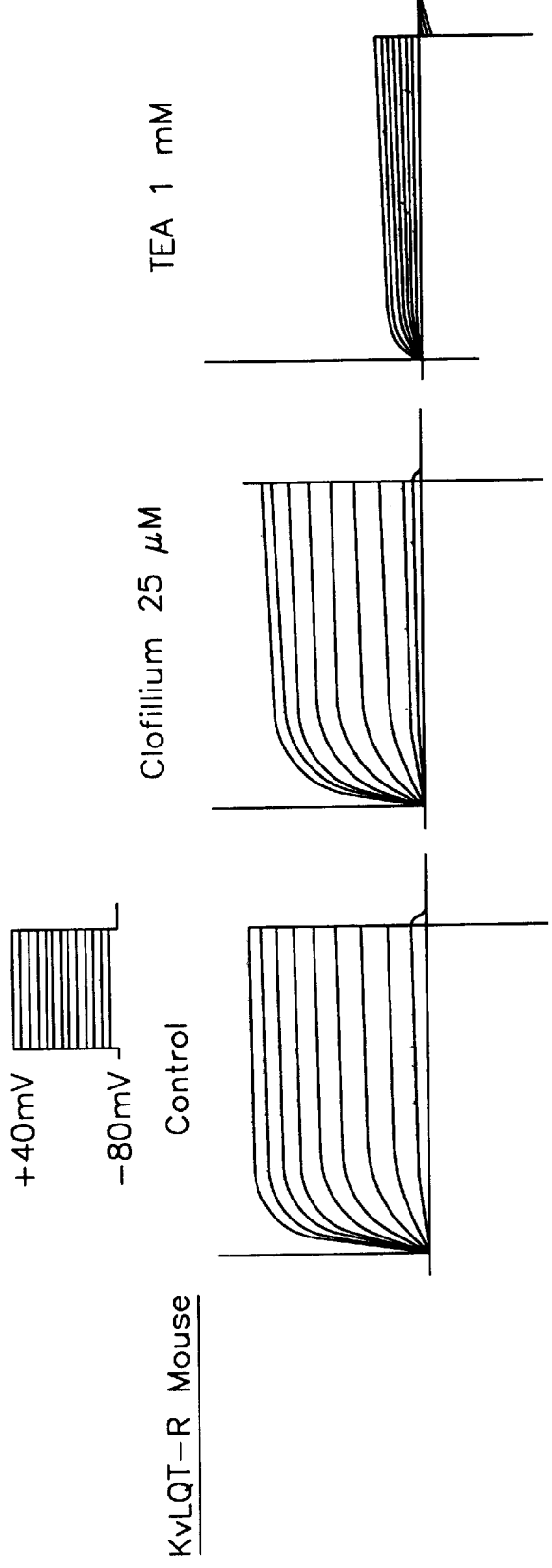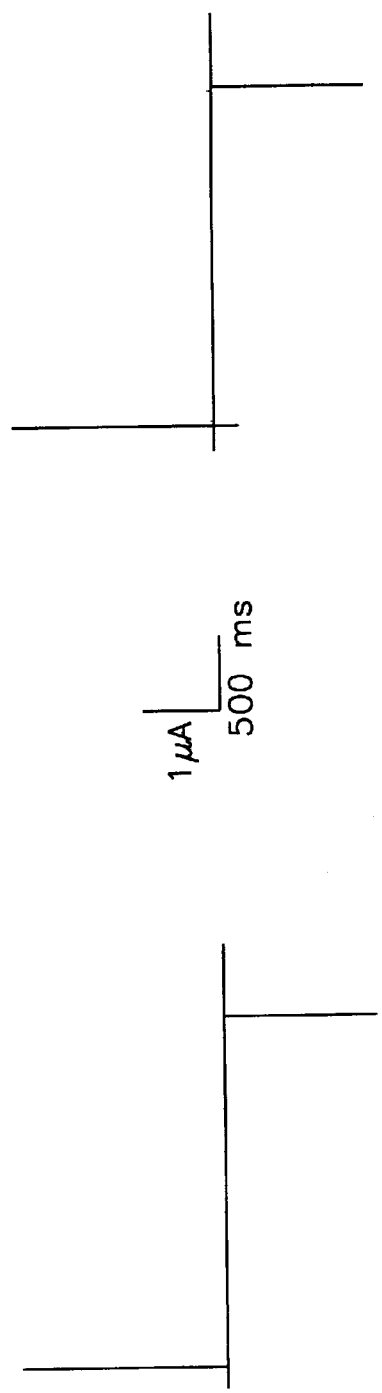

```
Consensus  AACC-C----G-A--GACCTG-----C-----G
  hKvLR2   AACCCCAACAGGATTGACCTGGTTGGCGACATG
           ||||| |   ||  | ||||||     |     |
  hKvLR1   AACCTCTCGCGCACAGACCTGCACTCCACGTGG
           ||||||||| |||| ||||||||||||||||||
  mKvLR1   AACCTCTCACGCACCGACCTGCACTCCACGTGG
           |||||||||||||||||||||||||||||||||
  rKvLR1   AACCTCTCACGCACCGACCTGCACTCCACGTGG
```

FIG. 16D

```
                                                          S1                                         S2
Consensus   ------P-KRN*A-YR---Q---Y---LERPRGWA---YHA-VFL-V--CL-L-V--T-KEYE---S--L-LE---I--FG-
hKvLR2      KTPLSRPVKRNMAKYRRIQTLIYDALERPRGWALLYHALVFLLIVLGCLLLAVLTTFKEYETVSGDWLLLLETFAIFIFGA
hKvLR1      GAGAGKPPKRN*AFYRKLQNFLYNVLERPRGWAFIYHAYVFLLVFSCLVLSVFSTIKEYEKSSEGALYILEIVTIVVFGV
mKvLR1      GAGAGKPPKRN*AFYRKLQNFLYNVLERPRGWAFIYHAYVFLLVFSCLVLSVFSTIKEYEKSSEGALYILEIVTIVVFGV
rKvLR1                                                              KEYEKSSEGALYILEIVTIVVFGV S3                                S4
Consensus   E---RIWAAGCCCRY-GWRGRLKFARKP-C---DI-VLIAS--V-A-G-QGNV-ATS*LRSLRFLQILRM-RMDRRGGTWKLL
hKvLR2      EFALRIWAAGCCCRYKGWRGRLKFARKPLCMLDIFVLIASVPVVAVGNQGNVLATS*LRSLRFLQILRMLRMDRRGGTWKLL
hKvLR1      EYFVRIWAAGCCCRYRGWRGRLKFARKPFCVIDIMVLIASIAVLAAGSQGNVFATSALRSLRFLQILRMIRMDRRGGTWKLL
mKvLR1      EYFVRIWAAGCCCRYRGWRGRLKFARKPFCVIDIMVLIASIAVLAAGSQGNVFATSALRSLRFLQILRMIRMDRRGGTWKLL
rKvLR1      EYFVRIWAAGCCCRYRGWRGRLKFARKPFCVIDIMVLIASIAVLAAGSQGNVFATSALRSLRFLQILRMIRMDRRGGTWKLL
```

FIG. 17A

```
                                       S5                                                     P
Consensus  GS----AHSKEL-TAWYIGFL-LIL-SFLVYL-EK-E-D-*******F-TYADALWGLITL-TIGYGDK-P-TW-GRLhKvLR2     GSAICAHSKELITAWYIGFLTLILSSFLVYLVEKDVPEVDAQGEEMKEEFETYADALWGLITLATIGYGDKTPKITWEGRLI
hKvLR1     GSVVYAHSKELVTAWYIGFLCLILASFLVYLAEK*****GENDH*****FDTYADALWGLITLTTIGYGDKYPQTWNGRLL
mKvLR1     GSVVYAHSKELVTAWYIGFLCLILASFLVYLAEK*******GENDH*******FDTYADALWGLITLTTIGYGDKYPQTWNGRLL
rKvLR1     GSVVYAHSKELVTAWYIGFLCLILASFLVYLAEK*****GENDH*****FDTYADALWGLITLTTIGYGDKYPQTWNGRLL S6
Consensus  AATF-LIGVSFFALPAGILGSG-ALKVQEQHRQKHFEKRR-PAA-LIQ-AWR-YATN--R-DL---- hKvLR2     AATFSLIGVSFFALPAGILGSGLALKVQEQHRQKHFEKRRKPAAELIQAAWRYYATNPNRIDLVGDM
hKvLR1     AATFTLIGVSFFALPAGILGSGFALKVQEQHRQKHFEKRRNPAAGLIQSAWRFYATNLSRTDLHSTW
mKvLR1     AATFTLIGVSFFALPAGILGSGFALKVQEQHRQKHFEKRRNPAAGLIQSAWRFYATNLSRTDLHSTW
rKvLR1     AATFTLIGVSFFALPAGILGSGFALKVQEQHRQKHFEKRRNPAAGLIQSAWRFYATNLSRTDLHSTW
```

FIG. 17B

KCNQ2　　　　　　　　KCNQ3

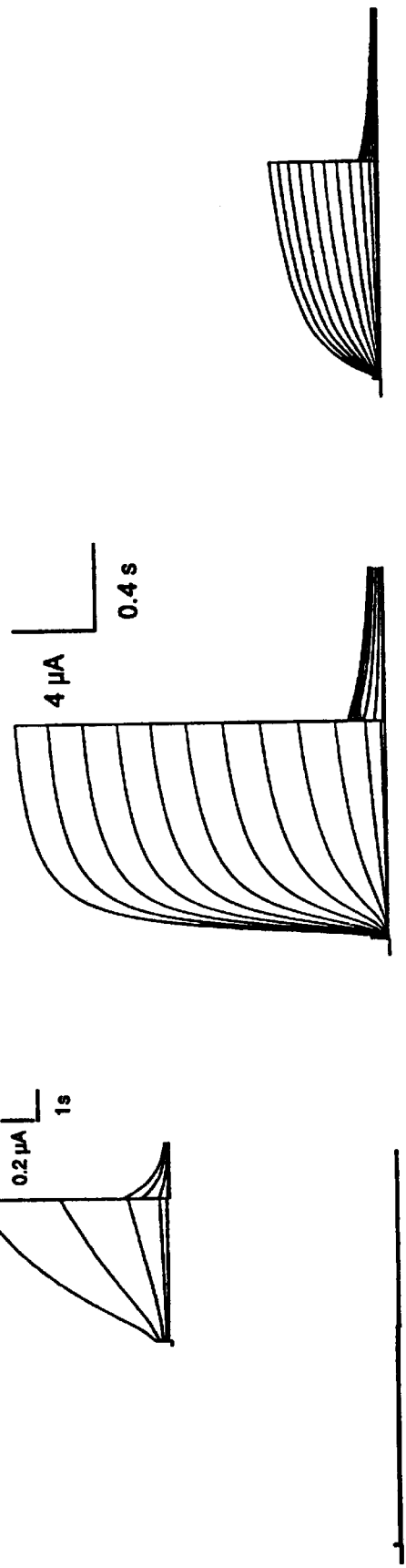

```
ATG GCA TTG GAG TTC CCG GCG GCT AAC CCA GCC GGA GGG GAC GCG  45
 M   A   L   E   F   P   A   A   N   P   A   G   G   D   A
             5                  10                      15

GCG GCG GCC GGC GAC GAG GAG CGG AAA GTG GGG CTG GCG CCC GGC  90
 A   A   A   G   D   E   E   R   K   V   G   L   A   P   G
                    20                  25                  30

GAC GTG GAG CAA GTC ACC TTG GCG CTC GGG GCC GGA GCC GAC AAA 135
 D   V   E   Q   V   T   L   A   L   G   A   G   A   D   K
                 35                      40                  45

GAC GGG ACC CTG CTG CTG GAG GGC GGC GGC CGC GAC GAG GGG CAG 180
 D   G   T   L   L   L   E   G   G   G   R   D   E   G   Q
                 50                      55                  60

CGG AGG ACC CCG CAG GGC ATC GGG CTC CTG GCC AAG ACC CCG CTG 225
 R   R   T   P   Q   G   I   G   L   L   A   K   T   P   L
                 65                      70                  75

AGC CGC CCA GTC AAG AGA AAC AAC GCC AAG TAC CGG CGC ATC CAA 270
 S   R   P   V   K   R   N   N   A   K   Y   R   R   I   Q
                 80                      85                  90

ACT TTG ATC TAC GAC GCC CTG GAG AGA CCG CGG GGC TGG GCG CTG 315
 T   L   I   Y   D   A   L   E   R   P   R   G   W   A   L
                 95                     100                 105

CTT TAC CAC GCG TTG GTG TTC CTG ATT GTC CTG GGG TGC TTG ATT 360
 L   Y   H   A   L   V   F   L   I   V   L   G   C   L   I
                110                     115                 120

CTG GCT GTC CTG ACC ACA TTC AAG GAG TAT GAG ACT GTC TCG GGA 405
 L   A   V   L   T   T   F   K   E   Y   E   T   V   S   G
                125                     130                 135

GAC TGG CTT CTG TTA CTG GAG ACA TTT GCT ATT TTC ATC TTT GGA 450
 D   W   L   L   L   L   E   T   F   A   I   F   I   F   G
                140                     145                 150

GCC GAG TTT GCT TTG AGG ATC TGG GCT GCT GGA TGT TGC TGC CGA 495
 A   E   F   A   L   R   I   W   A   A   G   C   C   C   R
                155                     160                 165

TAC AAA GGC TGG CGG GGC CGA CTG AAG TTT GCC AGG AAG CCC CTG 540
 Y   K   G   W   R   G   R   L   K   F   A   R   K   P   L
                170                     175                 180

TGC ATG TTG GAC ATC TTT GTG CTG ATT GCC TCT GTG CCA GTG GTT 585
 C   M   L   D   I   F   V   L   I   A   S   V   P   V   V
                185                     190                 195
```

FIG. 23A

```
GCT GTG GGA AAC CAA GGC AAT GTT CTG GCC ACC TCC CTG CGA AGC  630
 A   V   G   N   Q   G   N   V   L   A   T   S   L   R   S
            200                 205                 210

CTG CGC TTC CTG CAG ATC CTG CGC ATG CTG CGG ATG GAC CGG AGA  675
 L   R   F   L   Q   I   L   R   M   L   R   M   D   R   R
            215                 220                 225

GGT GGC ACC TGG AAG CTT CTG GGC TCA GCC ATC TGT GCC CAC AGC  720
 G   G   T   W   K   L   L   G   S   A   I   C   A   H   S
            230                 235                 240

AAA GAA CTC ATC ACG GCC TGG TAC ATC GGT TTC CTG ACA CTC ATC  765
 K   E   L   I   T   A   W   Y   I   G   F   L   T   L   I
            245                 250                 255

CTT TCT TCA TTT CTT GTC TAC CTG GTT GAG AAA GAC GTC CCA GAG  810
 L   S   S   F   L   V   Y   L   V   E   K   D   V   P   E
            260                 265                 270

GTG GAT GCA CAA GGA GAG GAG ATG AAA GAG GAG TTT GAG ACC TAT  855
 V   D   A   Q   G   E   E   M   K   E   E   F   E   T   Y
            275                 280                 285

GCA GAT GCC CTG TGG TGG GGC CTG ATC ACA CTG GCC ACC ATT GGC  900
 A   D   A   L   W   W   G   L   I   T   L   A   T   I   G
            290                 295                 300

TAT GGA GAC AAG ACA CCC AAA ACG TGG GAA GGC CGT CTG ATT GCC  945
 Y   G   D   K   T   P   K   T   W   E   G   R   L   I   A
            305                 310                 315

GCC ACC TTT TCC TTA ATT GGC GTC TCC TTT TTT GCC CTT CCA GCG  990
 A   T   F   S   L   I   G   V   S   F   F   A   L   P   A
            320                 325                 330

GGC ATC CTG GGG TCC GGG CTG GCC CTC AAG GTG CAG GAG CAA CAC 1035
 G   I   L   G   S   G   L   A   L   K   V   Q   E   Q   H
            335                 340                 345

CGT CAG AAG CAC TTT GAG AAA AGG AGG AAG CCA GCT GCT GAG CTC 1080
 R   Q   K   H   F   E   K   R   R   K   P   A   A   E   L
            350                 355                 360

ATT CAG GCT GCC TGG AGG TAT TAT GCT ACC AAC CCC AAC AGG ATT 1125
 I   Q   A   A   W   R   Y   Y   A   T   N   P   N   R   I
            365                 370                 375

GAC CTG GTG GCG ACA TGG AGA TTT TAT GAA TCA GTC GTC TCT TTT 1170
 D   L   V   A   T   W   R   F   Y   E   S   V   V   S   F
            380                 385                 390
```

FIG. 23B

```
CCT TTC TTC AGG AAA GAA CAG CTG GAG GCA GCA TCC AGC CAA AAG  1215
 P   F   F   R   K   E   Q   L   E   A   A   S   S   Q   K
            395                 400                 405

CTG GGT CTC TTG GAT CGG GTT CGC CTT TCT AAT CCT CGT GGT AGC  1260
 L   G   L   L   D   R   V   R   L   S   N   P   R   G   S
            410                 415                 420

AAT ACT AAA GGA AAG CTA TTT ACC CCT CTG AAT GTA GAT GCC ATA  1305
 N   T   K   G   K   L   F   T   P   L   N   V   D   A   I
            425                 430                 435

GAA GAA AGT CCT TCT AAA GAA CCA AAG CCT GTT GGC TTA AAC AAT  1350
 E   E   S   P   S   K   E   P   K   P   V   G   L   N   N
            440                 445                 450

AAA GAG CGT TTC CGC ACG GCC TTC CGC ATG AAA GCC TAC GCT TTC  1395
 K   E   R   F   R   T   A   F   R   M   K   A   Y   A   F
            455                 460                 465

TGG CAG AGT TCT GAA GAT GCC GGG ACA GGT GAC CCC ATG GCG GAA  1440
 W   Q   S   S   E   D   A   G   T   G   D   P   M   A   E
            470                 475                 480

GAC AGG GGC TAT GGG AAT GAC TTC CCC ATC GAA GAC ATG ATC CCC  1485
 D   R   G   Y   G   N   D   F   P   I   E   D   M   I   P
            485                 490                 495

ACC CTG AAG GCC GCC ATC CGA GCC GTC AGA ATT CTA CAA TTC CGT  1530
 T   L   K   A   A   I   R   A   V   R   I   L   Q   F   R
            500                 505                 510

CTC TAT AAA AAA AAA TTC AAG GAG ACT TTG AGG CCT TAC GAT GTG  1575
 L   Y   K   K   K   F   K   E   T   L   R   P   Y   D   V
            515                 520                 525

AAG GAT GTG ATT GAG CAG TAT TCT GCC GGG CAT CTC GAC ATG CTT  1620
 K   D   V   I   E   Q   Y   S   A   G   H   L   D   M   L
            530                 535                 540

TCC AGG ATA AAG TAC CTT CAG ACG AGA ATA GAT ATG ATT TTC ACC  1665
 S   R   I   K   Y   L   Q   T   R   I   D   M   I   F   T
            545                 550                 555

CCT GGA CCT CCC TCC ACG CCA AAA CAC AAG AAG TCT CAG AAA GGG  1710
 P   G   P   P   S   T   P   K   H   K   K   S   Q   K   G
            560                 565                 570

TCA GCA TTC ACC TTC CCA TCC CAG CAA TCT CCC AGG AAT GAA CCA  1755
 S   A   F   T   F   P   S   Q   Q   S   P   R   N   E   P
            575                 580                 585
```

FIG. 23C

```
TAT GTA GCC AGA CCA TCC ACA TCA GAA ATC GAA GAC CAA AGC ATG 1800
 Y   V   A   R   P   S   T   S   E   I   E   D   Q   S   M
             590             595             600

ATG GGG AAG TTT GTA AAA GTT GAA AGA CAG GTT CAG GAC ATG GGG 1845
 M   G   K   F   V   K   V   E   R   Q   V   Q   D   M   G
             605             610             615

AAG AAG CTG GAC TTC CTC GTG GAT ATG CAC ATG CAA CAC ATG GAA 1890
 K   K   L   D   F   L   V   D   M   H   M   Q   H   M   E
             620             625             630

CGG TTG CAG GTG CAG GTC ACG GAG TAT TAC CCA ACC AAG GGC ACC 1935
 R   L   Q   V   Q   V   T   E   Y   Y   P   T   K   G   T
             635             640             645

TCC TCG CCA GCT GAA GCA GAG AAG AAG GAG GAC AAC AGG TAT TCC 1980
 S   S   P   A   E   A   E   K   K   E   D   N   R   Y   S
             650             655             660

GAT TTG AAA ACC ATC ATC TGC AAC TAT TCT GAG ACA GGC CCC CCG 2025
 D   L   K   T   I   I   C   N   Y   S   E   T   G   P   P
             665             670             675

GAA CCA CCC TAC AGC TTC CAC CAG GTG ACC ATT GAC AAA GTC AGC 2070
 E   P   P   Y   S   F   H   Q   V   T   I   D   K   V   S
             680             685             690

CCC TAT GGG TTT TTT GCA CAT GAC CCT GTG AAC CTG CCC CGA GGG 2115
 P   Y   G   F   F   A   H   D   P   V   N   L   P   R   G
             695             700             705

GGA CCC AGT TCT GGA AAG GTT CAG GCA ACT CCT CCT TCC TCA GCA 2160
 G   P   S   S   G   K   V   Q   A   T   P   P   S   S   A
             710             715             720

ACA ACG TAT GTG GAG AGG CCC ACG GTC CTG CCT ATC TTG ACT CTT 2205
 T   T   Y   V   E   R   P   T   V   L   P   I   L   T   L
             725             730             735

CTC GAC TCC CGA GTG AGC TGC CAC TCC CAG GCT GAC CTG CAG GGC 2250
 L   D   S   R   V   S   C   H   S   Q   A   D   L   Q   G
             740             745             750

CCC TAC TCG GAC CGA ATC TCC CCC CGG CAG AGA CGT AGC ATC ACG 2295
 P   Y   S   D   R   I   S   P   R   Q   R   R   S   I   T
             755             760             765

CGA GAC AGT GAC ACA CCT CTG TCC CTG ATG TCG GTC AAC CAC GAG 2340
 R   D   S   D   T   P   L   S   L   M   S   V   N   H   E
             770             775             780
```

FIG. 23D

```
GAG CTG GAG AGG TCT CCA AGT GGC TTC AGC ATC TCC CAG GAC AGA  2385
 E   L   E   R   S   P   S   G   F   S   I   S   Q   D   R
                 785                 790                 795

GAT GAT TAT GTG TTC GGC CCC AAT GGG GGG TCG AGC TGG ATG AGG  2430
 D   D   Y   V   F   G   P   N   G   G   S   S   W   M   R
                 800                 805                 810

GAG AAG CGG TAC CTC GCC GAG GGT GAG ACG GAC ACA GAC ACG GAC  2475
 E   K   R   Y   L   A   E   G   E   T   D   T   D   T   D
                 815                 820                 825

CCC TTC ACG CCC AGC GGC TCC ATG CCT CTG TCG TCC ACA GGG GAT  2520
 P   F   T   P   S   G   S   M   P   L   S   S   T   G   D
                 830                 835                 840

GGG ATT TCT GAT TCA GTA TGG ACC CCT TCC AAT AAG CCC ATT TAA  2565
 G   I   S   D   S   V   W   T   P   S   N   K   P   I   *
                 845                 850                 854
```

FIG. 23E

KCNQ POTASSIUM CHANNELS AND METHODS OF MODULATING SAME

This application is related to provisional application Ser. No. 60/055,599 filed Aug. 12, 1997, from which priority is claimed under 35 U.S.C. 119(e)(1), the disclosure of which is hereby incorporated by reference in its entirety.

FIELD OF THE INVENTION

The present invention concerns nucleic acids and proteins for potassium channels, as well as related vectors, host cells, processes for preparation, and methods of use. Included within the present invention are methods of screening for compounds that bind to and/or otherwise modulate the potassium channel proteins disclosed herein. Additionally, the present invention encompasses methods of modulating the potassium channels disclosed herein, for example methods of opening/activating or closing/inactivating said potassium channels.

BACKGROUND OF THE INVENTION

Among ion channels, potassium ion ($K^+$) channels are the most ubiquitous and diverse. They include three major structural classes—channels with six, four, or two transmembrane domains. The six transmembrane domain potassium channels are divided further into different families, such as Shaker-like, eag-like and Slo-like potassium channels. Recent identification of KvLQT1 established a new family of six-transmembrane potassium channels. Barhanin et al. (1996) *Nature* 384: 78–80; Sanguinetti et al. (1996) *Nature* 384: 80–83; Yang et al. (1997) *Proc. Natl. Acad. Sci. USA* 94: 4017–22; Wang et al. (1996) *Nature Genetics* 12: 17–23. Search of DNA and protein sequence databanks reveals additional potential members of KvLQT1-related channels in *C. elegans* as well as in the human. Wei et al. (1996), *Neuropharmacology* 35: 805–29;; Yang et al. (1997) *Proc. Natl. Acad. Sci. USA* 94: 4017–2.

One or more types of $K^+$ channels reside on cell membranes where they are remarkably selective for $K^+$ over other ions. In excitable cells, $K^+$ channels modulate action potential configuration. Efflux of potassium is the major mechanism for repolarization, maintenance, and hyperpolarization of resting membrane potential. Halliwell (1990) in *Potassium channels-structure, classification. function and therapeutic potential* (N. S. Cook, ed.); 348–381; Jan, L. Y. and Jan, Y. N. (1992), *Ann. Rev. Physiol.* 54: 537–55; Pongs (1992), *Physiol. Rev.* 72: S69–S88.

In neurons, $K^+$ channels regulate neuronal excitability, action potential shape and firing pattern, and neurotransmitter release. These channels can be gated by various stimuli, such as intracellular second messengers, membrane potential, ions, and neurotransmitters. Hille (1992), *Ionic channels of excitable membranes*; Catterall (1995), *Ann. Rev. Biochem.* 64: 493–531. Neuronal $K^+$ channels are critical to such neuronal functions as neurotransmission and neuroprotection, and they may affect perception, learning, behavior, and the like.

Recently, the nomenclature for KvLQT1 and the KvLQT1-related channels was changed. Biervert et al. (1998), *Science* 279:403–406. KvLQT1 was re-named KCNQ1, and the KvLQT1-related channels (KvLR1 and KvLR2) were re-named as KCNQ2 and KCNQ3, respectively. Therefore, throughout this specification, reference to KCNQ1 is equivalent to KvLQT1; reference to KCNQ2 is equivalent to KvLR1; and reference to KCNQ3 is equivalent to KvLR2.

Benign familial neonatal convulsions ("BFNC"), a class of idiopathic generalized epilepsy, is an autosomal-dominantly inherited disorder of newborns. BFNC has recently been linked to mutations in two putative $K^+$ channel genes, KCNQ2 and KCNQ3. Biervert et al., supra; Charlier et al. (1998), *Nature Genetics* 18:53–55; Singh et al. (1998) *Nature Genetics* 18:25–29. Preliminary functional characterization of KCNQ2 confirmed that this gene encodes a voltage-activated $K^+$ channel. Singh et al., supra.

SUMMARY OF THE INVENTION

The present invention discloses novel nervous system-specific potassium channels referred to herein as KCNQ2 (formerly called KvLR1) and KCNQ3 (formerly called KvLR2). Within the present invention are human KCNQ2 (FIG. 2), human KCNQ3 (FIG. 23), murine KCNQ2 (FIG. 10), and rat KCNQ2 (FIG. 16 and FIG. 17). The invention encompasses the amino acid sequences of these proteins and the nucleic acid sequences encoding said proteins, as well as variations in the nucleic acid sequences due to degeneracy in the genetic code.

The present invention provides for nucleic acid molecules at least about 70% identical to the consensus sequence of the nucleotide sequences disclosed herein. Preferably, the present invention provides: (a) a purified and isolated nucleic acid molecule encoding a KCNQ2 and/or KCNQ3 protein of the present invention; (b) nucleic acid sequences complementary to (a); (c) nucleic acid sequences having at least 70% sequence identity, more preferably at least 80%, more preferably at least 90%, more preferably at least 95%, and most preferably at least 98% sequence identity to (a); or (d) a fragment of (a) or (b) which will hybridize to (a) or (b) under stringent conditions, said fragment preferably comprising at least 15 nucleotides. Preferred nucleic acid sequences encoding the KCNQ2 and KCNQ3 proteins of the present invention are found in SEQ ID NO:3, SEQ ID NO:19, SEQ ID NO:17, SEQ ID NO:26, SEQ ID NO:7, SEQ ID NO:5 and SEQ ID NO:22.

Also within the scope of the present invention are amino acid sequences at least about 70% identical to the consensus sequence of the proteins disclosed herein. Preferably, the invention covers: (a) amino acid sequences comprising the KCNQ2 and/or KCNQ3 proteins of the present invention; and (b) amino acid sequences having at least 70% sequence identity, more preferably at least 80%, more preferably at least 90%, more preferably at least 95%, and most preferably at least 98% sequence identity to (a). Preferred amino acid sequences comprising the KCNQ2 and KCNQ3 proteins of the present invention are found in SEQ ID NO:4, SEQ ID NO:20, SEQ ID NO:18, SEQ ID NO:27, SEQ ID NO:8, SEQ ID NO:6 and SEQ ID NO:23.

The invention further concerns novel nucleic acids and associated vectors, host cells, and methods of use. Preferably, the nucleic acid molecule is a DNA molecule. Further preferred are nucleotide sequences encoding the amino acid sequences of SEQ ID NO:2, SEQ ID NO:4, SEQ ID NO:20, SEQ ID NO:6, SEQ ID NO:23, SEQ ID NO:8, SEQ ID NO:18 and SEQ ID NO:27, as well as proteins about 70% or more identical to these sequences. Also preferred are nucleotide sequences about 80% or more identical to SEQ ID NO:1; most preferred are SEQ ID NO:3, SEQ ID NO:19, SEQ ID NO:5, SEQ ID NO:22, SEQ ID NO:7, SEQ ID NO:17 and SEQ ID NO:26.

The invention further concerns nucleic acids obtained by PCR with degenerate oligonucleotide primers. Persons of ordinary skill in the art could devise such primers based on the consensus sequence described herein. PCR techniques are described in White et al. (1989), *Trends Genet*. 5: 185–9.

This invention further concerns nucleic acid vectors comprising a nucleic acid sequence coding for a KvLR/KCNQ protein, host cells containing such vectors, and polypeptides comprising the amino acid sequence of a KvLR/KCNQ protein. Preferably, the vector encodes a full-length KvLR/KCNQ protein and the polypeptide is full-length KvLR/KCNQ protein. The inventors prefer frog expression vectors such as pSP64T or derivatives thereof (Melton et al. (1984), *Nucl. Acids Res*. 12: 7057–70); mammalian cell expression vectors such as pcDNA3 (available from Invitrogen); or bacterial cell expression vectors such as pET-30 (available from Novagen or Promega).

This invention further concerns host cells transformed with the above-described vectors. The inventors prefer Xenopus oocytes, mammalian cells (e.g., HEK293, CHO, L929), and bacterial cells (e.g., *E. coli*, especially BL21 (DE3), available from Novagen). The inventors particularly prefer the cells deposited as ATCC Acc. No. CRL-1573 (American Type Culture Collection, 10801 University Boulevard, Manassas Va. 20110-2209).

The invention also concerns methods for detecting nucleic acids coding for KCNQ/KvLR proteins and processes for detecting molecules that bind to and/or otherwise modulate the activity of KCNQ/KvLR proteins. "Modulate" encompasses both channel openers/activators and channel closers/inactivators.

The invention also concerns methods of modulating the KCNQ proteins, specifically methods of opening/activating or closing/inactivating the KCNQ2 and/or KCNQ3 channels. Additionally, the present invention encompasses a method of treating disease by modulating the activity of the KCNQ proteins.

All references cited herein, whether supra or infra, are hereby incorporated herein in their entirety.

DESCRIPTION OF THE DRAWINGS

FIGS. 2A and 2B show the nucleotide (SEQ ID NO:10) and deduced amino acid (SEQ ID NO:20) sequence of human KCNQ2/KvLR1.

FIG. 3 show a sequence comparison of human KCNQ2/KvLR1 (SEQ ID NO:20) and human KCNQ1/KvLQT1 (SEQ ID NO:21) "|" denotes amino acid sequence identity. The C-terminal amino acids of both proteins are not shown.

FIG. 4 shows a sequence comparison of human KCNQ3/KvLR2 and human KCNQ1/KvLQT1. "|" denotes amino acid sequence identity. The C-terminal amino acids of both proteins are not shown. The N terminal amino acids of KCNQ3/KvLR2 (SEQ ID NO:18 and SEQ ID NO:27) are not shown.

FIG. 5 shows expression of KCNQ2/KvLR1 and KCNQ3/KvLR2 in human tissues and various portions of human brain.

FIG. 6 shows functional characterization of KCNQ2/KvLR1 currents in Xenopus oocytes.

In FIGS. 6A and 6B, families of currents from water-injected (FIG. 6A) and human KCNQ2/KvLR1 cRNA-injected (FIG. 6B) oocytes were elicited by 1 second voltage steps, from a holding potential of −80 mV, to test potentials ranging from −100 to +40 mV in 10 mV increments.

FIG. 6C shows the peak current-voltage (I-V) relationship for oocytes expressing human KCNQ2/KvLR1. Currents were recorded using the protocol described above for FIGS. 6A and 6B.

FIG. 6D shows dependence of tail current reversal potential ($E_{rev}$) on the external K$^+$ concentration. Tail currents were elicited at potentials of −110 to +10 mV following a 1 second pulse to +20 mV (n=6 oocytes) while the external K$^+$ concentration was varied between 2, 10, 40, and 98 mM. $E_{rev}$ under each condition was determined for each oocyte by measuring the zero intercept from a plot of tail current amplitude versus test potential. The dashed line has a slope of 58 mV and is drawn according to the Nernst equation for a perfectly selective K$^+$ channel. Data are the mean±SEM from six experiments.

FIG. 8 shows co-expression of minK and human KCNQ2/KvLR1 in Xenopus oocytes.

FIG. 9 shows murine KCNQ2/KvLR1 expression in the brain of adult mouse.

FIG. 9C shows partial murine KCNQ2/KvLR1 nucleotide sequence (SEQ ID NO:9) and amino acid sequence (SEQ ID NO:10). This sequence was obtained through PCR amplification of a mouse brain cDNA library using the oligonucleotides MABms 278 (SEQ ID NO:11) and MABms 315 (SEQ ID NO:12) based on the human KCNQ2/KvLR1 sequence. The PCR fragments were isolated, subcloned, and sequenced. A 226 bp fragment as shown above was used in a probe for in situ hybridization. The nucleotide sequence is 80% identical to human KCNQ2/KvLR1 (96% identity in amino acid sequence).

MABms 278 (SEQ ID NO:11):
5'-GGCCGAATTCTGTTTCTCAGCAGCTCCAGC-3'

MABms 315 (SEQ ID NO:12):
5'-GCGCGAATTCGAGCAGCACAGGCA(A/G)AA(A/G)CA-3'

FIG. 10A through FIG. 10D show the DNA (SEQ ID NO:22) and translated amino acid (SEQ ID NO:23) sequence of the mouse brain KCNQ2/KvLR1 gene. FIG. 10E shows hydropathy analysis of the mouse brain KCNQ2/KvLR1 gene. The hydropathy plot reveals the pattern typical of voltage-sensitive $K^+$ channels with 6 putative membrane spanning domains (S1–S6) and a pore region (P).

FIG. 11 shows sequence, alignment of the mouse heart KCNQ1/KvLQT1 (SEQ ID NO:24) and mouse brain KCNQ2/KvLR1 (SEQ ID NO: 23) potassium channels. The alignment of these two proteins shows a 40% overall amino acid identity (indicated by the shaded areas) and 62.5% identity within the spanning and pore domains. Putative membrane spanning and pore domains are indicated by the boxes. The signature sequence for a potassium channel, GYG, is observed within the pore region and the voltage sensor, RXXQXXRXXR (SEQ ID NO:25), is within the S4 domain.

Figure 12:

FIG. 12 shows alternative splice exons, A and B (SEQ ID NOS: 13 and 14), in the 3' end of murine KCNQ2/KvLR1. FIG. 12 depicts the at least two splice exons within the 3' region of the murine KCNQ2/KvLR1 protein, from amino acids 355 to 474 of SEQ ID NO:23. Amino acids 355 to 474 of murine KCNQ2/KvLR1 are designated as SEQ ID NO:28. When translated, the A and B splice exons result in the amino acid sequences presented in SEQ ID NOS: 13 and 14, respectively, which have been identified in the murine KCNQ2/KvLR1 at amino acid positions 372 and 406, respectively.

Figure 13:
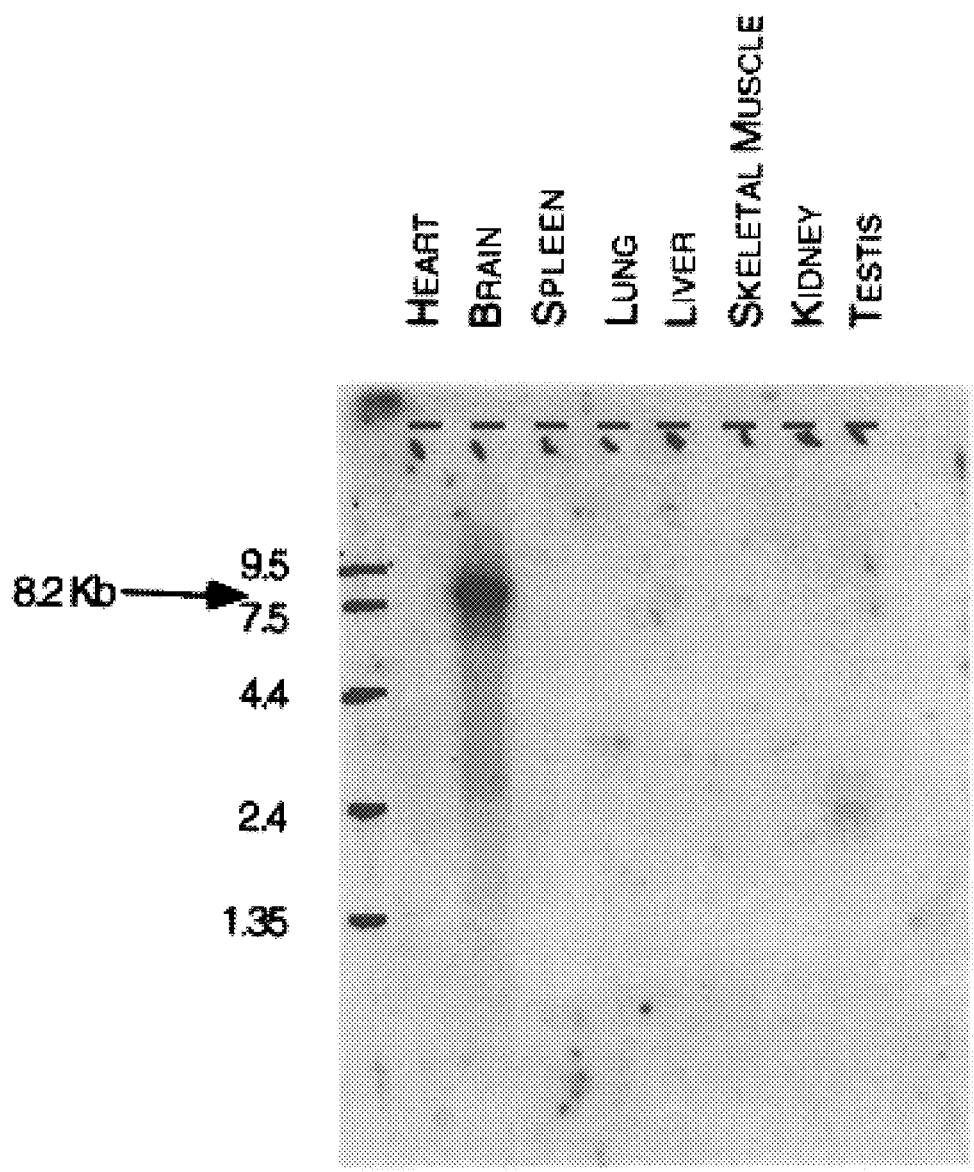
Figure 14A:
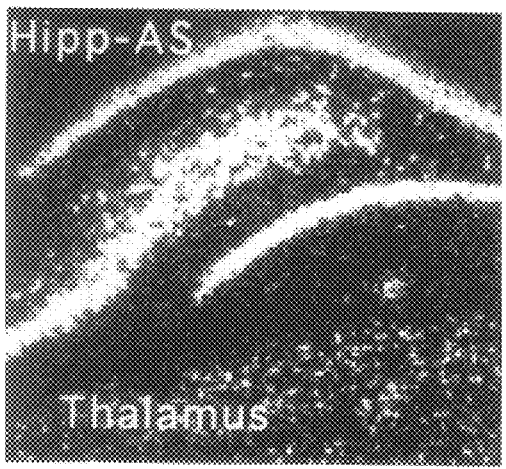
Figure 14B:
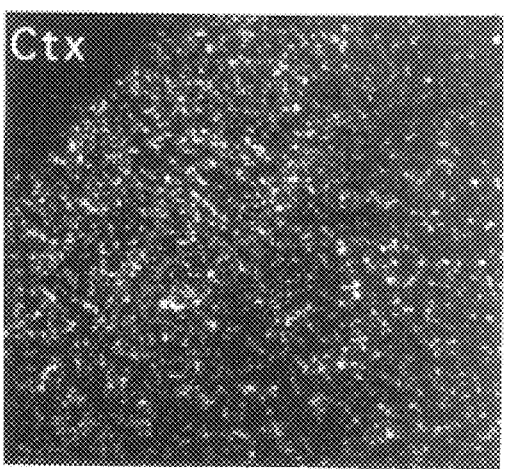
Figure 14C:
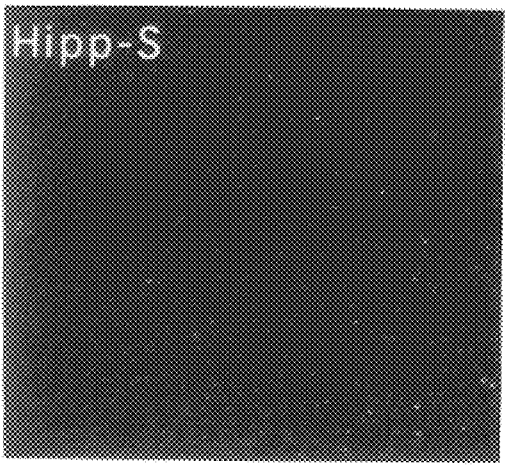
Figure 14D:
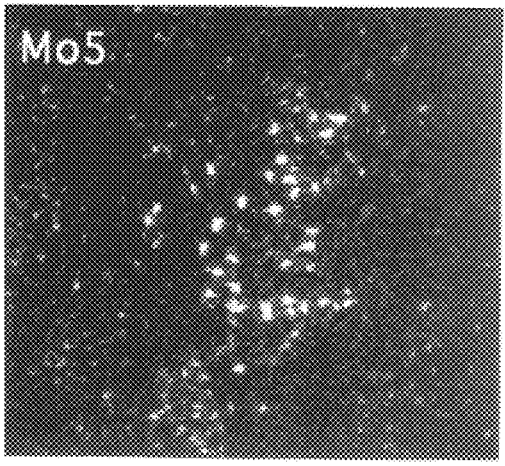

FIG. 13 shows a mouse multiple tissue northern blot. A northern blot was probed with a fragment of the mouse KCNQ2/KvLR1 gene (nucleotides 1140–2306). A single transcript of 8.2 kb is observed in brain, but not is seen in other tissues.

FIG. 14 shows in situ hybridization of rat brain. The composite shows three regions where the rat KCNQ2/KvLR1 message is strongly expressed. The antisense probes show strong signal in the hippocampus, dentate gyrus, cortex, and motor nucleus of the trigeminal nerve. Sense probe controls show little background.

FIG. 15 shows electrophysiology characterization of mouse KCNQ2/KvLR1-mediated whole-cell currents expressed in Xenopus oocytes. In FIG. 15A, 10 mV step depolarizations from a −80 to +40 produced a family of outward currents that were significantly different than control cells. Addition of 1 mM TEA blocked the KvLR1-mediated currents and background chloride currents were not affected by TEA. Clofilium, a blocker of heart $I_{Ks}$ and $I_{Kr}$ currents, was shown to partially block the KCNQ2/KvLR1-mediated currents when depolarized to from −80 to +40 $\mu$V. FIG. 15B shows uninjected controls.

Figure 16A:
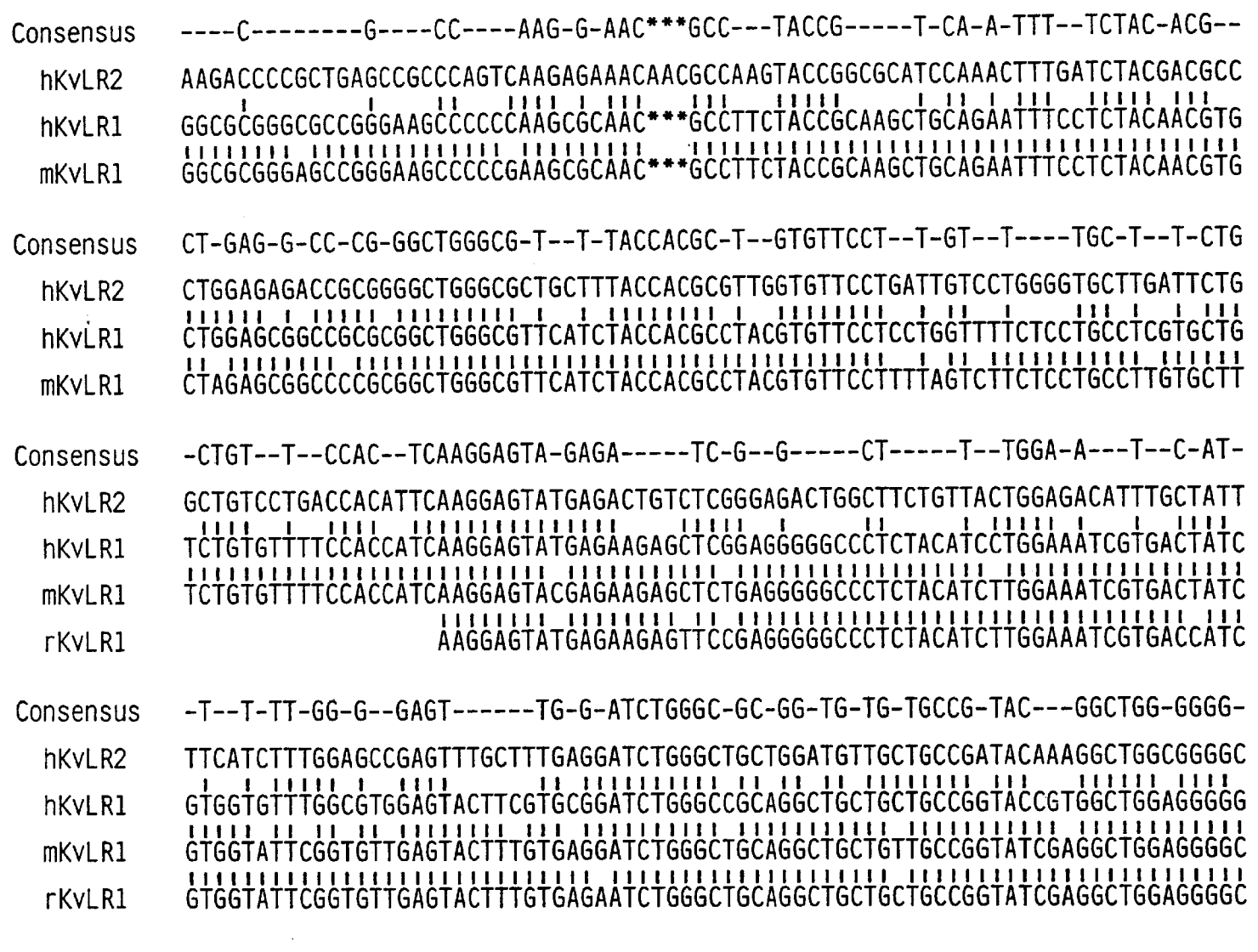
Figure 16B:
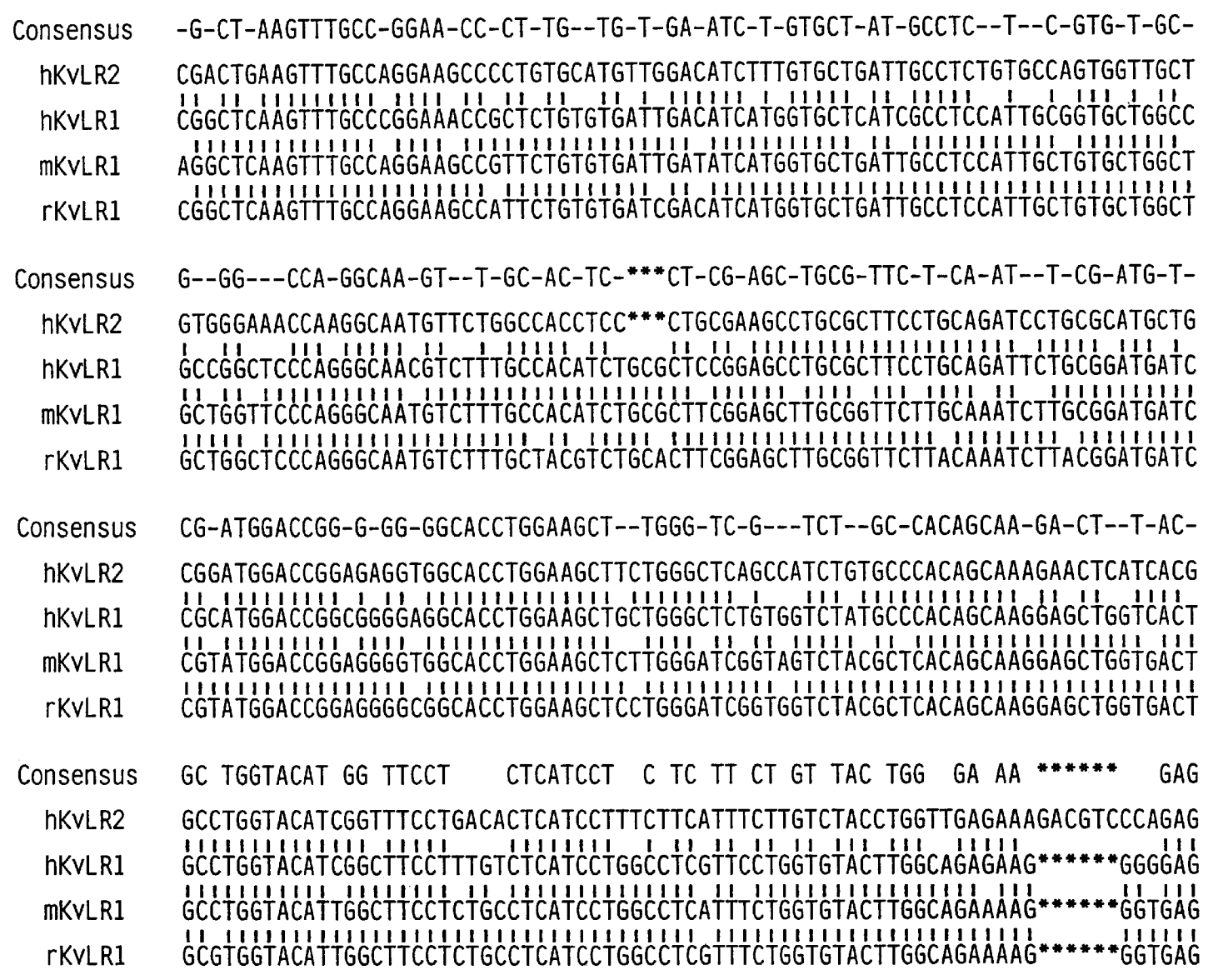
Figure 16C:
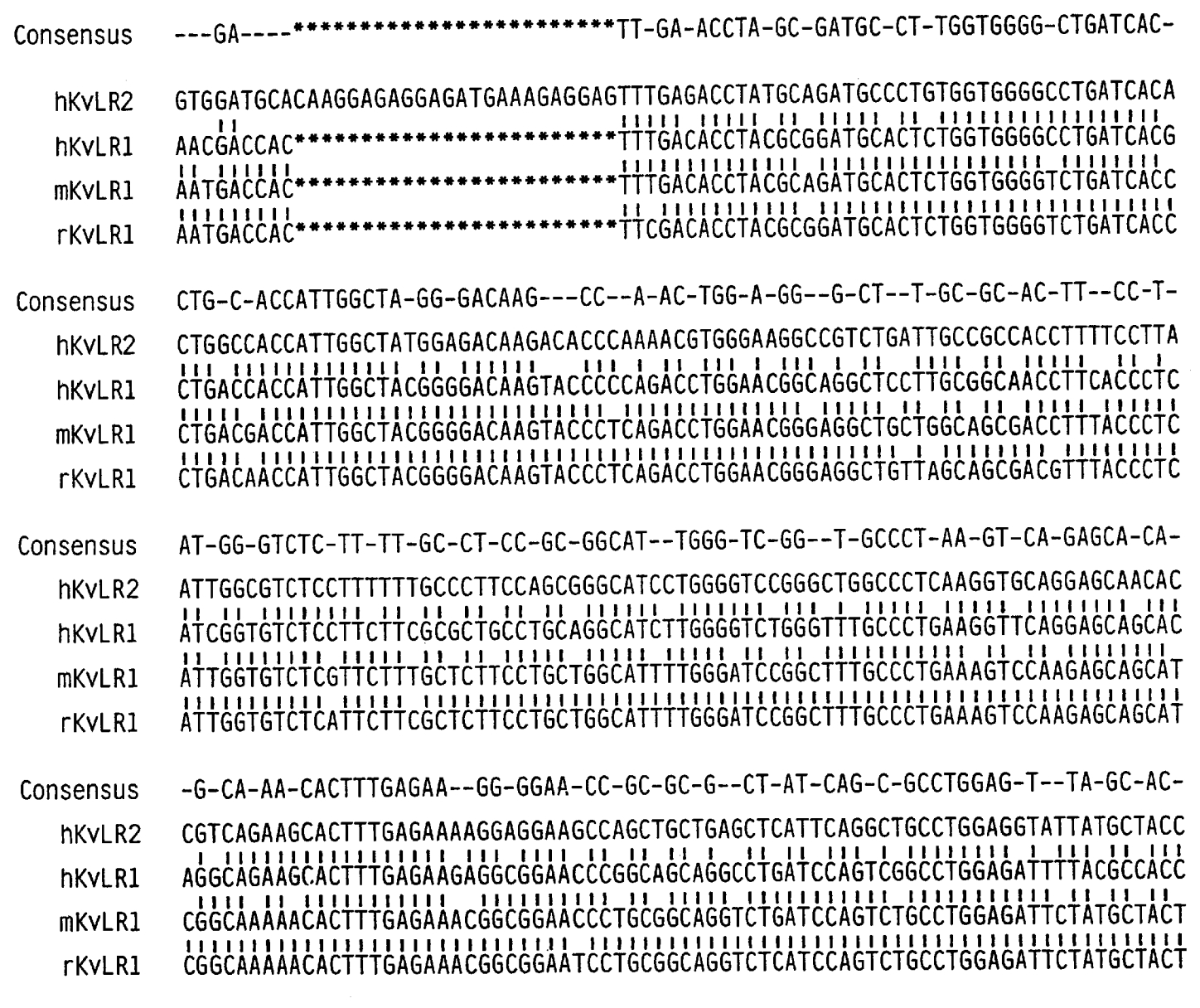

FIG. 16 shows an alignment of the consensus nucleotide sequence (SEQ ID NO:1) and the nucleotide sequences of the human KCNQ3/KvLR2 (SEQ ID NO:17, SEQ ID NO:26), human KCNQ2/KvLR1 (SEQ ID NO:3, SEQ ID NO:19), mouse KCNQ2/KvLR1 (SEQ ID NO:5, SEQ ID NO:22), and rat KCNQ2/KvLR1 (SEQ ID NO:7). "|" denotes sequence identity; "-" represents non-consensus sequence; and "*" denotes a space introduced to optimize sequence identity.

FIG. 17 shows an alignment of the consensus amino acid sequence (SEQ ID NO:2) and the amino acid sequences of the human KCNQ3/KvLR2 (SEQ ID NO:18, SEQ ID NO:27), human KCNQ2/KvLR1 (SEQ ID NO:4, SEQ ID NO:20), mouse KCNQ2/KvLR1 (SEQ ID NO:6, SEQ ID NO:23), and rat KCNQ2/KvLR1 (SEQ ID NO:8) proteins. As in FIG. 16, "|" denotes sequence identity; "-" represents non-consensus sequence; and "*" denotes a space introduced to optimize sequence identity.

FIG. 18 shows the functional characterization of KCNQ3 currents. FIG. 18A shows families of currents from KCNQ3 cRNA-injected oocytes elicited by 1 sec voltage steps, from a holding potential of −80 mV, to test potentials ranging from −70 to +50 mV in 10 mV increments. FIG. 18B shows I-V relationship for oocytes expressing KCNQ3 (n=6). Currents were recorded using the protocol in FIG. 18A. FIG. 18C shows dependence of tail current $E_{rev}$ on the external $K^+$ concentration. The line has a slope predicted by the Nernst equation for a perfectly selective $K^+$ channel. Each value is the mean±SEM from 6 oocytes. FIG. 18D shows effects of E-4031, 4-AP, TEA and clofilium on KCNQ3 current. Superimposed currents were recorded during 1 sec steps to +20 mV, from −80 mV, during the same experiment. Compounds were applied via bath perfusion in order from top to bottom. The bath was perfused with control solution for 5 min, or until effects reversed completely, between compounds. Similar results were obtained in three additional oocytes.

FIG. 19 shows co-expression of KCNQ2 and KCNQ3. FIG. 19A shows families of currents from KCNQ2, FIG. 19B from KCNQ3, and FIG. 19C from KCNQ2+KCNQ3 cRNA-injected oocytes elicited by 1 sec voltage steps, from a holding potential of −80 mV, to test potentials ranging from −70 to +50 mV (10 mV increments). FIG. 19D shows current-voltage (I-V) relationship for oocytes expressing KCNQ2+KCNQ3 (n=6). Currents were recorded using the protocol in FIGS. 19A–19C. FIG. 19E shows dependence of tail current reversal potential (Erev) on the external $K^+$ concentration. The dashed line has a slope predicted by the Nernst equation for a perfectly selective $K^+$ channel. Each value is the mean±SEM from 6 oocytes. FIG. 19F shows the effects of 4-AP, TEA, charybdotoxin and clofilium on KCNQ2+KCNQ3 current. Superimposed currents were recorded during 1 sec steps to +20 mV, from −80 mV, during the same experiment. Compounds were applied via bath perfusion in order from top to bottom. Similar results were obtained in 4 additional oocytes.

FIG. 20 shows the interaction of KCNE1 (minK) with KCNQ2+KCNQ3 currents. Families of currents from KCNE1 (FIG. 20A), KCNQ2+KCNQ3 (FIG. 20B) and KCNQ2+KCNQ3+KCNE1 (FIG. 20C) cRNA-injected oocytes elicited by 1 sec voltage steps, from a holding potential of −80 mV, to test potentials ranging from −70 to +50 mV (10 mV increments). Inset of FIG. 20A shows KCNE1 currents elicited by 5 sec voltage steps from −80 mV to potentials ranging from −30 to +50 mV (20 mV increments) in the same oocyte.

Figure 21A:
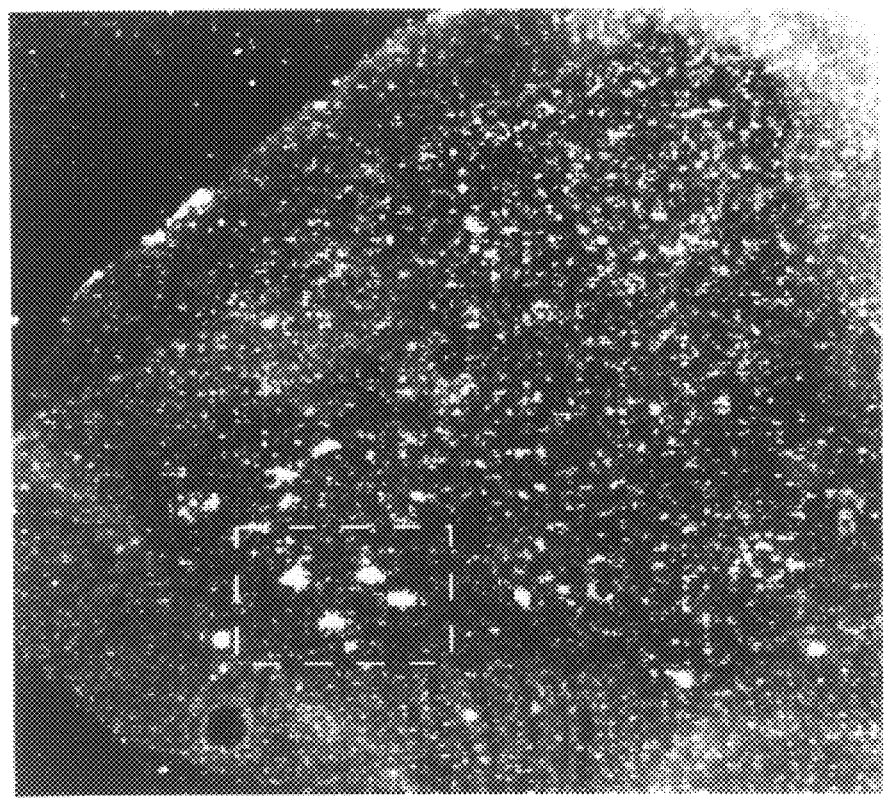
Figure 21B:
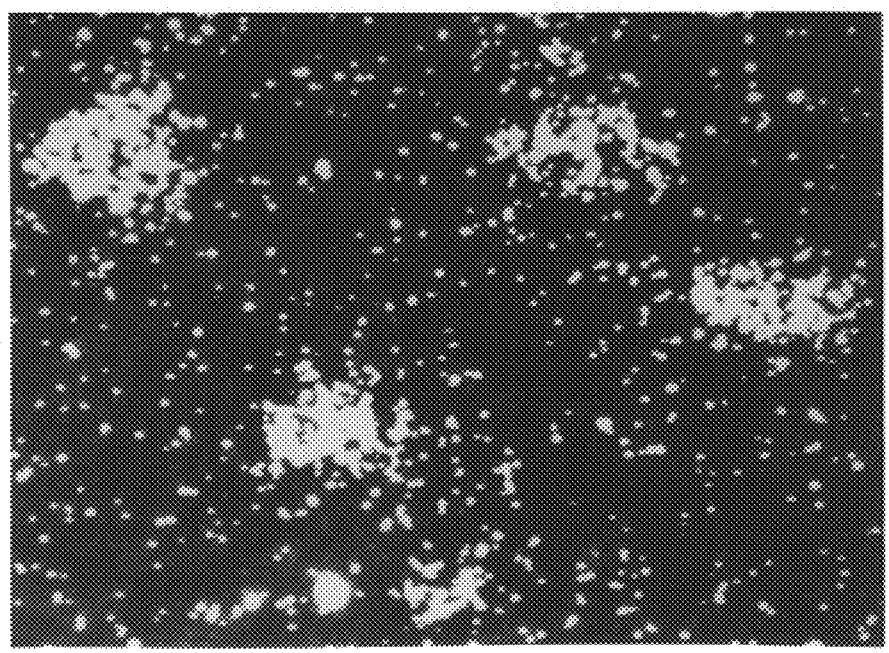

FIG. 21 is a photograph of in situ hybridization with rat KCNQ2 showing a cross section of the rat spinal cord. FIG. 21(A) is under low magnification (55×); several areas can be visualized with a relatively high signal. FIG. 21(B) is under higher magnification (322×); each high signal area is one cell and they appear by their size to be motoneurons.

Figure 22A:
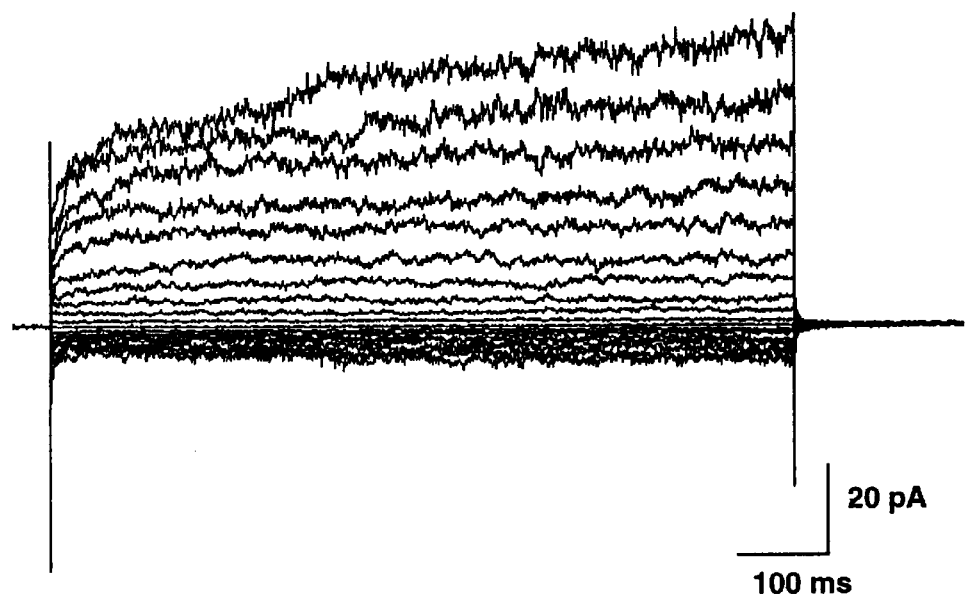
Figure 22B:
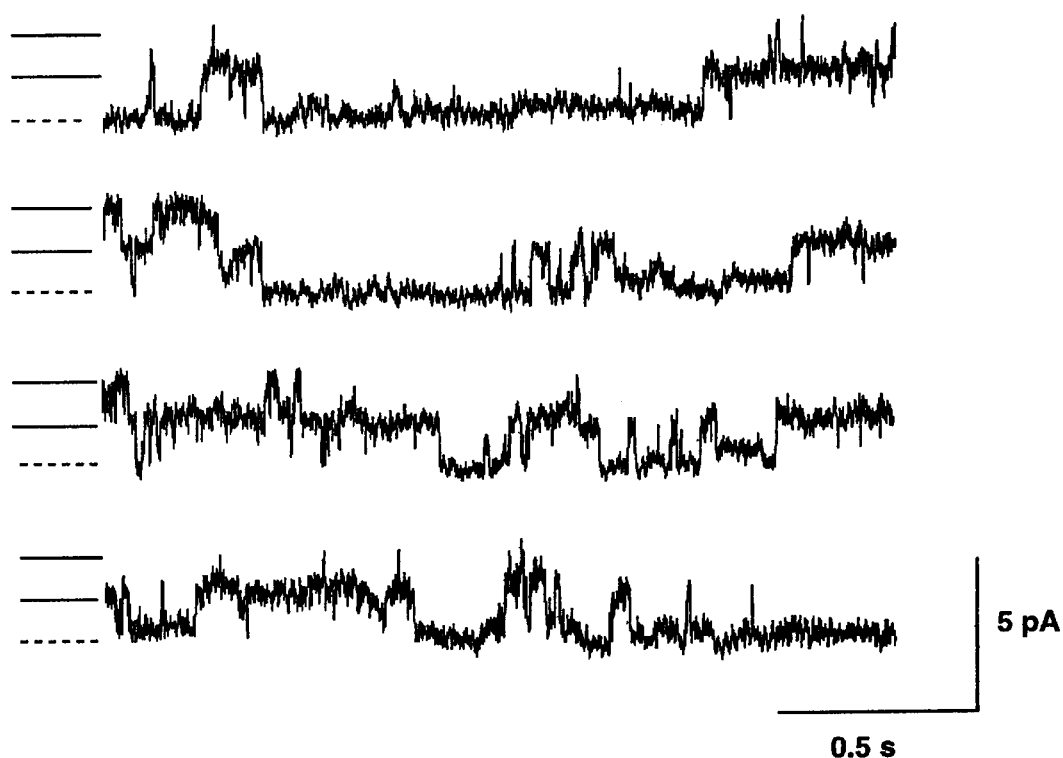

FIG. 22A shows macroscopic murine KCNQ2 current recorded from inside-out membrane patch excised from a CHO cell stably expressing murine KCNQ2. The current displays slow activation and outward rectification. FIG. 22B shows patch clamp recording of single channel currents in an excised inside-out patch from a CHO/murine KCNQ2 cell. There are at least 2 channels in the patch; single channel conductance of KCNQ2 was estimated to be between 24 and 30 pS. All recordings were made in symmetrical 140 mM $K^+$ using standard techniques.

FIG. 23 shows the nucleotide (SEQ ID NO:26) and deduced amino acid (SEQ ID NO:27) sequence of human KCNQ3 (also referred to herein as KvLR2).

DETAILED DESCRIPTION OF THE INVENTION

The following definitions apply to the terms used throughout this specification, unless otherwise defined in specific instances:

"cloning"—isolation of a particular gene from genetic material, for example a genome, genomic library, or cDNA library into a plasmid or other vector;

"KvLR protein"—a protein having at least about 70% identity with the consensus sequence (SEQ. ID. NO.:2). It may also be referred to as a "KCNQ protein", "KvLR/KCNQ protein" or "KCNQ/KvLR protein".

"KCNQ1"—the protein formerly known as KvLQT1.

"KCNQ2"—the protein formerly known as KvLR1.

"KCNQ3"—the protein formerly known as KvLR2.

"stringent conditions" (as used concerning nucleic acid hybridization)—For example, Southern blotting washed in 1×SSC and 0.1% SDS at a temperature of at least about 42° C. For additional stringent conditions, see Maniatis et al., *Molecular Cloning: A Laboratory Manual*, Cold Spring Harbor Laboratory, Cold Spring Harbor, N.Y. (1982).

"multi-copy plasmid"—a plasmid having greater than one copy present in a cell (typically 10 to 30 copies);

"Northern blotting"—a method of identifying particular RNA fragments by hybridization with a complementary nucleic acid, typically a cDNA or an oligonucleotide;

"open reading frame" or "ORF"—a DNA sequence containing a series of nucleotide triplets coding for amino acids and lacking any termination codes;

"plasmid"—cytoplasmic, autonomously replicating DNA elements found in microorganisms;

"promoter"—a region on DNA at which RNA polymerase binds and initiates transcription; and "Southern blotting"—a method of identifying particular DNA fragments by hybridization with a complementary nucleic acid, typically a cDNA or an oligonucleotide.

For definitions of other terms in this specification, see F. Sherman et al., *Laboratory Course Manual for Methods in Yeast Genetics*, Cold Spring Harbor Laboratory, Cold Spring Harbor, N.Y. (1987) and Lewin, B., *Genes IV*, Oxford University Press, Oxford (1990).

The following definitions apply to abbreviations in this specification, unless otherwise defined in specific instances:
BFNC benign familial neonatal convulsions
BLAST basic local alignment search tool
CHO Chinese hamster ovary cells
DTT dithiothreitol
DRG dorsal root ganglion
EDTA ethylene diamino tetraacetic acid
EST expressed sequence tags
GPCR G-protein-coupled receptor
ORF open reading frame
PAGE polyacrylamide gel electrophoresis
PBS phosphate buffered saline
PCR polymerase chain reaction
SDS sodium dodecyl sulfate
SSC buffer containing 150 mM NaCl, 15 m$\underline{M}$Na$_3$citrate.2 H$_2$O, pH 7.0.
TEA tetraethylammonium For additional abbreviations, see *Aldrichimica Acta*, Vol. 17, No. 1 (1984).

Use and Utility

It is believed by those skilled in the art that KCNQ proteins may be involved in neurotransmission. Persons of ordinary skill in the art can use KCNQ/KvLR proteins of the present invention to assay for modulators of KCNQs/KvLRs. KCNQ modulators would be useful in treatment of such disorders as ataxia, myokymia, seizures (e.g., epileptic seizures), Alzheimer's disease, Parkinson's disease, age-associated memory loss, learning deficiencies, motor neuron diseases, stroke, and the like.

Because KCNQ2 and KCNQ3 are nervous system-selective potassium channels, drug specificity is built into any KCNQ2/KCNQ3-specific modulator. A drug specific for KCNQ2 and/or KCNQ3 protein would thus avoid side-effects on peripheral tissues that contain potassium channels. Significantly, KCNQ2/KCNQ3-specific modulators would avoid side-effects on the heart, which contains numerous types of potassium channels.

The KCNQ nucleic acids of the present invention, or antisense nucleic acids, may be useful therapeutic or diagnostic agents. For such gene therapy, the nucleic acids may be incorporated into vectors and/or formulated as described below and in further detail in the art.

Persons skilled in the art can use the polypeptides and nucleic acids of this invention to prepare vectors, cells or cell lines, and antibodies. All of these are useful in assays for identification of KCNQ2/KCNQ3 protein modulators.

One can administer KCNQ2 and/or KCNQ3 protein modulators to various mammalian species, such as monkeys, dogs, cats, mice, rats, humans, etc. By known methods, persons skilled in the pharmaceutical art can incorporate KCNQ2/KCNQ3 protein modulators in a conventional systemic dosage form, such as a tablet, capsule, elixir or injectable formulation. The above dosage forms will also include any necessary physiologically acceptable carrier material, excipient, lubricant, buffer, antibacterial, bulking agent (such as mannitol), anti-oxidants (ascorbic acid or sodium bisulfite) or the like.

Process of Preparation

In General

This specification describes the cloning and functional expression of full-length human cDNA clones of KCNQ2 (KvLR1) and KCNQ3 (KvLR2), preferably the human KCNQ2 nucleic acid sequence (FIG. 2) as shown in SEQ ID NO:19, the human KCNQ2 amino acid sequence (FIG. 2) as shown in SEQ ID NO:20, the human KCNQ3 nucleic acid sequence (FIG. 23) as shown in SEQ ID NO:26, and the human KCNQ3 amino acid sequence (FIG. 23) as shown in SEQ ID NO:27. Also disclosed is a full-length murine cDNA clone of KCNQ2 (murine KvLR1; FIG. 10), preferably the murine KCNQ2 nucleic acid sequence as shown in SEQ ID NO:22, and the murine KCNQ2 amino acid sequence as shown in SEQ ID NO:23. Additionally, the present invention covers a rat KCNQ2 sequence (FIG. 16 and FIG. 17), preferably the rat KCNQ2 nucleic acid sequence as shown in SEQ ID NO:7, and the rat KCNQ2 amino acid sequence as shown in SEQ ID NO:8. The gating kinetics and macroscopic current properties of human, murine and rat KCNQ2 and KCNQ3 currents are similar to those of KCNQ1. However, KCNQ2 and KCNQ3 are specifically localized within the nervous system and have different pharmacological properties.

DNA clones comprising nucleotide sequences encoding the following KCNQ2 and KCNQ3 proteins of the present invention were deposited with the American Type Culture Collection ("ATCC") (10801 University Blvd., Manassas, Va. 20110-2209) on Jul. 1, 1998: human KCNQ2, ATCC Accession Number 203089 ; human KCNQ3, ATCC Accession Number 203036; and murine KCNQ2, ATCC Accession Number 203058 deposited Jul. 2, 1998. The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. 112. The sequence of the polynucleotides contained in the deposited materials, as well as the amino acid sequence of the of the polypeptides encoded thereby, are incorporated herein by reference and are controlling in the event of any conflict with any description of sequences herein. A license may be required to make, use or sell the deposited materials, and no such license is hereby granted.

Nucleic Acids

With the human KCNQ2, human KCNQ3, murine KCNQ2, and rat KCNQ2 gene sequences in hand, one skilled in the art can obtain KCNQ nucleic acids of this invention by known methods. Such methods include: (1) Southern and Northern blotting; (2) Western immunoblotting; (3) chemical synthesis; (4) synthesis by polymerase chain reaction (PCR) from primers; (5) expression cloning; and (6) subtractive cDNA cloning.

Persons skilled in the art can also modify the nucleic acids coding for the KCNQ proteins of the present invention to prepare useful mutations. For example, one may modify the sequence to provide additional restriction endonuclease recognition sites in the nucleic acid. Such mutations may be silent or may change the amino acid encoded by the mutated codon. One can prepare these modified nucleic acids, for example, by mutating the nucleic acid coding for KCNQ2 to result in deletion, substitution, insertion, inversion or addition of one or more amino acids in the encoded polypeptide. For methods of site-directed mutagenesis, see Taylor, J. W. et al. (1985), *Nucl. Acids Res.* 13, 8749–64 and Kunkel, J. A. (1985), *Proc. Na. Acad. Sc. USA* 82: 482–92. In addition, kits for site-directed mutagenesis are available from commercial vendors (e.g., BioRad Laboratories, Richmond, Calif.; Amersham Corp., Arlington Heights, Ill.). For disruption, deletion and truncation methods, see Sayers, J. R. et al. (1988), *Nucl. Acids Res.* 16: 791–800.

This invention also comprises modified nucleic acids, including (1) alternative splice exon variants; (2) allelic variants; and (3) chimeric channels in which the fusion construct comprises a KCNQ modulatory site. Such modified nucleic acids can be obtained by persons of ordinary skill in the art when armed with the present disclosure.

Expression Vectors

This invention further concerns expression vectors comprising a nucleotide sequence encoding a KCNQ protein of the present invention. Preferably, the expression vectors comprise all or a portion of the nucleic acid sequence as shown in SEQ ID NO:1, SEQ ID NO:3, SEQ ID NO:19, SEQ ID NO:5, SEQ ID NO:22, SEQ ID NO:7, SEQ ID NO:17, or SEQ ID NO:26.

Expression vectors are usually plasmids, but the invention includes other vector forms that serve equivalent functions and become known in the art subsequently hereto. A person skilled in the art might also stably integrate a sequence encoding a KCNQ protein into the chromosome of an appropriate host cell.

Expression vectors typically contain regulatory elements capable of affecting expression of a KCNQ protein. These regulatory elements can be heterologous or native KCNQ elements. Typically, a vector contains an origin of replication, a promoter, and a transcription termination sequence. The vector may also include other regulatory sequences, including mRNA stability sequences, which provide for stability of the expression product; secretory leader sequences, which provide for secretion of the expression product; environmental feedback sequences, which allow expression of the structural gene to be modulated (e.g., by the presence or absence of nutrients or other inducers in the growth medium); marking sequences, which are capable of providing phenotypic selection in transformed host cells; restriction sites, which provide sites for cleavage by restriction endonucleases; and sequences which allow expression in various types of hosts, including prokaryotes, yeasts, fungi, plants and higher eukaryotes.

An expression vector of this invention is at least capable of directing the replication, and preferably the expression, of the nucleic acids and protein of this invention. Suitable origins of replication include, for example, the Col E1, the SV40 viral and the M13 origins of replication. Suitable promoters include, for example, the cytomegalovirus promoter, the lacZ promoter, the gal10 promoter and the *Autographa californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Examples of selectable markers include neomycin, ampicillin, and hygromycin resistance and the like.

Persons skilled in the art may insert DNA encoding a KCNQ protein of the present invention into several commercially available vectors. Examples include vectors compatible with mammalian cells, such as pcDNA3 or pCEP4; baculovirus vectors such as pBlueBac; prokaryotic vectors such as pcDNA2; and yeast vectors such as pYes2. For vector modification techniques, see Sambrook et al. (1989), *Molecular Cloning: A Laboratory Manual*, Second Edition, Cold Spring Harbor Laboratory, Cold Spring Harbor, N.Y.

Host Cells

This invention additionally concerns host cells containing an expression vector that comprises a sequence encoding a KCNQ protein, preferably the KCNQ2 and/or KCNQ3 proteins of the present invention. The host cells preferably contain an expression vector which comprises all or part of the DNA sequence having the nucleotide sequence substantially as shown in SEQ ID NO:1, SEQ ID NO:3, SEQ ID NO:19, SEQ ID NO:5, SEQ ID NO:22, SEQ ID NO:7, SEQ ID NO:17 or SEQ ID NO:26, particularly the coding regions thereof. Suitable host cells include both prokaryotic cells (e.g., *E. coli* strains HB101, DH5α, XL1 Blue, Y1090 and JM101) and eukaryotic cells (e.g., *Spodoptera frugiperda* insect cells, CHO cells, COS-7 cells, HEK 293 cells, human skin fibroblasts, and *S. cerevisiae* cells).

Persons skilled in the art may introduce expression vectors into host cells by various methods known in the art.

Exemplary methods are transfection by calcium phosphate precipitation, electroporation, liposomal fusion, nuclear injection, and viral or phage infection. One may then culture the host cell under conditions permitting expression of large amounts of KCNQ protein.

One may identify such modified host cells by any of six general approaches:

(a) DNA-DNA hybridization with probes complementary to the sequence encoding KCNQ protein (Southern blotting).

(b) detection of marker gene functions, such as thymidine kinase activity, resistance to antibiotics, and the like. A marker gene can be placed in the same plasmid as the KCNQ sequence under the regulation of the same or a different promoter.

(c) detection of mRNA transcripts by hybridization assays (e.g., Northern blotting or a nuclease protection assay using a probe complementary to the RNA sequence).

(d) immunodetection of gene expression (e.g., by Western blotting with antibody to KCNQ protein).

(e) detection of potassium channel activity, such as by patch-clamp analysis, radioisotope (e.g., $^{86}$Rb) efflux, or membrane potential-sensitive reagents (e.g., Dibac from Molecular Probes International).

(f) PCR with primers homologous to expression vector sequences or sequences encoding KCNQ protein. The PCR produces a DNA fragment of predicted length, indicating incorporation of the expression system in the host cell.

Persons skilled in the art may determine DNA sequences by various known methods. See, for example, the dideoxy chain termination method in Sanger et al. (1977), *Proc. Natl. Acad. Sci. USA* 74: 5463–7 and the Maxam-Gilbert method in Maxam-Gilbert (1977), *Proc. Natl. Acad. Sci. USA* 74: 560–4.

One may use the host cells of this invention in a variety of ways that are now apparent. One may use the cells to screen for compounds that bind to or otherwise modulate or regulate the function of KCNQ protein, which would be useful for modulation, for example activation, of KCNQ2 and/or KCNQ3 protein activity; to study signal transduction mechanisms and protein-protein interactions; and to prepare KCNQ protein for the uses described below.

Not all expression vectors and DNA regulatory sequences will function equally well to express the DNA sequences of this invention. Neither will all host cells function equally well with the same expression system. However, one of ordinary skill in the art may make a selection among expression vectors, DNA regulatory sequences, and host cells using the guidance provided herein without undue experimentation and without departing from the scope of the invention.

Polypeptides

This invention further concerns polypeptides comprising all or a portion of the amino acid sequences of a KCNQ2 and/or KCNQ3 protein. The inventors prefer polypeptides comprising all or a portion of the amino acid sequences shown as in SEQ ID NO:2, SEQ ID NO:4, SEQ ID NO:20, SEQ ID NO:6, SEQ ID NO:23, SEQ ID NO:8, SEQ ID NO:18, or SEQ ID NO:27. Where a portion of the KCNQ2 and/or KCNQ3 protein is used, preferably the portion exhibits $K^+$ channel activity or can be modulated to exhibit $K^+$ channel activity. For example, and within the scope of the invention, are polypeptides that comprise all or a portion of KCNQ2 and/or KCNQ3 that may contain one or more mutations so that the protein(s) fails to exhibit $K^+$ channel activity, but that can be used to screen for compounds that will activate the protein or portion thereof.

Persons having ordinary skill in the art may prepare these polypeptides by methods known in the art. For example, one may use chemical synthesis, such as the solid phase procedure described by Houghton et al. (1985), *Proc. Natl. Acad. Sci.* 82: 5131–5. Another method is in vitro translation of mRNA. One may also produce the polypeptides in the above-described host cells, which is the preferred method. For example, one may synthesize DNA comprising all or a portion of SEQ ID NO:1, SEQ ID NO:3, SEQ ID NO:19, SEQ ID NO:5, SEQ ID NO:22, SEQ ID NO:17, or SEQ ID NO:26 by PCR as described above, insert the synthesized DNA into an expression vector, transform a host cell with the expression vector, and culture the host cell to produce the desired polypeptides.

Persons skilled in the art can isolate and purify such polypeptides by any one of several known techniques; for example, ion exchange chromatography, gel filtration chromatography and affinity chromatography. Such techniques may require modification of the protein. For example, one may add a histidine tag to the protein to enable purification on a nickel column.

Persons skilled in the art can use the polypeptides of the invention in a wide variety of ways. For example, one may use them to generate polyclonal or monoclonal antibodies. One may then use such antibodies for immunodetection (e.g., radioimmunoassay, enzyme immunoassay, or immunocytochemistry), immunopurification (e.g., affinity chromatography) of polypeptides from various sources, or immunotherapy (i.e., for potassium channel inhibition or activation).

Persons skilled in the art may make modified KCNQ polypeptides by known techniques. Such modifications may cause higher or lower activity, permit higher levels of protein production, or simplify purification of the protein. Such modifications may help identify specific KCNQ2 and/or KCNQ3 amino acids involved in binding, which in turn may help rational drug design of KCNQ2/KCNQ3 modulators. One can make amino acid substitutions based on similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine; asparagine, glutamine; serine, threonine; phenylalanine, tyrosine. All such modified polypeptides are included within the scope of the invention.

The inventors contemplate a number of other variations of the above-described polypeptides. Such variations include salts and esters of the polypeptides, as well as precursors of the aforementioned polypeptides (e.g., having N-terminal substituents such as methionine, N-formylmethionine and leader sequences). The invention includes all such variations.

Method for Detecting Nucleic Acids

The present invention further concerns a method for detecting nucleic acids encoding KCNQ protein. In this method, a person of ordinary skill in the art (a) contacts nucleic acids of unknown sequence with a nucleic acid having a sequence complementary to a known coding sequence (e.g., a sequence of at least about 10 nucleotides from, e.g., SEQ ID NO:1, SEQ ID NO:3, SEQ ID NO:19, SEQ ID NO:5, SEQ ID NO:22, SEQ ID NO:7, SEQ ID NO:17, or SEQ ID NO:26, particularly the coding regions thereof), wherein the latter nucleic acid has a detectable marker; and (b) determines the presence of marker bound to any of the nucleic acids of unknown sequence. The presence of bound marker indicates the presence of the desired nucleic acids. One can apply this method to detect KCNQ nucleic acids from other tissues (which may have different regulatory elements) and nucleic acids from other species (e.g., monkey).

Persons of ordinary skill in the art generally know how to obtain nucleic acids to be analyzed in this method. For genomic DNA, one can rapidly freeze tissue, crush the tissue into readily digestible pieces, and incubate the crushed tissue in proteinase K and SDS to degrade most cellular proteins. One can then deproteinize the genomic DNA by successive phenol/chloroform/isoamyl alcohol extractions, recover DNA by ethanol precipitation, dry it and resuspend it in buffer. For RNA, one can lyse cultured cells in 4M guanidinium solution, draw the lysate through a 20-gauge needle, pellet the RNA through a cesium chloride step gradient, and remove the supernatant. The pellet should contain purified RNA.

The detectable marker may be a radioactive ion linked to one of the nucleotides of the complementary nucleic acid. Common radioactive labels are $^{32}P$ and $^{35}S$, although one may also use other labels such as biotin. Persons skilled in the art are aware of various methods to attach the labels to the complementary nucleic acid (e.g., the random primer method for attachment of $^{32}P$ or $^{35}S$).

Persons of ordinary skill in the art generally know how to carry out such a method of detecting nucleic acids. For example, one may perform a Southern or northern blot using a radiolabeled KCNQ complementary oligonucleotide probe. One can then detect hybridization by autoradiography. Depending on the marker, one may also use other detection methods (e.g., spectrophotometry).

Methods for Detecting KCNQ2/KCNO3 Protein Modulators

This invention further concerns methods for detecting modulators of the KCNQ2 and/or KCNQ3 proteins of the present invention. A screen for KCNQ protein modulators entails detecting binding of molecules (e.g., polypeptides, natural products, synthetic compounds) in cells expressing KCNQ protein.

Cloning and sequencing of KCNQ protein enables construction of cells useful in screening for natural products and synthetic compounds that bind to and/or modulate KCNQ protein activity. A process for detecting KCNQ protein modulators requires transforming a suitable vector into compatible host cells as described previously herein. One treats such transformed cells with test substances (e.g., synthetic compounds or natural products), and then measures activity in the presence and absence of the test substance.

Gene Therapy

Persons skilled in the art can also use sense and antisense nucleic acid molecules as therapeutic agents for KCNQ-related indications. One may construct vectors that direct the synthesis of the desired DNA or RNA or formulate the nucleic acid as described in the art.

Several references describe the usefulness of antisense molecule. See Toulme and Helene (1988), *Gene* 72: 51–8; Inouye (1988), *Gene,* 72: 25–34; Uhlmann and Peyman (1990), *Chemical Reviews* 90: 543–584; *Biotechnology Newswatch* (Jan. 15, 1996), p. 4; Robertson, *Nature Biotechnology* 15: 209 (1997); Gibbons and Dzau (1996), *Science* 272: 689–93. One can design them based on genomic DNA and/or cDNA, 5' and 3' flanking control regions, other flanking sequences, intron sequences, and nonclassic Watson and Crick base pairing sequences used in formation of triplex DNA. Such antisense molecules include antisense oligodeoxyribonucleotides, oligoribonucleotides, oligonucleotide analogues, and the like, and may comprise at least about 15 to 25 bases.

Antisense molecules may bind noncovalently or covalently to the KCNQ DNA or RNA. Such binding could, for example, cleave or facilitate cleavage of KCNQ DNA or RNA, increase degradation of nuclear or cytoplasmic mRNA, or inhibit transcription, translation, binding of trans-activating factors, or pre-mRNA splicing or processing. Antisense molecules may also contain additional functionalities that increase stability, transport into and out of cells, binding affinity, cleavage of the target molecule, and the like. All of these effects would decrease expression of KCNQ protein and thus make the antisense molecules useful as KCNQ protein modulators.

DETAILED DESCRIPTION OF PREFERRED EMBODIMENTS

Human KCNQ2 and KCNQ3

Genetic Properties

Figure 1:
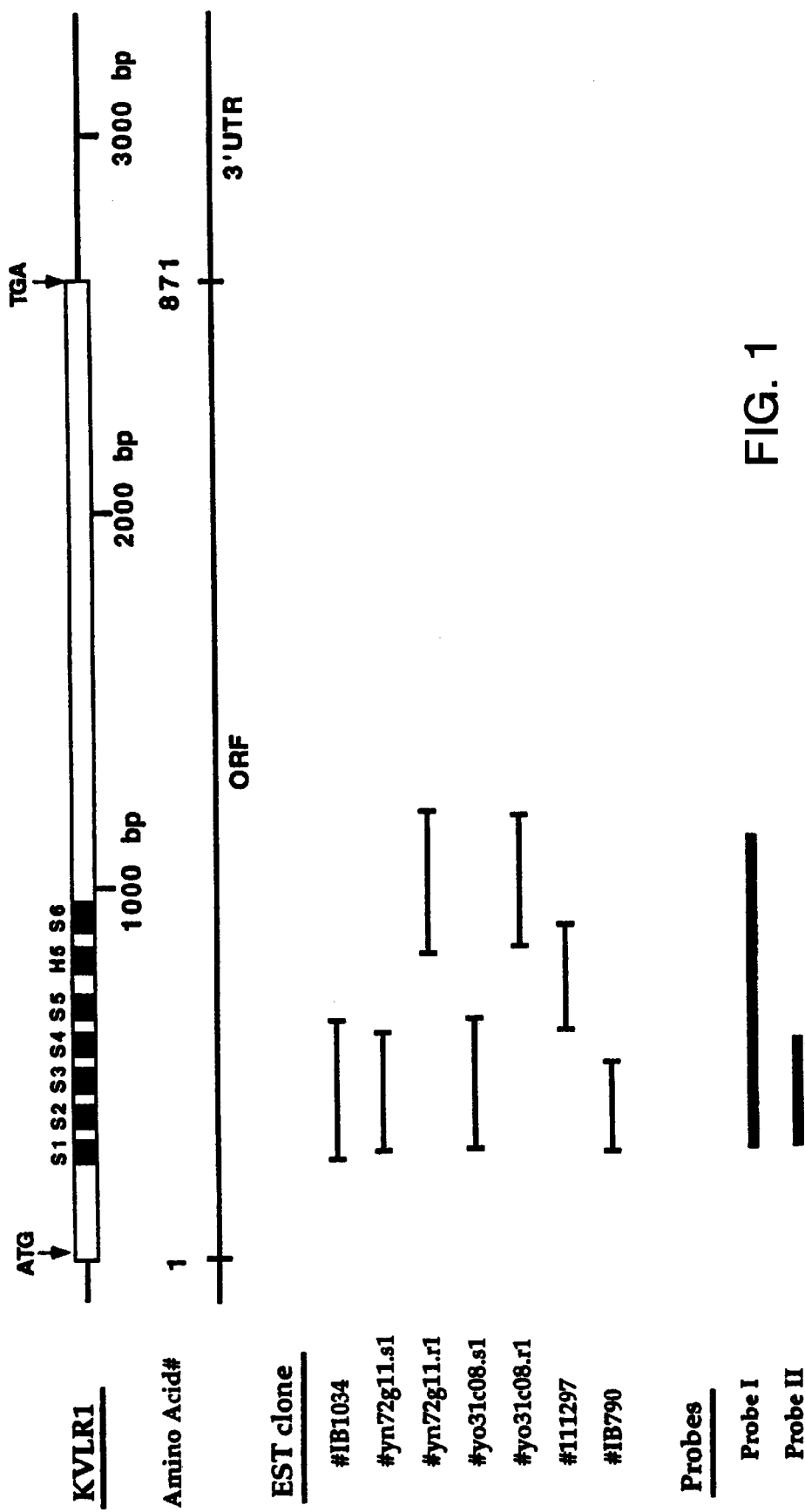
FIG. 1 shows isolation of a full-length human KCNQ2/KvLRI cDNA. A full-length human KCNQ2/KvLR1 cDNA was derived from two overlapping cDNA clones. "S1" through "S6" signify transmembrane domains 1 through 6; "H5" signifies the pore-forming domain (this domain is also referred to herein as the "P" domain); ORF, the open-reading frame; 3' UTR, the 3' untranslated regions. The locations of various EST clones and probes also are shown. (The figure is not drawn to scale.)

KCNQ1-Related (KCNQ2/KCNQ3) expressed sequence tags (ESTs) were discovered by a GCG BLAST search of the GenBank database with KCNQ1 sequence. Primers, derived from the consensus sequences of EST clones, were used to amplify human brain-derived cDNA and 877 bp and 325 bp fragments were isolated for KCNQ2 and KCNQ3, respectively. (FIG. 1, probe I). To obtain full-length cDNA sequences of both genes, we employed 5'RACE PCR, screening of cDNA libraries, and Gene Trapper techniques. The composite full-length cDNAs of KCNQ2 (SEQ ID NO:19) and KCNQ3 (SEQ ID NO:26) contain an open reading frame (ORF) encoding an 871 (SEQ ID NO:20) and 854 (SEQ ID NO:27) amino acid polypeptide, respectively (FIG. 2 and FIG. 23). DNA sequence analysis and conceptual translation of both cDNAs reveals that they encode proteins with the structural features of a voltage-gated potassium channel and are most closely related to KCNQ1. Sanguinetti et al. (1996), *Nature* 384: 80–83; Yang et al. (1997), *Proc. Natl. Acad. Sci.* USA 94:4017–2. KCNQ2 exhibits a high degree of sequence similarity with KCNQ3 (≈70%), indicating that they belong to the same subfamily. Both proteins have a longer C-terminal domain (200 amino acids) than KCNQ1. The initiation codon for KCNQ2 is flanked by a consensus ribosome binding site (i.e., Kozak) ACCATGG (FIG. 2) (resides 58–64 of SEQ ID NO:19).

At the amino acid level, sequence analysis reveals that KCNQ2/KvLR1 contains the GYG (i.e., Gly-Tyr-Gly) potassium channel pore "signature sequence" and, therefore, is likely to encode a potassium-selective channel. A comparison of KCNQ2 and KCNQ1 (KvLQT1) reveals that the amino acid sequence identity is approximately 60% in the transmembrane and pore regions (FIG. 3). KCNQ3 exhibits about the same degree of identity (about 56%) with KCNQ1 as KCNQ2 in the transmembrane and pore regions (FIG. 4). The identity in the amino-terminal and carboxy-terminal domain is much less compared to the central conserved regions (FIG. 3). Such findings suggest that KCNQ2/KvLR1 and KCNQ3/KvLR2 are additional members of the KCNQ1/KvLQT1 family of ion channels.

KCNQ2- and KCNQ3-specific transcripts are detectable only in human brain (FIG. 5). This expression pattern is distinct from KCNQ1/KvLQT1, which is expressed strongly in human heart and pancreas as revealed by Northern blot analysis. Sanguinetti et al. (1996) *Nature* 384: 80–83; Yang et al. 1. (1997), *Proc. Natl. Acad. Sci. USA* 94:4017–2. Expression of human KCNQ2/KvLR1 is high in the hippocampus, caudate nucleus, and amygdala; moderate in the thalamus; and weak in the subthalamic nucleus, substantia nigra and corpus callosum (FIG. 5). A separate Northern blot demonstrates that expression of human KCNQ2/KvLR1 is high in the cerebral cortex; is moderate in the putamen, temporal lobe, frontal lobe, occipital pole and cerebellum; and is low in the medulla and spinal cord (FIG. 5). KCNQ3 exhibits a nearly identical expression pattern in the brain (FIG. 5). In order to characterize further the cell types that express KCNQ2/KvLR1, a murine-specific KCNQ2/KvLR1 cDNA fragment was isolated and used as an in situ hybridization probe. The result (FIG. 9) shows that KCNQ2/KvLR1 is expressed in the mouse hippocampus and dentate gyrus, areas that are important in learning and memory.

Electrophysiological Properties

The full-length human KCNQ2 and KCNQ3 cDNAs were subcloned into a Xenopus expression vector and cRNA was generated by in vitro transcription. The properties of the channels encoded by human KCNQ2 and KCNQ3 were investigated by expressing the transcribed cRNA in Xenopus oocytes. FIG. 6 compares currents recorded from oocytes that were injected 5 days earlier with either water (FIG. 6A) or 14 ng of human KCNQ2/KvLR1 cRNA (FIG. 6B). Oocytes injected with human KCNQ2/KvLR1 cRNA exhibited outward currents that activated at potentials positive to −60 mV and had a maximal amplitude of 1 $\mu$A at +40 mV. Similar currents were never observed in water-injected control oocytes and small leak or endogenous currents recorded in control oocytes never exceeded 0.15 mA at +40 mV. The human KCNQ2/KvLR1 currents exhibited a rapidly activating delayed rectifier current phenotype very similar to hKCNQ1/KvLQT1 current. Barhanin et al. (1996) *Nature* 384: 78–80; Sanguinetti et al. (1996), *Nature* 384: 80–83;; Yang et al. (1997) *Proc. Natl. Acad. Sci. USA* 94:4017–2. KCNQ2/KvLR1 current rectified weakly at positive voltages.

Although the macroscopic KCNQ2/KvLR1 and KCNQ1/KvLQT1 currents are similar, KCNQ2/KvLR1 tail currents lack the "hook" observed with KCNQ1/KvLQT1 tail current. FIG. 6C shows the peak current-voltage (IV) relationship for oocytes expressing KCNQ2/KvLR1 (n=12). The K$^+$ selectivity of the expressed current was examined by investigation of tail current reversal potentials in bath solutions containing 2, 10, 40 and 98 mM K$^+$. Reversal potentials closely followed the Nernst potential for K$^+$ revealing a K$^+$-selective channel (n=6; FIG. 6D). The reversal potential for KCNQ2/KvLR1 current shifted by 52 mV per 10-fold change in external K$^+$. The dashed line has a slope predicted from the Nernst equation for a perfectly selective K$^+$ channel.

Figure 18A:
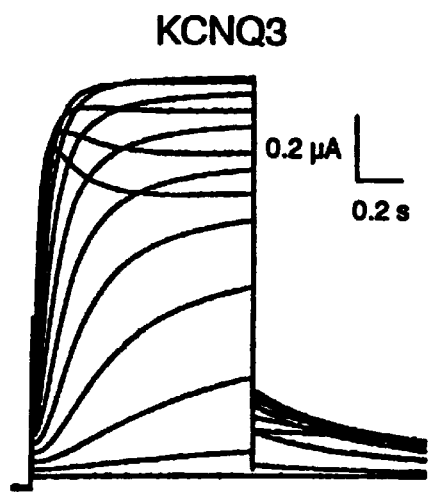
Figure 18B:
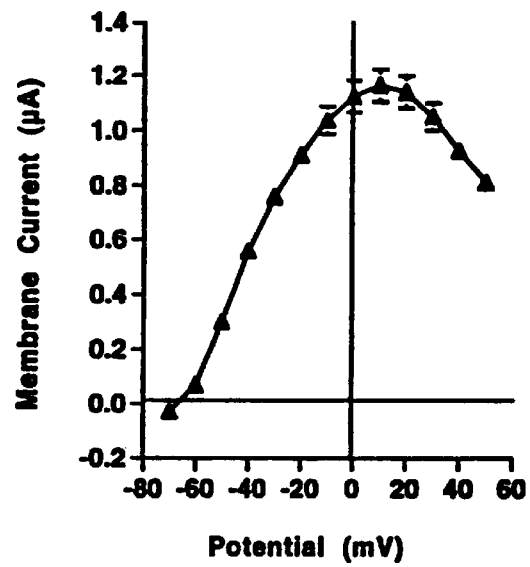
Figure 18C:
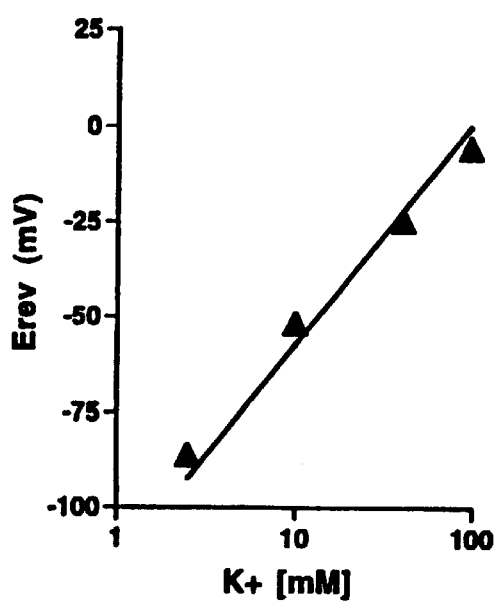

A family of currents elicited by depolarizing voltage steps in an oocyte injected with KCNQ3 cRNA are shown in FIG. 18A. The currents activate at potentials positive to −70 mV and rectify inwardly at potentials greater than 0 mV, as is obvious from the IV relationship (FIG. 18B). The KCNQ3 reversal potential shifted 49 mV per 10-fold change in external K$^+$ (FIG. 18C). Thus, although still predominantly selective for K$^+$, KCNQ3 is slightly less K$^+$-selective than KCNQ2.

Co-expression of KCNE1 (KCNE1 is also known as "minK" or "Isk") with KCNQ1/KvLQT1 dramatically alters the amplitude and gating kinetics of KCNQ1/KvLQT1 current. Barhanin et al. (1996) *Nature* 384: 78–80; Sanguinetti et al. (1996), *Nature* 384: 80–83;; Yang et al. (1997) *Proc. Natl. Acad. Sci. USA* 94:4017–2. MinK is a polypeptide thought to encode or regulate a K$^+$ channel. Folander et al. (1990) *Proc. Natl. Acad. Sci. USA* 87: 2975–2979; Varnum et al. (1993) *Proc. Natl. Acad. Sci. USA* 90: 11528–11532; Ben-Efraim et al. (1996) *J. Biol. Chem.* 271: 8768–8771. These studies suggest that minK and KCNQ1/KvLQT1 co-assemble to form the K$^+$ channel underlying the slow delayed rectifier current in heart. A similar association between minK and KCNQ2/KvLR1 was tested. Coexpression of KCNE1 with KCNQ2/KvLR1 had little effect on the KCNQ2/KvLR1 current in oocytes, and separate currents carried by KCNQ1/KvLQT1 and KCNQ2/KvLR1 channels could be delineated in oocytes co-injected with minK and KCNQ2/KvLR1 using selective inhibitors for each of the channels. Thus, KCNQ2/KvLR1 interacts differently with KCNE1 than does KCNQ1/KvLQT1. Different KCNQ members may functionally interact with proteins structurally similar to KCNE1.

Pharmacological Properties

Figure 7:
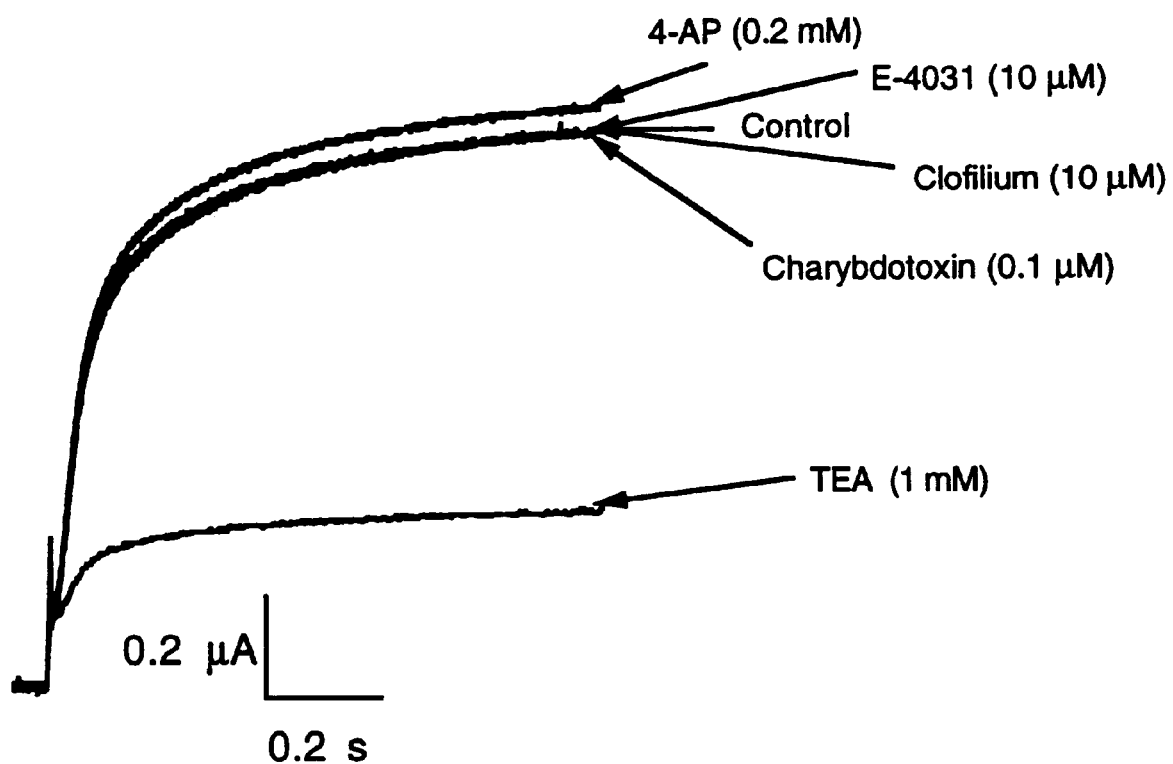
FIG. 7 shows pharmacologic characterization of KCNQ2/KvLR1 currents in Xenopus oocytes. In particular, this figure shows effects of E-4031, 4-AP, TEA, charybdotoxin and clofilium on human KCNQ2/KvLR1 current. Superimposed currents were recorded during 1 second steps to +30 mV, from −80 mV, during the same experiment. Compounds were applied via bath perfusion in order from top to bottom. The bath was perfused with control solution for 5 minutes, or until effects reversed completely, between compounds. Similar results were obtained in three additional oocytes.

Inhibitors of various potassium channels present in brain and other tissues were used to investigate the pharmacology of KCNQ2/KvLR1. The effects of 0.2 mM of 4-aminopyridine (4-AP), 10 $\mu$M E-4031, 10 $\mu$M clofilium, 0.1 mM of charybdotoxin, and 1 mM tetraethylammonium (TEA) on KCNQ2/KvLR1 currents recorded from a single oocyte are shown in FIG. 7. Each of these compounds was also tested alone in individual oocytes and the effects of each agent were no different.

Charybdotoxin is a scorpion venom protein that inhibits a variety of Ca$^{2+}$-activated and voltage-dependent K$^+$ channels. Miller et al. (1985), *Nature* 313: 316–8; Sugg ct al. (1990), *J. Biol. Chem.* 265: 18745–8. Charybdotoxin did not inhibit the KCNQ2/KvLR1 current at the concentration tested. This toxin also had no effect on KCNQ1/KvLQT1.

E-4031 (10 mM) is a selective inhibitor of I$_{Kr}$. Sanguinetti et al. (1990) *J. Gen. Physiol.* 96: 195–215). 4-AP (0.2 mM) is an inhibitor of Shaker-type K$^+$ channels. Deal et al. (1996) *Physiol. Rev.* 76: 49–67. Neither E-4031 nor 4-AP produced significant effects on KCNQ2/KvLR1 current. Similarly, both reagents do not inhibit KCNQ1/KvLQ1 currents. Yang et al. (1997), *Proc. Natl. Acad. Sci. USA* 94:4017–21.

TEA is a weak inhibitor of KCNQ1/KvLQT1 whereas clofilium is a strong inhibitor of KCNQ1/KvLQT1. Yang et al. (1997), *Proc. Natl. Acad. Sci. USA* 94:. Clofilium also inhibits cardiac I$_{Kr}$ and I$_{KS}$ Arena et al. (1988), *Molecular Pharmacology* 34: 60–66; Colatsky et al. (1990), *Circulation* 82: 2235–42. For KCNQ2/KvLR1, in contrast, clofilium had little effect whereas TEA inhibited the current by over 85% at a concentration of 1 mM.

Figure 18D:
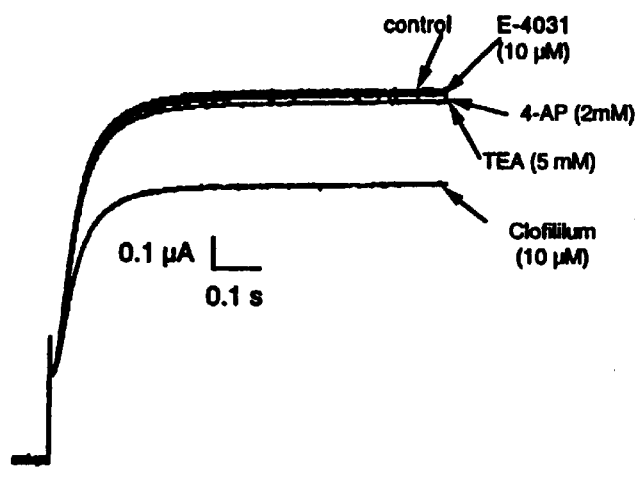

The pharmacology of KCNQ3 was significantly different than that of KCNQ2 (FIG. 18D). Clofilium (10 $\mu$M) reduced KCNQ3 current by 30% from control but had little effect on KCNQ2. TEA, which strongly inhibited KCNQ2 at 1 mM, produced little inhibition of KCNQ3 at 5 mM. CTX (100 nM), 4-AP (2 mM) and E-4031 (10 $\mu$M) also had no effect on KCNQ3 current.

As can be seen from these results, the pharmacological properties of KCNQ3/KvLR2, KCNQ2/KvLR1 and KCNQ1/KvLQT1 are quite different.

KCNQ2 and KCNO3 Functionally Interact

Figures 19A, 19B:
Figure 19C:
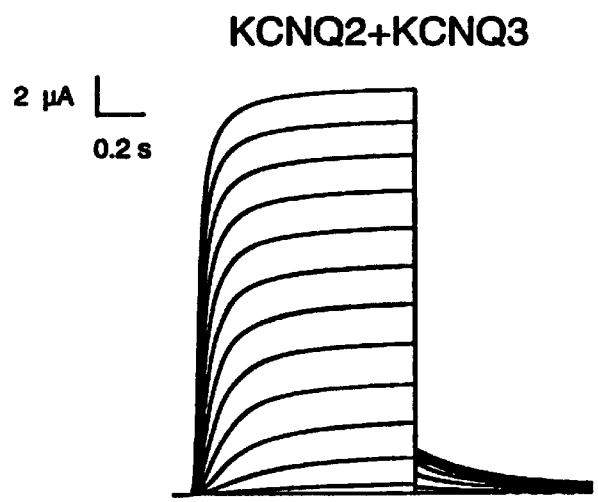
Figure 19D:
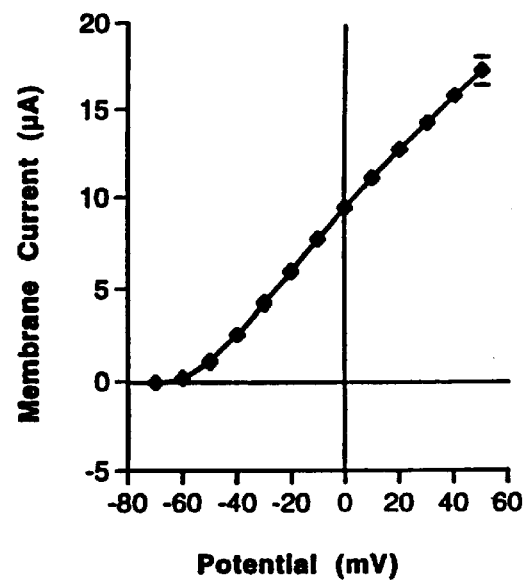
Figure 19E:
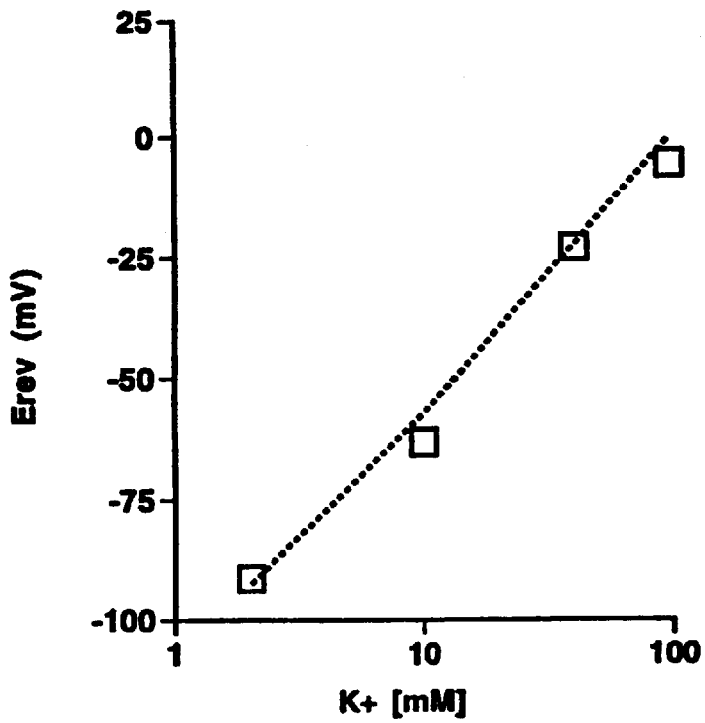
Figure 19F:
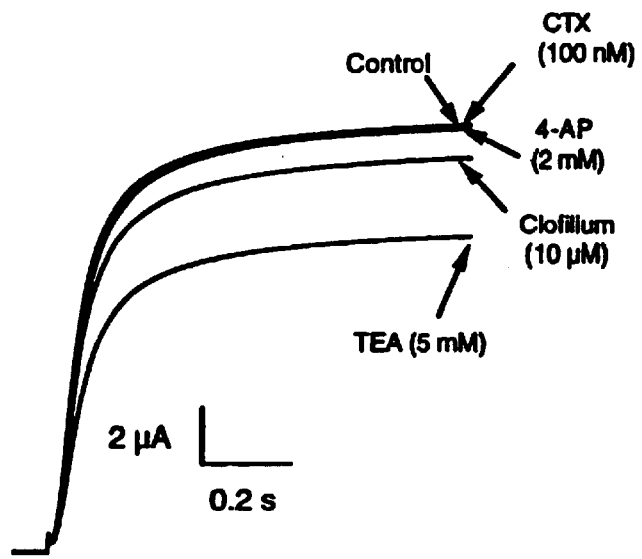

The overlapping expression pattern of KCNQ2 and KCNQ3 in different brain regions (FIG. 5), prompted us to test for functional interaction between the two channels. Families of currents elicited by depolarizing voltage steps in oocytes injected with KCNQ2 and KCNQ3 alone and together are shown in FIG. 19A through FIG. 19C. Current amplitudes recorded from oocytes co-expressing the two channels were 15-fold greater than in oocytes injected with each of the channels individually. Peak current amplitudes at +30 mV for KCNQ2, KCNQ3 and KCNQ2+KCNQ3 were 0.98±0.09 (n=6), 0.98±0.06 (n=5) and 14.2±0.62 µM (n=6), respectively. Quantitatively similar results were obtained in 3 separate batches of oocytes. The IV relationship shows that KCNQ2+KCNQ3 currents activated at potentials positive to −60 mV and did not rectify, unlike KCNQ2 and particularly KCNQ3, at positive voltages (FIG. 19D). The reversal potential of tail currents shifted by 57 mV per 10-fold change in external $K^+$ indicating that KCNQ2+KCNQ3 is nearly perfectly selective for $K^+$ (FIG. 19E). KCNQ2+KCNQ3 current is weakly sensitive to inhibition by 5 mM TEA and 10 µM clofilium but not to 100 nM CTX or 2 mM 4-AP (FIG. 19F). E-4031 (10 µM) also did not inhibit KCNQ2+KCNQ3 current (not shown). These results suggest strongly that KCNQ2+KCNQ3 interact to form a channel with properties distinct from either KCNQ2 or KCNQ3 channels alone.

KCNE1 Interacts With KCNQ2+KCNO3 Channels

The β subunit KCNE1 dramatically alters the amplitude and gating kinetics of the KCNQ1 channel. Barhanin et al. (1996) *Nature* 384: 78–80; Sanguinetti et al. (1996), *Nature* 384: 80–83; Yang et al. (1997) *Proc. Natl. Acad. Sci. USA* 94:4017–2; Romey et al. (1997) *J. Biol. Chem.* 272:16713–16716. Because KCNQ2 and KCNQ3 are members of the same $K^+$ channel subfamily, we tested for an interaction between KCNE1 and KCNQ2+KCNQ3 channels. FIG. 20 shows currents elicited by 1 sec depolarizing voltage steps in oocytes expressing KCNE1 alone (FIG. 20A), KCNQ2+KCNQ3 (FIG. 20B), and KCNQ2+KCNQ3+KCNE1 (FIG. 20C). KCNE1 significantly attenuated KCNQ2+KCNQ3 current amplitude and slowed gating kinetics. Peak current amplitude at +30 mV was reduced by 62±6.0 % (n=6) in oocytes co-expressing KCNE1. Activating currents were fitted to a bi-exponential function to determine fast and slow time constants of activation. Fast and slow time constants for activation of KCNQ2+KCNQ3 current at +10 mV were 50.1±3.4 (n=6) and 239.3±17.5 ms (n=6), respectively; these were shifted to 124.7±8.8 (n=5) and 680.7±71.4 ms (n=6) when KNCEI was injected together with KCNQ2+KCNQ3. Similar results were obtained in more than 15 oocytes from each group in this and two additional batches of oocytes. KCNE1 currents appear absent because of the duration (1 sec) of the voltage steps used and the scale at which the currents are shown. However, as shown clearly in the inset in FIG. 20A, 5 sec voltage steps elicited typical KCNE1 currents in the same oocyte. The effect of KCNE1 on gating kinetics is similar for KCNQ1 and KCNQ2+KCNQ3 channels. In contrast, KCNE1 augments KCNQ1 current but inhibits KCNQ2+KCNQ3.

The results explain why mutations in either of two unlinked $K^+$-channel encoding genes yield the same phenotype. BFNC-associated mutations in either KCNQ2 or KCNQ3 could cause a profound reduction in KCNQ2+KCNQ3 current amplitude. One study has shown that a BFNC-causing mutation resulting in an nonfunctional, truncated KCNQ2 protein, failed to produce a dominant-negative inhibition of wild-type KCNQ2 channels expressed in oocytes. Biervert et al. (1998), *Science* 279:403–406. The present invention, demonstrating a synergistic interaction between KCNQ2 and KCNQ3, may provide a likely explanation for this finding. That is, mutations in KCNQ2 may only produce dominant-negative effects when co-expressed with wild-type KCNQ3 channels, and vice versa.

Molecular Genetics

Recent advances in molecular genetics has allowed us to correlate potassium channels with diseases in the nervous system. Most recently, and as discussed above, BFNC, a class of idiopathic generalized epilepsy, was recently linked to mutations in KCNQ2 and KCNQ3. Biervert et al., supra; Charlier et al., supra; and Singh et al., supra. The identification and expression of human KCNQ2 and hum an KCNQ3 will allow us to investigate further correlations with BFNC and other potential human disease. The present invention will now permit those skilled in the art to identify modulators, e.g., activators, of KCNQ2 and/or KCNQ3. Modulators of KCNQ2 and/or KCNQ3 may provide opportunity for treatment of disease, such as BFNC. Additionally, because human KCNQ2 and KCNQ3 are expressed highly in areas associated with learning and memory, modulators of KCNQ2 and/or KCNQ3 may also provide opportunity for pharmacological treatment of the memory loss associated with advanced age, Parkinson's disease or Alzheimer's disease.

Murine KvLR1

Starting with a brain expressed sequence tag (EST, public domain database) 15 similar to the Kv Q LQTI gene, a novel potassium channel gene was cloned from a mouse brain library and functionally expressed. FIG. 10A through FIG. 10D shows the murine KCNQ2/KvLR1 gene (SEQ ID NO:22) encoding for a protein of 722 amino acids (SEQ ID NO:23) and a calculated molecular weight of 80.4 kDa. Hydropathy analysis (FIG. 10E) illustrates the computer-generated topology of KvLR1 to have 6 membrane spanning domains and a pore domain typical of voltage-gated potassium channels.

The amino acid alignment of the murine KCNQ2/KvLR1 channel with the murine KCNQ1/KvLQT1 channel is shown in FIG. 11. Overall, there is 40% identity between the two channels with 62.5% identity within the spanning and pore domains. Phylogenetic analysis suggests that the murine KCNQ2/KvLR1 gene to be a member of the KCNQ1/KvLQT1 gene family and to be distantly related to the HERG gene and other voltage-gated family members. Signature amino acid sequences characteristic of voltage-gated potassium channels are present within murine KCNQ2/KvLR1; a repeating arginine pattern is seen within the S4 spanning domain known as the voltage sensor, and a GYG sequence within the pore region. Further analysis of several 3'RACE clones indicate diversity past the S6 membrane spanning domain. To date, two alternative splice exons, A SEQ ID NO:13) and B (SEQ ID NO:14) have been identified, the amino acid sequences of which are shown in FIG. 12.

To determine tissue distribution of murine KCNQ2/KvLR1, a northern blot was performed with a probe from the murine KCNQ2/KvLR1 channel that did not contain the pore or voltage sensor regions. This sequence of the gene avoids possible cross-reactivity with other channels. The results, shown in FIG. 13, indicate a highly abundant 8.2 kb message found only in the brain and not observed in peripheral tissues. Although not absolute, longer exposures of the northern blot did not indicate the presence of the message in the peripheral tissues indicated in FIG. 5.

To obtain higher resolution of message localization within the brain, in situ hybridization was performed. Positive hybridization signal with an antisense riboprobe specific for a nonconserved region of the KCNQ2/KvLR1 gene is observed with a broad distribution throughout much of the rat brain. The mouse probe was 99% identical to the rat sequence. Robust signal, however, is observed with a more limited distribution in the following regions: piriform cortex, supraoptic nucleus, amygdala, hippocampus, including the CA1, 2, and 3 regions and the dentate gyrus, MO5 (motor nucleus of the brain stem trigeminal), facial nucleus, hypoglossal nucleus, inferior olivary nuclei, deep cerebellar nuclei, gigantocellular nuclei, lateral and medial vestibular nuclei, motor neurons of the spinal cord, and sensory neurons of the dorsal root ganglion. Moderate levels of hybridization signal are also observed in the cortex, septum, striatum, hypothalamus, thalamus, medial habenula, substantia nigra compacta, mammillary nuclei, lateral and medial geniculate, interfasicular nucleus, purkinje and granule cells of the cerebellum, parabrachial nuclei, dorsal and ventral cochlear nuclei, and other brain stem nuclei. A composite view of three regions is shown in FIG. 14.

To test for functional expression, cRNA was prepared from the murine KCNQ2/KvLR1 gene and injected into Xenopus oocytes. In a two-electrode voltage clamp, a family of outward currents were generated in murine KCNQ2/KvLR1 cRNA-injected oocytes (n>20). After a minimum of 48 hours, currents qualitatively and quantitatively different than native currents generated with identical protocols in ater injected or uninjected control cells (representing $Ca^{2+}$-activated chloride currents and other native currents) (FIG. 15). The murine KCNQ2/KvLR1-mediated currents were blocked by 1 mM TEA. Similar currents were obtained from CHO cells stably expressing murine KCNQ2 and recorded using patch-clamp techniques. Single channel conductances were estimated to be 24–30 pS in symmetrical 140 mM potassium. (FIG. 22).

To determine if murine KCNQ2/KvLR1 has similar pharmacology to $I_{Ks}$ and $I_{Kr}$ currents in cardiac myocytes, clofilium was tested on oocytes expressing murine KCNQ2. At 20 μM, clofilium was shown to partially block the murine KCNQ2-mediated currents. Other specific $K^+$ channel blocking toxins, including iberiotoxin, α-dendrotoxin and charybdotoxin, had no significant effect on murine KCNQ2-mediated currents.

MATERIALS AND METHODS

Human KCNO2
Molecular Cloning and Expression of Human KCNQ2 (Human KVLR1) and Human KCNQ3 (Human KvLR2)

5'RACE PCR was performed by amplifying human brain or fetal brain cDNA libraries or Marathon-Ready cDNAs (Clontech) using primers derived from the KvLQT1-related EST sequences (EST# yn72g11, yo31c08, ys93a07 (sequences can be found in Genbank database)) (FIG. 1). PCR products were gel-purified, subcloned and sequenced. Random-primed $^{32}$P-labelled DNA probes containing specific regions of KCNQ2 or KCNQ3 sequence were used for screening of cDNA libraries and Northern blot analysis using standard protocol. For example, KCNQ2 Probe I (FIG. 1) was used for Northern blot analysis; Probe II (FIG. 1) was used for screening human brain cDNA libraries according to standard protocols.

The Gene Trapper experiment was performed using the protocol as described in the Manufacturer's manual (LifeTechnologies). The composite full-length human KCNQ2 and human KCNQ3 cDNA clones were obtained by restriction enzyme digestion and ligation of overlapping cDNA clones. The full-length cDNAs were subcloned into a Xenopus expression vector, derived from pSP64T plasmid. Capped cRNA for microinjection was synthesized using mMESSAGE mMACHINE Kit (Ambion).

Figure 9A:
FIG. 9A is a dark-field photograph from a coronal section through an adult mouse brain hybridized with a radiolabeled antisense KCNQ2/KvLR1 probe, showing KCNQ2/KvLR1 transcripts in the pyramidal cell layers of the hippocampus. Lower levels of expression were detected in the granular cell layer of the dentate gyrus.
Figure 9B:
FIG. 9B is a dark-field photograph from a similar region as shown in FIG. 9A, but hybridized with a sense probe; little KvLR1-specific expression was detected with this probe. Magnification: 125× for both FIG. 9A and FIG. 9B.
Figure 10E:
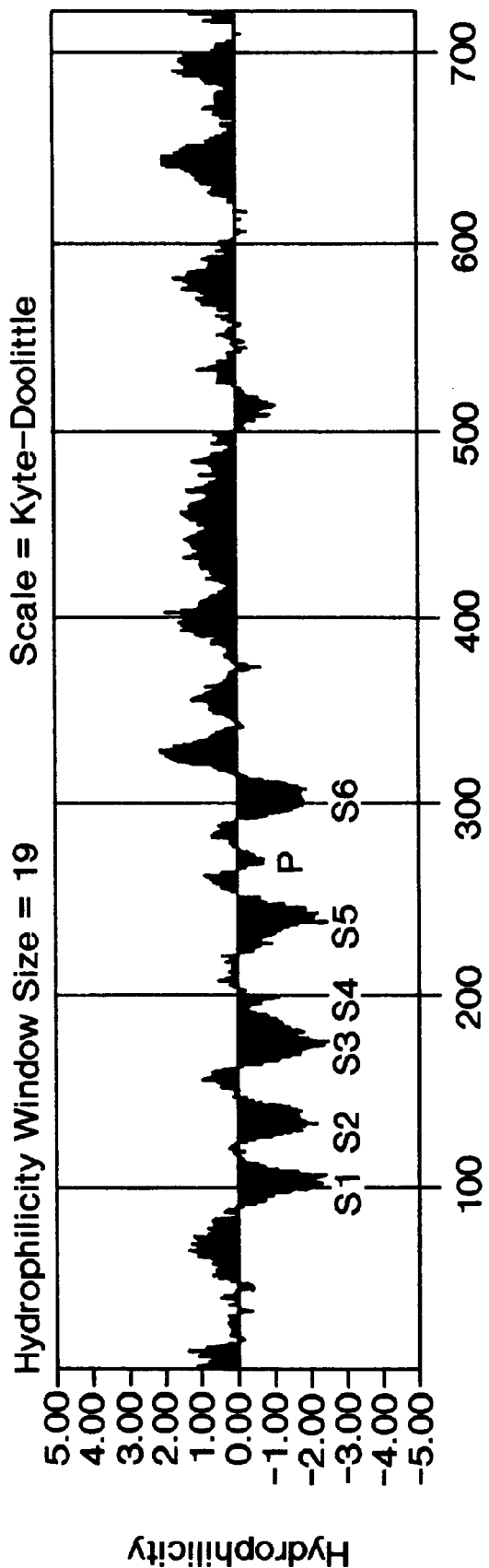

For detection of expression of KCNQ2 as shown in FIGS. 9A and 9B, tissue processing, histological analyses and in situ hybridization analyses were performed essentially as described in Fagan et al. (1996), *J. Neurosci.* 16 (19): 6208–18.

Electrophysiological and Pharmacological Characterization of KCNQ2 and KCNQ3

Stage V and VI *Xenopus laevis* oocytes were defolliculated with collagenase treatment and injected with cRNAs, as described in Yang et al., supra. Currents were recorded at room temperature using the two-microelectrode voltage clamp (Dagan TEV-200) technique between 3–5 days after injection of KCNQ2 (15 ng), KCNQ3 (15 ng), or KCNE1 (2 ng) cRNA alone or in combination. Microelectrodes (0.8 to 1.5 MΩ) were filled with 3 M KCl. Bath solution contained (in mM): 96 NaCl, 2 KCl, 0.4–1.8 $CaCl_2$, 1–2 $MgCl_2$ and 5 HEPES (pH 7.5). KCl was varied in some experiments by equimolar substitution with NaCl.

$K^+$ selectivity was assessed by determining the dependence of tail current reversal potential on the external $K^+$ concentration. Tail currents were elicited at potentials of −110 to +10 mV following a voltage step to +20 mV while the external $K^+$ concentration was varied between 2, 10, 40, and 98 mM. Current reversal potential under each condition was determined for each oocyte by measuring the zero intercept from a plot of tail current amplitude vs test potential.

Axoclamp (Axon Instruments) was used for generating voltage clamp commands and acquiring data and Axograph 3.0 (Axon Instruments) was used for data analysis. All data was sampled at rates at least two times the low pass filter rate. Experiments were performed at 22–25° C. Clofilum was obtained from RBI Biochemicals and 4-aminopyridine (4-AP), TEA and charybdotoxin were obtained from Sigma Chemical Co. E-4031 was synthesized from information published by Esai Research Laboratories.

Murine KvLR1
Probe Preparation and Library Screening

A unique expressed sequence tag (EST) was identified from the public database that has similarity to the KvLQT gene. Oligonucleotide primers were synthesized from the EST sequence for PCR experiments. The forward primer (SEQ. ID. NO.: 15) was 5'-GAG TAT GAG AAG AGC TCG GA-3' and reverse primer (SEQ. ID. NO.: 16) was

5'-CAG ATG TGG CAA AGA CGT TGC-3'.

Rat brain polyA$^+$ RNA was reverse-transcribed with random hexamers and amplified by PCR [60 sec 94° C., 90 sec 55° C., 120 sec 72° C., 30 cycles] with the above primers. A 240 bp DNA fragment of rat KCNQ2/KvLR1 was isolated by gel electrophoresis and subcloned into pCRII (InVitrogen). The 240 bp DNA fragment was random-prime labeled with $^{32}$P-dCTP and used as a probe to screen a mouse brain pcDNA1 plasmid library (Clontech, Palo Alto, Calif.). Overall, 2×10$^5$ colonies were screened using standard filter lift protocols. The filters were hybridized overnight in 50% formamide, 2×PIPES and 1% SDS at 42° C. and washed 1× in 1×SSC then 3×20 minutes in 0.1×SSC, 0.1% SDS at 53° C. Filters were exposed overnight at −70° C. Only one positive colony was identified and replated until purified. Clone mbr 26.1, designated murine KvLR1, was sequenced on both strands by dideoxy termination reactions.

Northern Blots

Northern blots were performed with the mouse multiple tissue blot (Clontech) according to the manufacturer's instructions. Briefly, the blot was prehybridized at 68° C. with ExpressHyb solution for 30 minutes. A DNA fragment was isolated from the murine KvLR1 coding region by the restriction enzyme PvuII, which eliminated the pore and voltage sensor consensus sequences, and random-prime labeled with $^{32}$P-dCTP, denatured at 100° C. for 5 minutes, chilled on ice and added to fresh ExpressHyb before addition to the northern blot. The blot was incubated for 60 minutes at 68° C. with continuous shaking. The blot was washed 2× at 50° C. in 0.1×SSC and 0.1% SDS. The blot was wrapped in saran wrap and exposed to x-ray film overnight at room temperature. The same protocol was used for the actin probe provided with the blot.

In Situ Hybridization

Frozen sections cut at intervals of 225 μm through the entire adult rat brain were fixed by immersion (without thawing) into ice cold 10% formaldehyde in PBS for 20 minutes and rinsed with PBS. Fixed sections of rat DRG were treated with 0.5% Triton X-100 in 0.1 M Tris, pH 8.0, and 0.05 M EDTA for 30 minutes and rinsed for 3 minutes in 0.1 M Tris, pH 8.0, and 0.05 M EDTA. The tissue was then treated with 0.1 M TEA, pH 8.0, plus 0.25% acetic anhydride for 10 minutes at room temperature, rinsed (3×) in 2×SSC, dehydrated through a series of alcohols, delipidated in chloroform, and air dried.

Riboprobes were synthesized using the Promega Riboprobe Transcription System II with 250 μCi $^{35}$S-UTP and 250 μCi $^{35}$S-CTP in a total reaction volume of 10 μL. Unlabeled UTP and CTP were added at 25 μM each and ATP and GTP at 500 μM each. The murine KCNQ2/KvLR1 plasmid (nts 552–1125 subcloned into pBluescript II) was linearized with Sac I and transcribed using T3 RNA polymerase, and with BamHiI and transcribed using SP6 RNA polymerase to generate anti-sense and sense probes, respectively. One μg of linearized plasmid was added for each reaction. The riboprobes were purified by phenol:chloroform extraction and two ethanol precipitations using ammonium acetate. The dried tissue sections were hybridized with 1×10$^7$ cpm/ml riboprobe in hybridization buffer (50% formamide, 0.3 M NaCl, 10 mM Tris, 1 mM EDTA, 1×Denhardt's solution, 10% dextran sulfate, 500 μg/ml tRNA and 10 mM DTT) overnight at 55° C. The hybridization solution was removed by rinsing 4 times in 4×SSC, 5 minutes for each wash. The sections were incubated in 0.02 mg/ml RNase, 0.5 M NaCl, 10 mM Tris, pH 8.0, and 1 mM EDTA for 30 minutes at 37° C., then washed in 2×SSC, 1×SSC and 0.5×SSC, all containing 1 mM DTT, for 10 minutes per wash at room temperature. The tissues were incubated in 0.1×SSC, 1 mM DTT for 30 minutes at 55° C., then rinsed briefly in 0.1×SSC and 1 mM DTT at room temperature, dehydrated, and air dried. The dried sections were exposed to XOMAT film (Kodak, Rochester, N.Y.), then were dipped in NTB2 emulsion (Kodak, Rochester, N.Y.) to determine the cellular localization of each mRNA.

Expression and Recording in Oocytes

The murine KCNQ2/KvLR1 cDNAs were linearized with the restriction enzyme NotI and in vitro transcribed using the mMessage mMachine T7 RNA polymerase kit according to the manufacturer's instructions (Ambion, Austin, Tex.). The cRNAs were solubilized in RNase-free water, and stored at −70° C. at a concentration of 1.0 μg/μl. Frog oocytes were prepared and injected using standard techniques (Colman, 1984). In murine KvLR1 expression experiments, each oocyte was injected with approximately 35–40 nl of the cRNA. Following injection, oocytes were maintained at 17° C. in ND96 medium consisting of (in mM): NaCl, 90; KCl, 1.0; CaCl$_2$, 1.0; MgCl$_2$, 1.0; HEPES, 5.0; pH 7.5. Horse serum and penicillin/streptomycin, both 5% of final volume, were added as supplements to the incubation medium. Electrophysiological recording commenced 2–6 days following cRNA injection. Prior to the start of an experiment oocytes were placed in a recording chamber and incubated in Modified Barth's Solution (MBS) consisting of (in mM): NaCl, 88; NaHCO3, 2.4; KCl, 1.0; HEPES, 10; MgSO$_4$, 0.82; Ca(NO$_3$)$_2$, 0.33; CaCl$_2$, 0.41; pH 7.5. Oocytes were impaled with electrodes (1–2 MΩ) and standard 2-electrode voltage clamp techniques were employed to record whole-cell membrane currents (Stuhmer, 1992; TEC 200, Dagan Instruments). Voltage-clamp protocols typically consisted of a series of voltage steps 100–500 ms duration, in +10 mV steps from a holding potential of −60 mV to −90 mV to a maximal potential of +40 mV to +50 mV; records were digitized at 5 kHz and stored on a computer using pClamp 6.0 software (Axon Instruments), and analyzed using ClampFit or AxoGraph software (Axon Instruments).

Expression and Recording in CHO Cells

Patch clamp recordings were obtained from CHO cells that transiently or stably expressed murine KCNQ2 channels. Electrodes were prepared using a PC-84 Sachs-Flaming pipette puller (Sutter Instruments) and fire-polished to a final tip resistance of 3–5 MΩ. Pipettes were filled with a solution that consisted of (in mM) KCl (140), MOPS (20), K$_2$EGTA (1.0), CaCl$_2$ (0.89), pH 7.2. The pipette solution sometimes contained MgCl$_2$ (1.0) to aid in seal formation. Cells were grown on poly-D-lysine coated coverslips, and pieces of the coverslips containing CHO cells were placed into a chamber on an inverted microscope for recording. Prior to recording, and during seal formation, cells were bathed in an external solution consisting of (in mM) NaCl (145), KCl (3), CaCl$_2$ (2.5), MgCl$_2$ (1.0), HEPES (10), pH 7.4. Electrodes were lowered to the surface of cells under visual inspection; following gigaseal formation inside-out membrane patches were excised into an internal solution consisting of (in mM) KCl (140), MOPS (20), K$_2$EGTA (1.0), CaCl$_2$ (0.89), pH 7.2. All recordings were made under symmetrical K$^+$ conditions. Following patch excision continuous and step-protocol voltage-clamp recordings were obtained, and analyses performed, using an AxoPatch 200B Patch Clamp amplifier and pClamp software (Axon Instruments). Results are shown in FIG. 22.

Although the present invention has been described in some detail by way of illustration and example for purposes of clarity and understanding, it will be apparent that certain changes and modifications may be practiced within the scope of the appended claims.

What is claimed is:

1. An isolated nucleic acid molecule encoding the amino acid square of human KCNO2 polypeptide as shown in SEQ ID NO:20.

2. An isolated nucleic acid molecule, wherein the sequence of said nucleic acid molecule is identical to the sequence in ATCC Deposit No. 203029 (human KCNQ2).

3. An isolated nucleic acid molecule encoding human KCNQ2 polypeptide, said nucleic acid molecule comprising (i) the polynucleotide sequence as depicted in SEQ ID NO:19, or (ii) the human KCNQ2 polypeptide coding region of the polynucleotide as depicted in FIGS. 2A and 2B and as set forth in SEQ ID NO:19.

4. The isolated nucleic acid molecule of claim 3, wherein the coding region of the human KCNQ2 polypeptide comprises a nucleic acid sequence comprising nucleotide position 61 through nucleotide position 2676 of SEQ ID NO:19.

5. An isolated nucleic acid molecule encoding human KCNQ2 polypeptide, said nucleic acid molecule consisting of the polynucleotide sequence as depicted in SEQ ID NO:3.

6. A vector comprising the isolated nucleic acid molecule of claim 3.

7. A vector comprising the isolated nucleic acid molecule of claim 1.

8. A vector comprising the isolated nucleic acid molecule of claim 4.

9. A prokaryotic or eukaryotic host cell comprising the vector of claim 6.

10. A prokaryotic or eukaryotic host cell comprising the vector of claim 7.

11. A prokaryotic or eukaryotic host cell comprising the vector of claim 8.

* * * * *

UNITED STATES PATENT AND TRADEMARK OFFICE
CERTIFICATE OF CORRECTION

PATENT NO. : 6,403,360 B1
DATED : June 11, 2002
INVENTOR(S) : Michael A. Blanar et al.

Figures 5A, 5B:
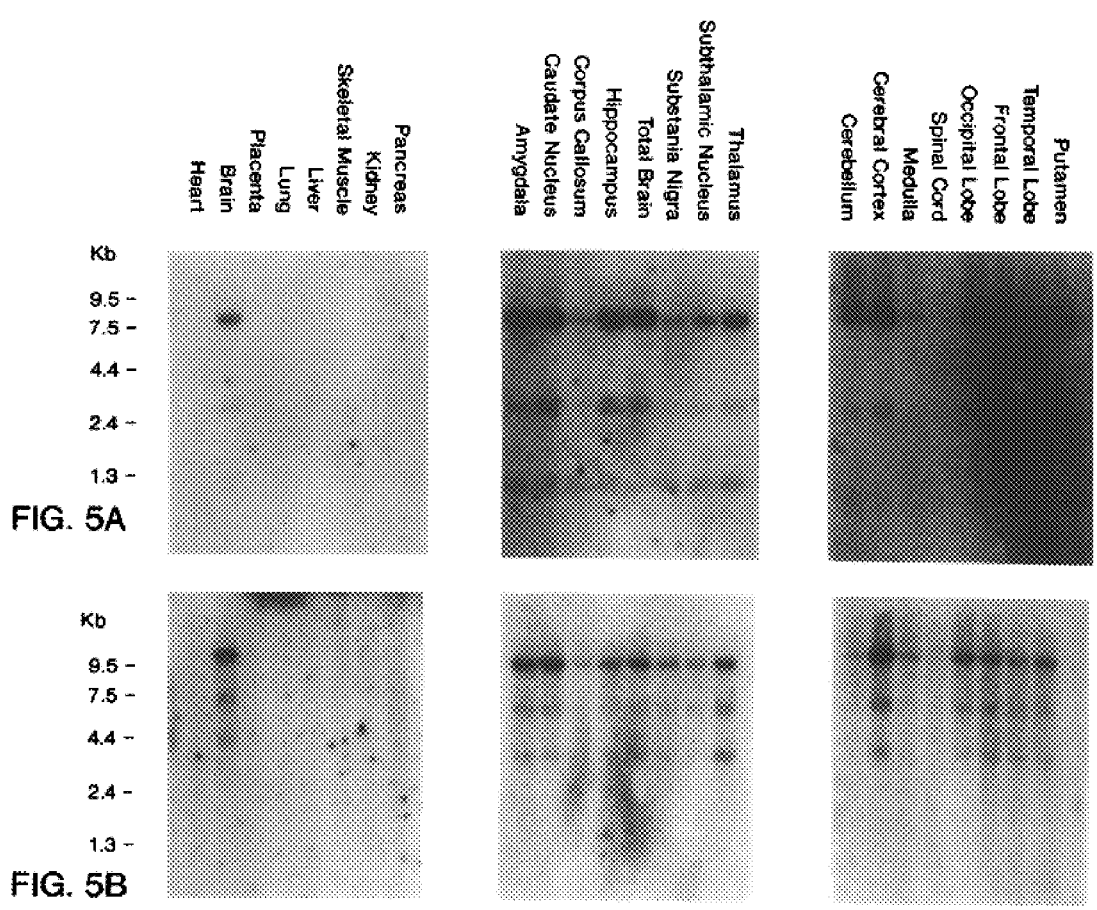
FIG. 5A shows KCNQ2/KvLR1.
FIG. 5B shows KCNQ3/KvLR2. Poly(A+) mRNA Northern blots were hybridized individually to radiolabeled KCNQ2-specific (FIG. 5A) or KCNQ3-specific (FIG. 5B) probes. RNA molecular weight markers are indicated on the left.

It is certified that error appears in the above-identified patent and that said Letters Patent is hereby corrected as shown below:

Column 3,
Line 49, "FIGS. 2A and 2B" should read -- FIGS. 2A-2F --.
Line 63, "FIG. 5 shows" should read -- FIGS. 5A and 5B show --.

Figure 8B:
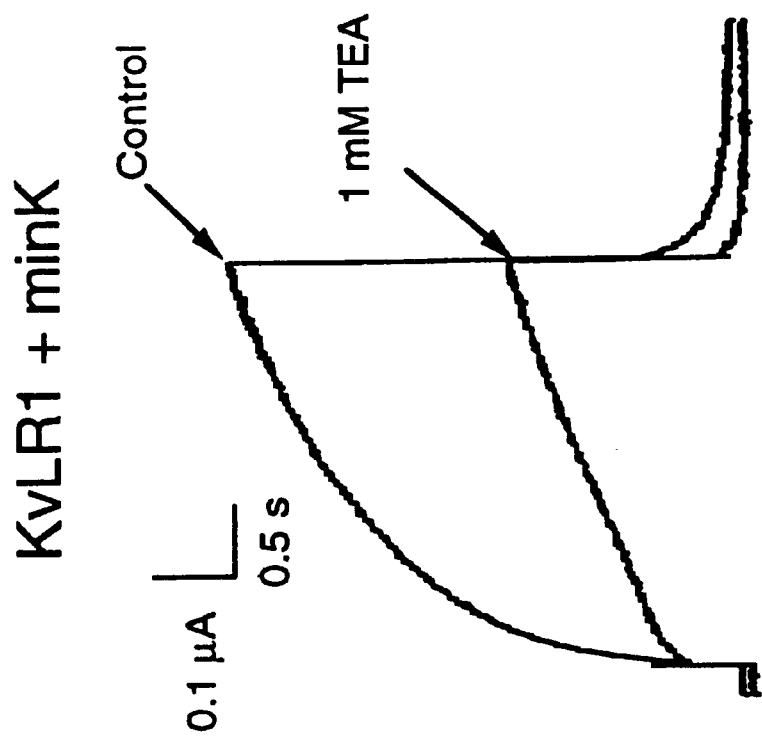
FIG. 8B shows the effect of 1 mM TEA on membrane currents recorded from an oocyte injected with minK and human KCNQ2/KvLR1. Currents were elicited using the protocol in FIG. 8A. TEA partially inhibited minK + human KCNQ2/KvLR1 currents, however, the amplitude and kinetics of the TEA-insensitive current component were similar to currents observed in oocytes injected with minK alone.
Figure 8A:
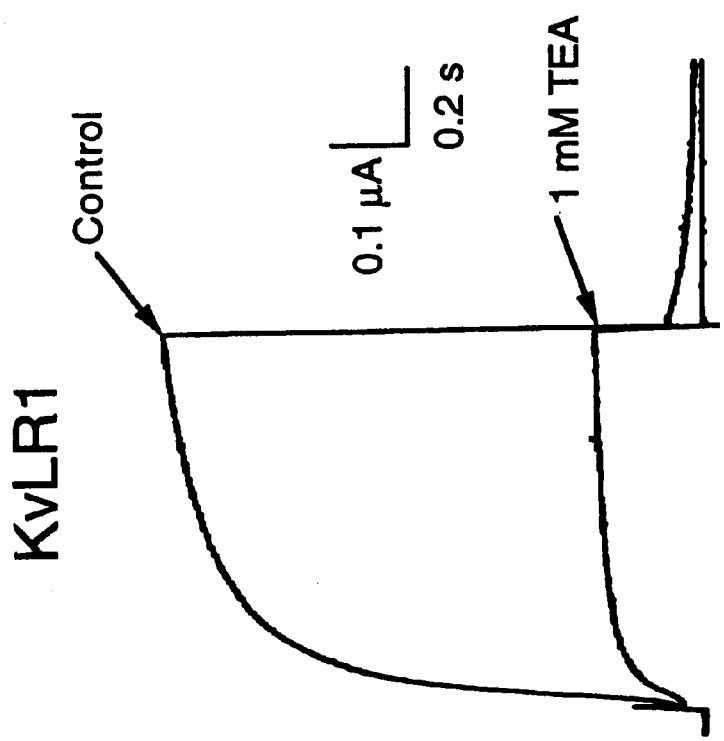
FIG. 8A shows the effect of 1 mM TEA on membrane currents recorded from an oocyte injected with human KCNQ2/KvLR1 alone. Superimposed currents were recorded during 1 second voltage steps to +40 mV from a holding potential of −80 mV before and after applying TEA via the bath. TEA reduced human KCNQ2/KvLR1 current by over 80%.

Column 4,
Line 3, "FIG. 6 shows" should read -- FIGS. 6A-6D show --.
Line 36, "FIG. 8 shows" should read -- FIGS. 8A and 8B show --.
Line 53, "FIG. 9 shows" should read -- FIGS. 9A-9C show --.

Column 5,
Line 48, "FIG. 14 shows" should read -- FIGS. 14A-14D show --.
Line 54, "FIG. 15 shows" should read -- FIGS. 15A and 15B show --.
Line 65, "FIG. 16 shows" should read -- FIGS. 16A-16D show --.

Column 6,
Line 7, "FIG. 17 shows" should read -- FIGS. 17A and 17B show --.
Line 16, "FIG. 18 shows" should read -- FIGS. 18A-18D show --.
Line 35, "FIG. 19 shows" should read -- FIGS. 19A-19F show --.
Line 54, "FIG. 20 shows" should read -- FIGS. 20A-20C show --.
Line 64, "FIG. 21 is a photograph" should read -- FIGS. 21A and 21B are photographs --.

Column 7,
Line 13, "FIG. 23 shows" should read -- FIGS. 23A to 23E show --.

UNITED STATES PATENT AND TRADEMARK OFFICE
CERTIFICATE OF CORRECTION

PATENT NO. : 6,403,360 B1
DATED : June 11, 2002
INVENTOR(S) : Michael A. Blanar et al.

It is certified that error appears in the above-identified patent and that said Letters Patent is hereby corrected as shown below:

Column 65,
Line 23, "square" should read -- sequence --.
Line 23, "KCNO2" should read -- KCNQ2 --.

Signed and Sealed this

Twenty-first Day of January, 2003

JAMES E. ROGAN
*Director of the United States Patent and Trademark Office*

SEQUENCE LISTING

<160> NUMBER OF SEQ ID NOS: 28

<210> SEQ ID NO 1
<211> LENGTH: 896
<212> TYPE: DNA

-continued

<213> ORGANISM: Artificial Sequence
<220> FEATURE:
<223> OTHER INFORMATION: Description of Artificial Sequence:Consensus nucleotide sequence as shown in Fig. 16A-16D
<223> OTHER INFORMATION: y=c or t; r=a or g; m=a or c; k=g or t; s=g or c; w=a or t; h=a, c, or t; b=g, t, or c; v=g, c, or a

<400> SEQUENCE: 1
rrsrcsssvs ysrgsmrscc msysaagmgm aacgccwwst accgsmrsmt s caramttts 60 mtctacracg ysctrgagmg rccscgsggc tgggcgytsm tytaccacgc s twsgtgttc 120 ctbhtdgtyy tsksstgcyt brtkctgkct gtsykwccac mwtcaaggag t aygagamkr 180 kytcbgrrgr skssctyyws wtmytggara ymktkrcyat yktsrtvtty g ghgybgagt 240 wykyyktgmg ratctgggcy gcwggmtgyt sytgccgrta cmrwggctgg m ggggsmgrc 300 tsaagtttgc cmggaarccv ctstgyrtgw tbgayatcwt kgtgctsaty g cctcyrtks 360 cdgtgstkgc ygybgghwmc carggcaayg tyytkgcyac vtcyctbcgr a gcytgcgst 420 tcytrcarat yytrcgsatg mtscgbatgg accggmgrgg hggcacctgg a agctbytgg 480 gmtcdgyvrt ctrygcycac agcaargarc tsrtsackgc stggtacaty g gyttcctbw 540 shctcatcct kkcytcrtty ctkgtstacy tggywgaraa rssdgagrwb g aysmmttyg 600 asacctaygc rgatgcmcts tggtggggyc tgatcacvct grcvaccatt g gctayggrg 660 acaagwmmcc ymaracstgg ramggsmgkc tshtdgcvgc vacsttywcc y tmatyggyg 720 tctcvttytt ygcbctkccw gcdggcatyy tgggrtcygg sytkgcccts a argtbcarg 780 agcarcaymg kcaraarcac tttgagaarm ggmggaabcc dgcdgcwgrb c tsatycagk 840 ckgcctggag rtwytaygcy acyaaccycw mvmgsayhga cctgswykse r mswkg 896

<210> SEQ ID NO 2
<211> LENGTH: 298
<212> TYPE: PRT
<213> ORGANISM: Artificial Sequence
<220> FEATURE:
<223> OTHER INFORMATION: Description of Artificial Sequence:Consensus amino acid sequence as shown in Fig. 17A-17B
<223> OTHER INFORMATION: Xaa is any amino ac id

<400> SEQUENCE: 2

Xaa Xaa Xaa Xaa Xaa Xaa Pro Xaa Lys Arg A sn Ala Xaa Tyr Arg Xaa
1 5 10 15

Xaa Gln Xaa Xaa Xaa Tyr Xaa Xaa Leu Glu A rg Pro Arg Gly Trp Ala
20 25 30

Xaa Xaa Tyr His Ala Xaa Val Phe Leu Xaa V al Xaa Xaa Cys Leu Xaa
35 40 45

Leu Xaa Val Xaa Xaa Thr Xaa Lys Glu Tyr G lu Xaa Xaa Ser Xaa Xaa
50 55 60

Xaa Leu Xaa Xaa Leu Glu Xaa Xaa Xaa Ile X aa Xaa Phe Gly Xaa Glu
65 70 75 80

Xaa Xaa Xaa Arg Ile Trp Ala Ala Gly Cys C ys Cys Arg Tyr Xaa Gly
85 90 95

Trp Arg Gly Arg Leu Lys Phe Ala Arg Lys P ro Xaa Cys Xaa Xaa Asp
100 105 110

Ile Val Leu Ile Ala Ser Xaa Xaa Val Xaa A la Xaa Gly Xaa Gln Gly
115 120 125

Asn Val Xaa Ala Thr Ser Leu Arg Ser Leu A rg Phe Leu Gln Ile Leu
130 135 140

Arg Met Xaa Arg Met Asp Arg Arg Gly Gly T hr Trp Lys Leu Leu Gly

-continued

```
145                 150                 155                 160
Ser Xaa Xaa Xaa Ala His Ser Lys Glu Leu Xaa Thr Ala Trp Tyr Ile
                165                 170                 175
Gly Phe Leu Xaa Leu Ile Leu Xaa Ser Phe Leu Val Tyr Leu Xaa Glu
            180                 185                 190
Lys Xaa Glu Xaa Asp Xaa Phe Xaa Thr Tyr Ala Asp Ala Leu Trp Trp
        195                 200                 205
Gly Leu Ile Thr Leu Xaa Thr Ile Gly Tyr Gly Asp Lys Xaa Pro Xaa
    210                 215                 220
Thr Trp Xaa Gly Arg Leu Xaa Ala Ala Thr Phe Xaa Leu Ile Gly Val
225                 230                 235                 240
Ser Phe Phe Ala Leu Pro Ala Gly Ile Leu Gly Ser Gly Xaa Ala Leu
                245                 250                 255
Lys Val Gln Glu Gln His Arg Gln Lys His Phe Glu Lys Arg Arg Xaa
            260                 265                 270
Pro Ala Ala Xaa Leu Ile Gln Xaa Ala Trp Arg Xaa Tyr Ala Thr Asn
        275                 280                 285
Xaa Xaa Arg Xaa Asp Leu Xaa Xaa Xaa Xaa
    290                 295
```

<210> SEQ ID NO 3
<211> LENGTH: 900
<212> TYPE: DNA
<213> ORGANISM: Homo sapiens
<220> FEATURE:
<223> OTHER INFORMATION: 900 nucleotides of human KCNQ2

<400> SEQUENCE: 3

```
ggcgcgggcg ccgggaagcc ccccaagcgc aacgccttct accgcaagct g cagaatttc     60
ctctacaacg tgctggagcg gccgcgcggc tgggcgttca tctaccacgc c tacgtgttc    120
ctcctggttt tctcctgcct cgtgctgtct gtgttttcca ccatcaagga g tatgagaag    180
agctcggagg gggcccttca tcctggaaa atcgtgacta tcgtggtgtt t ggcgtggag    240
tacttcgtgc ggatctgggc cgcaggctgc tgctgccggt accgtggctg g aggggggcgg    300
ctcaagtttg cccggaaacc gctctgtgtg attgacatca tggtgctcat c gcctccatt    360
gcggtgctgg ccgccggctc ccagggcaac gtctttgcca catctgcgct c cggagcctg    420
cgcttcctgc agattctgcg gatgatccga atggaccggc ggggaggcac c tggaagctg    480
ctgggctctg tggtctatgc ccacagcaag gagctggtca ctgcctggta c atcggcttc    540
ctttgtctca tcctggcctc gttcctggtg tacttggcag agaaggggga g aacgaccac    600
tttgacacct acgcggatgc actctggtgg ggcctgatca cgctgaccac c attggctac    660
ggggacaagt accccagac tggaacggc aggctccttg cggcaaccttc c acctcatc    720
ggtgtctcct tcttcgcgct gcctgcaggc atcttggggt ctgggtttgc c tgaaggtt    780
caggagcagc acaggcagaa gcactttgag aagaggcgga accggcagc a ggcctgatc    840
cagtcggcct ggagatttta cgccaccaac ctctcgcgca cagacctgca c tccacgtgg    900
```

<210> SEQ ID NO 4
<211> LENGTH: 300
<212> TYPE: PRT
<213> ORGANISM: Homo sapiens
<220> FEATURE:
<223> OTHER INFORMATION: 300 amino acids of human KCNQ2

<400> SEQUENCE: 4

```
Gly Ala Gly Ala Gly Lys Pro Pro Lys Arg Asn Ala Phe Tyr Arg Lys
 1               5                  10                  15
Leu Gln Asn Phe Leu Tyr Asn Val Leu Glu Arg Pro Arg Gly Trp Ala
                 20                  25                  30
Phe Ile Tyr His Ala Tyr Val Phe Leu Leu Val Phe Ser Cys Leu Val
             35                  40                  45
Leu Ser Val Phe Ser Thr Ile Lys Glu Tyr Glu Lys Ser Ser Glu Gly
         50                  55                  60
Ala Leu Tyr Ile Leu Glu Ile Val Thr Ile Val Val Phe Gly Val Glu
 65                  70                  75                  80
Tyr Phe Val Arg Ile Trp Ala Ala Gly Cys Cys Cys Arg Tyr Arg Gly
                 85                  90                  95
Trp Arg Gly Arg Leu Lys Phe Ala Arg Lys Pro Phe Cys Val Ile Asp
                100                 105                 110
Ile Met Val Leu Ile Ala Ser Ile Ala Val Leu Ala Ala Gly Ser Gln
             115                 120                 125
Gly Asn Val Phe Ala Thr Ser Ala Leu Arg Ser Leu Arg Phe Leu Gln
 130                 135                 140
Ile Leu Arg Met Ile Arg Met Asp Arg Arg Gly Gly Thr Trp Lys Leu
145                 150                 155                 160
Leu Gly Ser Val Val Tyr Ala His Ser Lys Glu Leu Val Thr Ala Trp
                165                 170                 175
Tyr Ile Gly Phe Leu Cys Leu Ile Leu Ala Ser Phe Leu Val Tyr Leu
            180                 185                 190
Ala Glu Lys Gly Glu Asn Asp His Phe Asp Thr Tyr Ala Asp Ala Leu
            195                 200                 205
Trp Trp Gly Leu Ile Thr Leu Thr Thr Ile Gly Tyr Gly Asp Lys Tyr
 210                 215                 220
Pro Gln Thr Trp Asn Gly Arg Leu Leu Ala Ala Thr Phe Thr Leu Ile
225                 230                 235                 240
Gly Val Ser Phe Phe Ala Leu Pro Ala Gly Ile Leu Gly Ser Gly Phe
                245                 250                 255
Ala Leu Lys Val Gln Glu Gln His Arg Gln Lys His Phe Glu Lys Arg
            260                 265                 270
Arg Asn Pro Ala Ala Gly Leu Ile Gln Ser Ala Trp Arg Phe Tyr Ala
            275                 280                 285
Thr Asn Leu Ser Arg Thr Asp Leu His Ser Thr Trp
 290                 295                 300

<210> SEQ ID NO 5
<211> LENGTH: 900
<212> TYPE: DNA
<213> ORGANISM: mouse
<220> FEATURE:
<223> OTHER INFORMATION: 900 nucleotides of murine KCNQ2

<400> SEQUENCE: 5
ggcgcgggag ccgggaagcc cccgaagcgc aacgccttct accgcaagct gcagaatttc      60
ctctacaacg tgctagagcg gccccgcggc tgggcgttca tctaccacgc ctacgtgttc     120
cttttagtct tctcctgcct tgtgctttct gtgttttcca ccatcaagga gtacgagaag     180
agctctgagg gggccctcta catcttggaa atcgtgacta tcgtggtatt cggtgttgag     240
tactttgtga ggatctgggc tgcaggctgc tgttgccggt atcgaggctg gaggggcagg     300
ctcaagtttg ccaggaagcc gttctgtgtg attgatatca tggtgctgat tgcctccatt     360
```

```
gctgtgctgg ctgctggttc ccagggcaat gtctttgcca catctgcgct t cggagcttg    420 cggttcttgc aaatcttgcg gatgatccgt atggaccgga ggggtggcac c tggaagctc    480 ttgggatcgg tagtctacgc tcacagcaag gagctggtga ctgcctggta c attggcttc    540 ctctgcctca tcctggcctc atttctggtg tacttggcag aaaagggtga g aatgaccac    600 tttgacacct acgcagatgc actctggtgg gtctgatca ccctgacgac c attggctac    660 ggggacaagt accctcagac ctggaacggg aggctgctgg cagcgacctt t accctcatt    720 ggtgtctcgt tctttgctct tcctgctggc attttgggat ccggctttgc c ctgaaagtc    780 caagagcagc atcggcaaaa acactttgag aaacggcgga accctgcggc a ggtctgatc    840 cagtctgcct ggagattcta tgctactaac ctctcacgca ccgacctgca c tccacgtgg    900
```

<210> SEQ ID NO 6
<211> LENGTH: 300
<212> TYPE: PRT
<213> ORGANISM: mouse
<220> FEATURE:
<223> OTHER INFORMATION: 300 amino acids of murine KCNQ2

<400> SEQUENCE: 6

```
Gly Ala Gly Ala Gly Lys Pro Pro Lys Arg Asn Ala Phe Tyr Arg Lys
  1               5                  10                  15

Leu Gln Asn Phe Leu Tyr Asn Val Leu Glu Arg Pro Arg Gly Trp Ala
             20                  25                  30

Phe Ile Tyr His Ala Tyr Val Phe Leu Leu Val Phe Ser Cys Leu Val
         35                  40                  45

Leu Ser Val Phe Ser Thr Ile Lys Glu Tyr Glu Lys Ser Ser Glu Gly
     50                  55                  60

Ala Leu Tyr Ile Leu Glu Ile Val Thr Ile Val Val Phe Gly Val Glu
 65                  70                  75                  80

Tyr Phe Val Arg Ile Trp Ala Ala Gly Cys Cys Cys Arg Tyr Arg Gly
                 85                  90                  95

Trp Arg Gly Arg Leu Lys Phe Ala Arg Lys Pro Phe Cys Val Ile Asp
            100                 105                 110

Ile Met Val Leu Ile Ala Ser Ile Ala Val Leu Ala Ala Gly Ser Gln
        115                 120                 125

Gly Asn Val Phe Ala Thr Ser Ala Leu Arg Ser Leu Arg Phe Leu Gln
    130                 135                 140

Ile Leu Arg Met Ile Arg Met Asp Arg Arg Gly Gly Thr Trp Lys Leu
145                 150                 155                 160

Leu Gly Ser Val Val Tyr Ala His Ser Lys Glu Leu Val Thr Ala Trp
                165                 170                 175

Tyr Ile Gly Phe Leu Cys Leu Ile Leu Ala Ser Phe Leu Val Tyr Leu
            180                 185                 190

Ala Glu Lys Gly Glu Asn Asp His Phe Asp Thr Tyr Ala Asp Ala Leu
        195                 200                 205

Trp Trp Gly Leu Ile Thr Leu Thr Thr Ile Gly Tyr Gly Asp Lys Tyr
    210                 215                 220

Pro Gln Thr Trp Asn Gly Arg Leu Leu Ala Ala Thr Phe Thr Leu Ile
225                 230                 235                 240

Gly Val Ser Phe Phe Ala Leu Pro Ala Gly Ile Leu Gly Ser Gly Phe
                245                 250                 255

Ala Leu Lys Val Gln Glu Gln His Arg Gln Lys His Phe Glu Lys Arg
            260                 265                 270
```

```
Arg Asn Pro Ala Ala Gly Leu Ile Gln Ser A la Trp Arg Phe Tyr Ala
        275                 280                 285
Thr Asn Leu Ser Arg Thr Asp Leu His Ser T hr Trp
        290                 295                 300

<210> SEQ ID NO 7
<211> LENGTH: 735
<212> TYPE: DNA
<213> ORGANISM: rat

<400> SEQUENCE: 7
aaggagtatg agaagagttc gagggggcc ctctacatct tggaaatcgt g accatcgtg      60
gtattcggtg ttgagtactt tgtgagaatc tgggctgcag gctgctgctg c cggtatcga    120
ggctggaggg gccggctcaa gtttgccagg aagccattct gtgtgatcga c atcatggtg    180
ctgattgcct ccattgctgt gctggctgct ggctcccagg gcaatgtctt t gctacgtct    240
gcacttcgga gcttgcggtt cttacaaatc ttacggatga tccgtatgga c cggaggggc    300
ggcacctgga agctcctggg atcggtggtc tacgctcaca gcaaggagct g gtgactgcg    360
tggtacattg gcttcctctg cctcatcctg gcctcgtttc tggtgtactt g cagaaaaag    420
ggtgagaatg accacttcga cacctacgcg gatgcactct ggtggggtct g atcaccctg    480
acaaccattg gctacgggga caagtaccct cagacctgga cgggaggct g ttagcagcg    540
acgtttaccc tcattggtgt ctcattcttc gctcttcctg ctggcatttt g gatccggc    600
tttgccctga agtccaaga gcagcatcgg caaaaacact tgagaaacg g cggaatcct    660
gcggcaggtc tcatccagtc tgcctggaga ttctatgcta ctaacctctc a cgcaccgac   720
ctgcactcca cgtgg                                                       735

<210> SEQ ID NO 8
<211> LENGTH: 245
<212> TYPE: PRT
<213> ORGANISM: rat

<400> SEQUENCE: 8

Lys Glu Tyr Glu Lys Ser Ser Glu Gly Ala L eu Tyr Ile Leu Glu Ile
  1               5                  10                  15
Val Thr Ile Val Val Phe Gly Val Glu Tyr P he Val Arg Ile Trp Ala
            20                  25                  30
Ala Gly Cys Cys Cys Arg Tyr Arg Gly Trp A rg Gly Arg Leu Lys Phe
        35                  40                  45
Ala Arg Lys Pro Phe Cys Val Ile Asp Ile M et Val Leu Ile Ala Ser
    50                  55                  60
Ile Ala Val Leu Ala Ala Gly Ser Gln Gly A sn Val Phe Ala Thr Ser
65                  70                  75                  80
Ala Leu Arg Ser Leu Arg Phe Leu Gln Ile L eu Arg Met Ile Arg Met
                85                  90                  95
Asp Arg Arg Gly Gly Thr Trp Lys Leu Leu G ly Ser Val Val Tyr Ala
            100                 105                 110
His Ser Lys Glu Leu Val Thr Ala Trp Tyr I le Gly Phe Leu Cys Leu
        115                 120                 125
Ile Leu Ala Ser Phe Leu Val Tyr Leu Ala G lu Lys Gly Glu Asn Asp
    130                 135                 140
His Phe Asp Thr Tyr Ala Asp Ala Leu Trp T rp Gly Leu Ile Thr Leu
145                 150                 155                 160
Thr Thr Ile Gly Tyr Gly Asp Lys Tyr Pro G ln Thr Trp Asn Gly Arg
```

```
                    165                 170                 175
Leu Leu Ala Ala Thr Phe Thr Leu Ile Gly Val Ser Phe Phe Ala Leu
                180                 185                 190

Pro Ala Gly Ile Leu Gly Ser Gly Phe Ala Leu Lys Val Gln Glu Gln
            195                 200                 205

His Arg Gln Lys His Phe Glu Lys Arg Arg Asn Pro Ala Ala Gly Leu
        210                 215                 220

Ile Gln Ser Ala Trp Arg Phe Tyr Ala Thr Asn Leu Ser Arg Thr Asp
225                 230                 235                 240

Leu His Ser Thr Trp
                245
```

<210> SEQ ID NO 9
<211> LENGTH: 226
<212> TYPE: DNA
<213> ORGANISM: mouse

<400> SEQUENCE: 9

```
gagcagcaca ggcagaaaca ctttgagaaa cggcggaacc ctgcggcagg t ctgatccag    60
tctgcctgga gattctatgc tactaacctc ttacgcaccg acctgcactc c acgtggcag  120
tactacgagc ggacagtcac tgtccccatg tacagctcac aaactcaaac c tatggggcc  180
tccagactca tcccacctct gaaccagctg gagctgctga gaaaca               226
```

<210> SEQ ID NO 10
<211> LENGTH: 75
<212> TYPE: PRT
<213> ORGANISM: mouse

<400> SEQUENCE: 10

```
Glu Gln His Arg Gln Lys His Phe Glu Lys Arg Arg Asn Pro Ala Ala
 1               5                  10                  15

Gly Leu Ile Gln Ser Ala Trp Arg Phe Tyr Ala Thr Asn Leu Leu Arg
            20                  25                  30

Thr Asp Leu His Ser Thr Trp Gln Tyr Tyr Glu Arg Thr Val Thr Val
        35                  40                  45

Pro Met Tyr Ser Ser Gln Thr Gln Thr Tyr Gly Ala Ser Arg Leu Ile
    50                  55                  60

Pro Pro Leu Asn Gln Leu Glu Leu Leu Arg Asn
 65                  70                  75
```

<210> SEQ ID NO 11
<211> LENGTH: 30
<212> TYPE: DNA
<213> ORGANISM: Artificial Sequence
<220> FEATURE:
<223> OTHER INFORMATION: Description of Artificial  Sequence:PCR probe
      based on the human KNCQ2/KvLRI s equence

<400> SEQUENCE: 11

```
ggccgaattc tgtttctcag cagctccagc                                      30
```

<210> SEQ ID NO 12
<211> LENGTH: 30
<212> TYPE: DNA
<213> ORGANISM: Artificial Sequence
<220> FEATURE:
<223> OTHER INFORMATION: Description of Artificial  Sequence:PCR probe
      based on the human KCNQ2/KvLRI s equence

<400> SEQUENCE: 12

```
gcgcgaattc gagcagcaca ggcaraarca                                      30
```

<210> SEQ ID NO 13
<211> LENGTH: 10
<212> TYPE: PRT
<213> ORGANISM: mouse

<400> SEQUENCE: 13

Ser Ser Gln Thr Gln Thr Tyr Gly Ala Ser
 1               5                  10

<210> SEQ ID NO 14
<211> LENGTH: 18
<212> TYPE: PRT
<213> ORGANISM: mouse

<400> SEQUENCE: 14

Lys Gly Ser Pro Cys Arg Gly Pro Leu Cys Gly Cys Cys Pro Gly Arg
 1               5                  10                  15

Ser Ser

<210> SEQ ID NO 15
<211> LENGTH: 20
<212> TYPE: DNA
<213> ORGANISM: Artificial Sequence
<220> FEATURE:
<223> OTHER INFORMATION: Description of Artificial  Sequence:Forward
      primer from EST sequence similar to the KvLQT gene

<400> SEQUENCE: 15

```
gagtatgaga agagctcgga                                                 20
```

<210> SEQ ID NO 16
<211> LENGTH: 21
<212> TYPE: DNA
<213> ORGANISM: Artificial Sequence
<220> FEATURE:
<223> OTHER INFORMATION: Description of Artificial  Sequence:Reverse
      primer from EST sequence similar to the KvLQT gene

<400> SEQUENCE: 16

```
cagatgtggc aaagacgttg c                                               21
```

<210> SEQ ID NO 17
<211> LENGTH: 930
<212> TYPE: DNA
<213> ORGANISM: Homo sapiens
<220> FEATURE:
<223> OTHER INFORMATION: 930 nucleotides of hum an KCNQ3

<400> SEQUENCE: 17

```
aagaccccgc tgagccgccc agtcaagaga acaacgcca  agtaccggcg c atccaaact    60
ttgatctacg acgccctgga gaccgcgcgg ggctgggcgc tgctttacca c gcgttggtg   120
ttcctgattg tcctggggtg cttgattctg gctgtcctga ccacattcaa g gagtatgag   180
actgtctcgg gagactggct tctgttactg gagacatttg ctattttcat c tttggagcc   240
gagtttgctt tgaggatctg ggctgctgga tgttgctgcc gatacaaagg c tggcgggc    300
cgactgaagt tgccaggaa  gcccctgtgc atgttggaca tctttgtgct g attgcctct   360
gtgccagtgg ttgctgtggg aaaccaaggc aatgttctgg ccacctccct g cgaagcctg   420
cgcttcctgc agatcctgcg catgctgcgg atggaccgga gaggtggcac c tggaagctt   480
```

-continued

```
ctgggctcag ccatctgtgc ccacagcaaa gaactcatca cggcctggta c atcggtttc      540 ctgacactca tcctttcttc atttcttgtc tacctggttg agaaagacgt c ccagaggtg      600 gatgcacaag gagaggagat gaaagaggag tttgagacct atgcagatgc c ctgtggtgg      660 ggcctgatca cactggccac cattggctat ggagacaaga cacccaaaac g tgggaaggc      720 cgtctgattg ccgccacctt ttccttaatt ggcgtctcct tttttgccct t ccagcgggc      780 atcctggggt ccgggctggc cctcaaggtg caggagcaac accgtcagaa g cactttgag      840 aaaaggagga agccagctgc tgagctcatt caggctgcct ggaggtatta t gctaccaac      900 cccaacagga ttgacctggt tggcgacatg                                         930
```

<210> SEQ ID NO 18
<211> LENGTH: 310
<212> TYPE: PRT
<213> ORGANISM: Homo sapiens
<220> FEATURE:
<223> OTHER INFORMATION: 310 amino acids of human KCNQ3

<400> SEQUENCE: 18

```
Lys Thr Pro Leu Ser Arg Pro Val Lys Arg A sn Asn Ala Lys Tyr Arg
 1               5                  10                  15

Arg Ile Gln Thr Leu Ile Tyr Asp Ala Leu G lu Arg Pro Arg Gly Trp
             20                  25                  30

Ala Leu Leu Tyr His Ala Leu Val Phe Leu I le Val Leu Gly Cys Leu
         35                  40                  45

Ile Leu Ala Val Leu Thr Thr Phe Lys Glu T yr Glu Thr Val Ser Gly
     50                  55                  60

Asp Trp Leu Leu Leu Leu Glu Thr Phe Ala I le Phe Ile Phe Gly Ala
 65                  70                  75                  80

Glu Phe Ala Leu Arg Ile Trp Ala Ala Gly C ys Cys Cys Arg Tyr Lys
                 85                  90                  95

Gly Trp Arg Gly Arg Leu Lys Phe Ala Arg L ys Pro Leu Cys Met Leu
            100                 105                 110

Asp Ile Phe Val Leu Ile Ala Ser Val Pro V al Val Ala Val Gly Asn
        115                 120                 125

Gln Gly Asn Val Leu Ala Thr Ser Leu Arg S er Leu Arg Phe Leu Gln
    130                 135                 140

Ile Leu Arg Met Leu Arg Met Asp Arg Arg G ly Gly Thr Trp Lys Leu
145                 150                 155                 160

Leu Gly Ser Ala Ile Cys Ala His Ser Lys G lu Leu Ile Thr Ala Trp
                165                 170                 175

Tyr Ile Gly Phe Leu Thr Leu Ile Leu Ser S er Phe Leu Val Tyr Leu
            180                 185                 190

Val Glu Lys Asp Val Pro Glu Val Asp Ala G ln Gly Glu Glu Met Lys
        195                 200                 205

Glu Glu Phe Glu Thr Tyr Ala Asp Ala Leu T rp Trp Gly Leu Ile Thr
    210                 215                 220

Leu Ala Thr Ile Gly Tyr Gly Asp Lys Thr P ro Lys Thr Trp Glu Gly
225                 230                 235                 240

Arg Leu Ile Ala Ala Thr Phe Ser Leu Ile G ly Val Ser Phe Phe Ala
                245                 250                 255

Leu Pro Ala Gly Ile Leu Gly Ser Gly Leu A la Leu Lys Val Gln Glu
            260                 265                 270

Gln His Arg Gln Lys His Phe Glu Lys Arg A rg Lys Pro Ala Ala Glu
        275                 280                 285
```

Leu Ile Gln Ala Ala Trp Arg Tyr Tyr Ala Thr Asn Pro Asn Arg Ile
    290                 295                 300

Asp Leu Val Gly Asp Met
305                 310

<210> SEQ ID NO 19
<211> LENGTH: 3287
<212> TYPE: DNA
<213> ORGANISM: Homo sapiens

<400> SEQUENCE: 19

| | | | | | | |
|---|---|---|---|---|---|---|
| cccccgcgct | ccgccccgc | tgagcctgag | cccgacccgg | ggcgcctccc | g ccaggcacc | 60 |
| atggtgcaga | agtcgcgcaa | cggcggcgta | taccccggcc | cgagcgggga | g aagaagctg | 120 |
| aaggtgggct | tcgtggggct | ggaccccggc | gcgcccgact | ccacccggga | c ggggcgctg | 180 |
| ctgatcgccg | gctccgaggc | ccccaagcgc | ggcagcatcc | tcagcaaacc | t cgcgcgggc | 240 |
| ggcgcgggcg | ccgggaagcc | cccaagcgc | aacgccttct | accgcaagct | g cagaatttc | 300 |
| ctctacaacg | tgctggagcg | gccgcgcggc | tgggcgttca | tctaccacgc | c tacgtgttc | 360 |
| ctcctggttt | tctcctgcct | cgtgctgtct | gtgttttcca | ccatcaagga | g tatgagaag | 420 |
| agctcggagg | gggccctcta | catcctggaa | atcgtgacta | tcgtggtgtt | t ggcgtggag | 480 |
| tacttcgtgc | ggatctgggc | cgcaggctgc | tgctgccggt | accgtggctg | g aggggcgg | 540 |
| ctcaagtttg | cccggaaacc | gttctgtgtg | attgacatca | tggtgctcat | c gcctccatt | 600 |
| gcggtgctgg | ccgccggctc | ccagggcaac | gtctttgcca | catctgcgct | c cggagcctg | 660 |
| cgcttcctgc | agattctgcg | gatgatccgc | atggaccggc | ggggaggcac | c tggaagctg | 720 |
| ctgggctctg | tggtctatgc | ccacagcaag | gagctggtca | ctgcctggta | c atcggcttc | 780 |
| ctttgtctca | tcctggcctc | gttcctggtg | tacttggcag | agaaggggga | g aacgaccac | 840 |
| tttgacacct | acgcggatgc | actctggtgg | ggcctgatca | cgctgaccac | c attggctac | 900 |
| ggggacaagt | accccagac | ctggaacggc | aggctccttg | cggcaacctt | c accctcatc | 960 |
| ggtgtctcct | tcttcgcgct | gcctgcaggc | atcttgggt | ctgggtttgc | c ctgaaggtt | 1020 |
| caggagcagc | acaggcagaa | gcactttgag | aagaggcgga | accggcagc | a ggcctgatc | 1080 |
| cagtcggcct | ggagatttta | cgccaccaac | ctctcgcgca | cagacctgca | c tccacgtgg | 1140 |
| cagtactacg | agcgaacggt | caccgtgccc | atgtacagtt | cgcaaactca | a acctacggg | 1200 |
| gcctccagac | ttatccccc | gctgaaccag | ctggagctgc | tgagaaacct | c aagagtaaa | 1260 |
| tctggactcg | ctttcaggaa | ggaccccccg | ccggagccgt | ctccaagtaa | a ggcagcccg | 1320 |
| tgcagagggc | ccctgtgtgg | atgctgcccc | ggacgctcta | gccagaaggt | c agtttgaaa | 1380 |
| gatcgtgtct | tctccagccc | ccgaggcgtg | gctgccaagg | ggaagggtc | c ccgcaggcc | 1440 |
| cagactgtga | ggcggtcacc | cagcgccgac | cagagcctcg | aggacagccc | c agcaaggtg | 1500 |
| cccaagagct | ggagcttcgg | ggaccgcagc | cgggcacgcc | aggctttccg | c atcaagggt | 1560 |
| gcggcgtcac | ggcagaactc | agaagcaagc | ctccccggag | aggacattgt | g gatgacaag | 1620 |
| agctgcccct | gcgagtttgt | gaccgaggac | ctgaccccgg | gcctcaaagt | c agcatcaga | 1680 |
| gccgtgtgtg | tcatgcggtt | cctggtgtcc | aagcggaagt | tcaaggagag | c tgcggccc | 1740 |
| tacgacgtga | tggacgtcat | cgagcagtac | tcagccggcc | acctggacat | g ctgtcccga | 1800 |
| attaagagcc | tgcagtccag | agtggaccag | atcgtgggc | gggcccagc | g atcacggac | 1860 |
| aaggaccgca | ccaagggccc | ggccgaggcg | gagctgcccg | aggaccccag | c atgatggga | 1920 |

-continued

```
cggctcggga aggtggagaa gcaggtcttg tccatggaga agaagctgga c ttcctggtg    1980 aatatctaca tgcagcggat gggcatcccc ccgacagaga ccgaggccta c tttggggcc    2040 aaagagccgg agccggcgcc gccgtaccac agcccgaag acagccggga g catgtcgac    2100 aggcacggct gcattgtcaa gatcgtgcgc tccagcagct ccacgggcca g aagaacttc    2160 tcggcgcccc cggccgcgcc ccctgtccag tgtccgccct ccacctcctg g cagccacag    2220 agccacccgc gccagggcca cggcacctcc cccgtggggg accacggctc c ctggtgcgc    2280 atcccgccgc cgcctgccca cgagcggtcg ctgtccgcct acggcggggg c aaccgcgcc    2340 agcatggagt tcctgcggca ggaggacacc ccgggctgca ggccccccga g gggaccctg    2400 cgggacagcg acacgtccat ctccatcccg tccgtggacc acgaggagct g gagcgttcc    2460 ttcagcggct tcagcatctc ccagtccaag gagaacctgg atgctctcaa c agctgctac    2520 gcggccgtgg cgccttgtgc caaagtcagg ccctacattg cggagggaga g tcagacacc    2580 gactccgacc tctgtacccc gtgcgggccc ccgccacgct cggccaccgg c gagggtccc    2640 tttggtgacg tgggctgggc cgggcccagg aagtgaggcg cgctgggcc a gtggacccg    2700 cccgcggccc tcctcagcac ggtgcctccg aggttttgag gcgggaaccc t ttggggccc    2760 ttttcttaca gtaactgagt gtggcggaa gggtgggccc tggagggcc c atgtgggct    2820 gaaggatggg ggctcctggc agtgacccttt tacaaaagtt attttccaac a ggggctgga    2880 gggctgggca gggccctgtg gctccaggag cagcgtgcag agcaaggct g ccctgtcca    2940 ctctgctcag ggccgcggcc gacatcagcc cggtgtgagg aggggcggga g tgatgacgg    3000 ggtgttgcca gcgtggcaac aggcggggg ttgtttcagc cgagcccagg g gaggcacaa    3060 agggcaggcc tgttccctga ggacctgcgc aaagggcggg cctgtttggt g aggacctgc    3120 ggccttgggt cccggtgggg tttccgggca gctacaggcg ggtgtggccg g ccgctgtgc    3180 gtggcctctg ccttcacacc tgacctgccc ggcgggcttt cctgttcccc a cctcagggg    3240 cgcccaaata cagagctatt ggttggcgtc ttaaaaaaaa aaaaaaa              3287
```

<210> SEQ ID NO 20
<211> LENGTH: 871
<212> TYPE: PRT
<213> ORGANISM: Homo sapiens

<400> SEQUENCE: 20

```
Met Val Gln Lys Ser Arg Asn Gly Gly Val Tyr Pro Gly Pro Ser Gly
  1               5                  10                  15

Glu Lys Lys Leu Lys Val Gly Phe Val Gly Leu Asp Pro Gly Ala Pro
             20                  25                  30

Asp Ser Thr Arg Asp Gly Ala Leu Leu Ile Ala Gly Ser Glu Ala Pro
         35                  40                  45

Lys Arg Gly Ser Ile Leu Ser Lys Arg Ala Gly Gly Ala Gly Ala
     50                  55                  60

Gly Lys Pro Pro Lys Arg Asn Ala Phe Tyr Arg Lys Leu Gln Asn Phe
 65                  70                  75                  80

Leu Tyr Asn Val Leu Glu Arg Pro Arg Gly Trp Ala Phe Ile Tyr His
                 85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
```

```
            130             135             140
Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
        355                 360                 365

Val Pro Met Tyr Ser Ser Gln Thr Gln Thr Tyr Gly Ala Ser Arg Leu
    370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
                405                 410                 415

Lys Gly Ser Pro Cys Arg Gly Pro Leu Cys Gly Cys Cys Pro Gly Arg
            420                 425                 430

Ser Ser Gln Lys Val Ser Leu Lys Asp Arg Val Phe Ser Ser Pro Arg
        435                 440                 445

Gly Val Ala Ala Lys Gly Lys Gly Ser Pro Gln Ala Gln Thr Val Arg
    450                 455                 460

Arg Ser Pro Ser Ala Asp Gln Ser Leu Glu Asp Ser Pro Ser Lys Val
465                 470                 475                 480

Pro Lys Ser Trp Ser Phe Gly Asp Arg Ser Arg Ala Arg Gln Ala Phe
                485                 490                 495

Arg Ile Lys Gly Ala Ala Ser Arg Gln Asn Ser Glu Ala Ser Leu Pro
            500                 505                 510

Gly Glu Asp Ile Val Asp Asp Lys Ser Cys Pro Cys Glu Phe Val Thr
        515                 520                 525

Glu Asp Leu Thr Pro Gly Leu Lys Val Ser Ile Arg Ala Val Cys Val
    530                 535                 540

Met Arg Phe Leu Val Ser Lys Arg Lys Phe Lys Glu Ser Leu Arg Pro
545                 550                 555                 560
```

```
Tyr Asp Val Met Asp Val Ile Glu Gln Tyr Ser Ala Gly His Leu Asp
                565                 570                 575

Met Leu Ser Arg Ile Lys Ser Leu Gln Ser Arg Val Asp Gln Ile Val
            580                 585                 590

Gly Arg Gly Pro Ala Ile Thr Asp Lys Asp Arg Thr Lys Gly Pro Ala
        595                 600                 605

Glu Ala Glu Leu Pro Glu Asp Pro Ser Met Met Gly Arg Leu Gly Lys
    610                 615                 620

Val Glu Lys Gln Val Leu Ser Met Glu Lys Lys Leu Asp Phe Leu Val
625                 630                 635                 640

Asn Ile Tyr Met Gln Arg Met Gly Ile Pro Pro Thr Glu Thr Glu Ala
                645                 650                 655

Tyr Phe Gly Ala Lys Glu Pro Glu Pro Ala Pro Pro Tyr His Ser Pro
            660                 665                 670

Glu Asp Ser Arg Glu His Val Asp Arg His Gly Cys Ile Val Lys Ile
        675                 680                 685

Val Arg Ser Ser Ser Thr Gly Gln Lys Asn Phe Ser Ala Pro Pro
    690                 695                 700

Ala Ala Pro Pro Val Gln Cys Pro Ser Thr Ser Trp Gln Pro Gln
705                 710                 715                 720

Ser His Pro Arg Gln Gly His Gly Thr Ser Pro Val Gly Asp His Gly
                725                 730                 735

Ser Leu Val Arg Ile Pro Pro Pro Ala His Glu Arg Ser Leu Ser
            740                 745                 750

Ala Tyr Gly Gly Gly Asn Arg Ala Ser Met Glu Phe Leu Arg Gln Glu
        755                 760                 765

Asp Thr Pro Gly Cys Arg Pro Pro Glu Gly Thr Leu Arg Asp Ser Asp
    770                 775                 780

Thr Ser Ile Ser Ile Pro Ser Val Asp His Glu Glu Leu Glu Arg Ser
785                 790                 795                 800

Phe Ser Gly Phe Ser Ile Ser Gln Ser Lys Glu Asn Leu Asp Ala Leu
                805                 810                 815

Asn Ser Cys Tyr Ala Ala Val Ala Pro Cys Ala Lys Val Arg Pro Tyr
            820                 825                 830

Ile Ala Glu Gly Glu Ser Asp Thr Asp Ser Asp Leu Cys Thr Pro Cys
        835                 840                 845

Gly Pro Pro Pro Arg Ser Ala Thr Gly Glu Gly Pro Phe Gly Asp Val
    850                 855                 860

Gly Trp Ala Gly Pro Arg Lys
865                 870

<210> SEQ ID NO 21
<211> LENGTH: 430
<212> TYPE: PRT
<213> ORGANISM: Homo sapiens

<400> SEQUENCE: 21

Met Ala Ala Ser Ser Pro Pro Arg Ala Glu Arg Lys Arg Trp Gly
 1               5                  10                  15

Trp Gly Arg Leu Pro Gly Ala Arg Arg Gly Ser Ala Gly Leu Ala Lys
            20                  25                  30

Lys Cys Pro Phe Ser Leu Glu Leu Ala Glu Gly Gly Pro Ala Gly Gly
        35                  40                  45

Ala Leu Tyr Ala Pro Ile Ala Pro Gly Ala Pro Gly Pro Ala Pro Pro
```

```
                50              55              60
Ala Ser Pro Ala Ala Pro Ala Ala Pro Val Ala Ser Asp Leu Gly
 65              70              75              80

Pro Arg Pro Val Ser Leu Asp Pro Val Ser Ile Tyr Ser Thr
                 85              90              95

Arg Arg Pro Val Leu Ala Arg Thr His Val Gln Gly Arg Val Tyr Asn
                100             105             110

Phe Leu Glu Arg Pro Thr Gly Trp Lys Cys Phe Val Tyr His Phe Ala
            115             120             125

Val Phe Leu Ile Val Leu Val Cys Leu Ile Phe Ser Val Leu Ser Thr
        130             135             140

Ile Glu Gln Tyr Ala Ala Leu Ala Thr Gly Thr Leu Phe Trp Met Glu
145             150             155             160

Ile Val Leu Val Val Phe Phe Gly Thr Glu Tyr Val Val Arg Leu Trp
                165             170             175

Ser Ala Gly Cys Arg Ser Lys Tyr Val Gly Leu Trp Gly Arg Leu Arg
            180             185             190

Phe Ala Arg Lys Pro Ile Ser Ile Ile Asp Leu Ile Val Val Val Ala
        195             200             205

Ser Met Val Val Leu Cys Val Gly Ser Lys Gly Gln Val Phe Ala Thr
210             215             220

Ser Ala Ile Arg Gly Ile Arg Phe Leu Gln Ile Leu Arg Met Leu His
225             230             235             240

Val Asp Arg Gln Gly Gly Thr Trp Arg Leu Leu Gly Ser Val Val Phe
            245             250             255

Ile His Arg Gln Glu Leu Ile Thr Thr Leu Tyr Ile Gly Phe Leu Gly
        260             265             270

Leu Ile Phe Ser Ser Tyr Phe Val Tyr Leu Ala Glu Lys Asp Ala Val
        275             280             285

Asn Glu Ser Gly Arg Val Glu Phe Gly Ser Tyr Ala Asp Ala Leu Trp
290             295             300

Trp Gly Val Val Thr Val Thr Thr Ile Gly Tyr Gly Asp Lys Val Pro
305             310             315             320

Gln Thr Trp Val Gly Lys Thr Ile Ala Ser Cys Phe Ser Val Phe Ala
            325             330             335

Ile Ser Phe Phe Ala Leu Pro Ala Gly Ile Leu Gly Ser Gly Phe Ala
        340             345             350

Leu Lys Val Gln Gln Lys Gln Arg Gln Lys His Phe Asn Arg Gln Ile
        355             360             365

Pro Ala Ala Ala Ser Leu Ile Gln Thr Ala Trp Arg Cys Tyr Ala Ala
        370             375             380

Glu Asn Pro Asp Ser Ser Thr Trp Lys Ile Tyr Ile Arg Lys Ala Pro
385             390             395             400

Arg Ser His Thr Leu Leu Ser Pro Ser Pro Lys Pro Lys Lys Ser Val
            405             410             415

Val Val Lys Lys Lys Lys Phe Lys Leu Asp Lys Asp Asn Gly
        420             425             430

<210> SEQ ID NO 22
<211> LENGTH: 2169
<212> TYPE: DNA
<213> ORGANISM: mouse

<400> SEQUENCE: 22
```

-continued

```
atggtgcaga agtcgcgcaa cggtggcgtg taccccggca ccagcgggga a aagaagctc    60 aaggtgggct tcgtggggct ggaccccggc gcgcccgact ccacacgcga c ggcgcgcta   120 ctcatcgcgg gctccgaggc ccccaagcgc ggcagcgttt tgagcaagcc g cggacgggc   180 ggcgcgggag ccgggaagcc cccgaagcgc aacgccttct accgcaagct g cagaatttc   240 ctctacaacg tgctagagcg gccccgcggc tgggcgttca tctaccacgc c tacgtgttc   300 cttttagtct tctcctgcct tgtgctttct gtgttttcca ccatcaagga g tacgagaag   360 agctctgagg gggccctcta catcttggaa atcgtgacta tcgtggtatt c ggtgttgag   420 tactttgtga ggatctgggc tgcaggctgc tgttgccggt atcgaggctg g aggggcagg   480 ctcaagtttg ccaggaagcc gttctgtgtg attgatatca tggtgctgat t gcctccatt   540 gctgtgctgg ctgctggttc ccagggcaat gtctttgcca catctgcgct t cggagcttg   600 cggttcttgc aaatcttgcg gatgatccgt atggaccgga gggtggcac c tggaagctc   660 ttgggatcgg tagtctacgc tcacagcaag gagctggtga ctgcctggta c attggcttc   720 ctctgcctca tcctgcctc atttctggtg tacttggcag aaaagggtga g aatgaccac   780 tttgacacct acgcagatgc actctggtgg ggtctgatca ccctgacgac c attggctac   840 ggggacaagt accctcagac ctggaacggg aggctgctgg cagcgacctt t accctcatt   900 ggtgtctcgt tctttgctct tcctgctggc attttgggat ccggctttgc c ctgaaagtc   960 caagagcagc atcggcaaaa acactttgag aaacggcgga accctgcgg a ggtctgatc  1020 cagtctgcct ggagattcta tgctactaac ctctcacgca ccgacctgca c tccacgtgg  1080 cagtactacg agcggacagt cactgtcccc atgtacagac tcatcccacc t ctgaaccag  1140 ctggagctgc tgaggaatct caagagcaaa tctggactca ccttcaggaa g gagccacag  1200 ccagagccat caccaagtca gaaggtcagt ttgaaagatc gtgtcttctc c agccccga   1260 ggcatggctg ccaagggaaa ggggtctccc caggcccaga cggtccggcg g tcccccagt  1320 gcggatcaga gtcttgatga cagcccgagc aaggtgccca gagctggag c tttggtgac  1380 cgcagccgca cacgccaggc tttccgcatc aagggtgctg catcccggca g aattcagaa  1440 gcaagcctcc ctgggagga catcgtagag acaacaaga gctgtaactg c gagtttgtg  1500 actgaagatc ttaccctgg cctcaaagtt agcatcagag ctgtgtgtgt t atgcggttc  1560 ttggtatcta agcgaaagtt caaagagagt ctgcgcccat atgatgtgat g gacgtcatc  1620 gaacagtact cggctggaca cttggatatg ttgtcccgca tcaagagcct g cagtccaga  1680 gtggaccaga ttgtggggcg gggcccaaca ataacggata aggatcgcac c aaaggccca  1740 gcggaaacgg agctgcccga agaccccagc atgatgggac ggcttgggaa g gtggagaaa  1800 caggtcttgt ccatggaaaa gaagctcgac ttcttggtga gcatctatac a cagagaatg  1860 ggcatcccac cagcagagac agaggcctat tttggggcca aggagcctga g ccggcacca  1920 ccctaccaca gcccagagga cagccgtgac catgcagaca agcatggctg t atcattaag  1980 atcgtccgct ccaccagctc tacgggccag aggaactacg cagcacccc a gccatcccc  2040 cctgcccagt gtcctccctc cacctcgtgg cagcagagcc accagcgcca t gcacctcc  2100 cctgtgggag accatggctc actggtcctg cgactggaga ggagtgctgg c atgatgagc  2160 tgtcactag                                                    2169
```

<210> SEQ ID NO 23
<211> LENGTH: 722
<212> TYPE: PRT
<213> ORGANISM: mouse

-continued

<400> SEQUENCE: 23

```
Met Val Gln Lys Ser Arg Asn Gly Gly Val Tyr Pro Gly Thr Ser Gly
 1               5                  10                  15
Glu Lys Lys Leu Lys Val Gly Phe Val Gly Leu Asp Pro Gly Ala Pro
                20                  25                  30
Asp Ser Thr Arg Asp Gly Ala Leu Leu Ile Ala Gly Ser Glu Ala Pro
            35                  40                  45
Lys Arg Gly Ser Val Leu Ser Lys Pro Arg Thr Gly Gly Ala Gly Ala
        50                  55                  60
Gly Lys Pro Pro Lys Arg Asn Ala Phe Tyr Arg Lys Leu Gln Asn Phe
 65                  70                  75                  80
Leu Tyr Asn Val Leu Glu Arg Pro Arg Gly Trp Ala Phe Ile Tyr His
                85                  90                  95
Ala Tyr Val Phe Leu Leu Val Phe Ser Cys Leu Val Leu Ser Val Phe
                100                 105                 110
Ser Thr Ile Lys Glu Tyr Glu Lys Ser Ser Glu Gly Ala Leu Tyr Ile
            115                 120                 125
Leu Glu Ile Val Thr Ile Val Val Phe Gly Val Glu Tyr Phe Val Arg
        130                 135                 140
Ile Trp Ala Ala Gly Cys Cys Cys Arg Tyr Arg Gly Trp Arg Gly Arg
145                 150                 155                 160
Leu Lys Phe Ala Arg Lys Pro Phe Cys Val Ile Asp Ile Met Val Leu
                165                 170                 175
Ile Ala Ser Ile Ala Val Leu Ala Ala Gly Ser Gln Gly Asn Val Phe
            180                 185                 190
Ala Thr Ser Ala Leu Arg Ser Leu Arg Phe Leu Gln Ile Leu Arg Met
        195                 200                 205
Ile Arg Met Asp Arg Arg Gly Gly Thr Trp Lys Leu Leu Gly Ser Val
210                 215                 220
Val Tyr Ala His Ser Lys Glu Leu Val Thr Ala Trp Tyr Ile Gly Phe
225                 230                 235                 240
Leu Cys Leu Ile Leu Ala Ser Phe Leu Val Tyr Leu Ala Glu Lys Gly
                245                 250                 255
Glu Asn Asp His Phe Asp Thr Tyr Ala Asp Ala Leu Trp Trp Gly Leu
            260                 265                 270
Ile Thr Leu Thr Thr Ile Gly Tyr Gly Asp Lys Tyr Pro Gln Thr Trp
        275                 280                 285
Asn Gly Arg Leu Leu Ala Ala Thr Phe Thr Leu Ile Gly Val Ser Phe
290                 295                 300
Phe Ala Leu Pro Ala Gly Ile Leu Gly Ser Gly Phe Ala Leu Lys Val
305                 310                 315                 320
Gln Glu Gln His Arg Gln Lys His Phe Glu Lys Arg Arg Asn Pro Ala
                325                 330                 335
Ala Gly Leu Ile Gln Ser Ala Trp Arg Phe Tyr Ala Thr Asn Leu Ser
            340                 345                 350
Arg Thr Asp Leu His Ser Thr Trp Gln Tyr Tyr Glu Arg Thr Val Thr
        355                 360                 365
Val Pro Met Tyr Arg Leu Ile Pro Pro Leu Asn Gln Leu Glu Leu Leu
    370                 375                 380
Arg Asn Leu Lys Ser Lys Ser Gly Leu Thr Phe Arg Lys Glu Pro Gln
385                 390                 395                 400
Pro Glu Pro Ser Pro Ser Gln Lys Val Ser Leu Lys Asp Arg Val Phe
```

```
                    405                 410                 415
Ser Ser Pro Arg Gly Met Ala Ala Lys Gly Lys Gly Ser Pro Gln Ala
                420                 425                 430
Gln Thr Val Arg Arg Ser Pro Ser Ala Asp Gln Ser Leu Asp Asp Ser
                435                 440                 445
Pro Ser Lys Val Pro Lys Ser Trp Ser Phe Gly Asp Arg Ser Arg Thr
                450                 455                 460
Arg Gln Ala Phe Arg Ile Lys Gly Ala Ala Ser Arg Gln Asn Ser Glu
465                 470                 475                 480
Ala Ser Leu Pro Gly Glu Asp Ile Val Glu Asp Asn Lys Ser Cys Asn
                485                 490                 495
Cys Glu Phe Val Thr Glu Asp Leu Thr Pro Gly Leu Lys Val Ser Ile
                500                 505                 510
Arg Ala Val Cys Val Met Arg Phe Leu Val Ser Lys Arg Lys Phe Lys
                515                 520                 525
Glu Ser Leu Arg Pro Tyr Asp Val Met Asp Val Ile Glu Gln Tyr Ser
                530                 535                 540
Ala Gly His Leu Asp Met Leu Ser Arg Ile Lys Ser Leu Gln Ser Arg
545                 550                 555                 560
Val Asp Gln Ile Val Gly Arg Gly Pro Thr Ile Thr Asp Lys Asp Arg
                565                 570                 575
Thr Lys Gly Pro Ala Glu Thr Glu Leu Pro Glu Asp Pro Ser Met Met
                580                 585                 590
Gly Arg Leu Gly Lys Val Glu Lys Gln Val Leu Ser Met Glu Lys Lys
                595                 600                 605
Leu Asp Phe Leu Val Ser Ile Tyr Thr Gln Arg Met Gly Ile Pro Pro
                610                 615                 620
Ala Glu Thr Glu Ala Tyr Phe Gly Ala Lys Glu Pro Glu Pro Ala Pro
625                 630                 635                 640
Pro Tyr His Ser Pro Glu Asp Ser Arg Asp His Ala Asp Lys His Gly
                645                 650                 655
Cys Ile Ile Lys Ile Val Arg Ser Thr Ser Thr Gly Gln Arg Asn
                660                 665                 670
Tyr Ala Ala Pro Pro Ala Ile Pro Pro Ala Gln Cys Pro Pro Ser Thr
                675                 680                 685
Ser Trp Gln Gln Ser His Gln Arg His Gly Thr Ser Pro Val Gly Asp
                690                 695                 700
His Gly Ser Leu Val Leu Arg Leu Glu Arg Ser Ala Gly Met Met Ser
705                 710                 715                 720
Cys His

<210> SEQ ID NO 24
<211> LENGTH: 605
<212> TYPE: PRT
<213> ORGANISM: mouse

<400> SEQUENCE: 24

Met Ser Thr Pro Val Ser Pro Ala Pro Ala Pro Ala Asp Leu Gly Pro
1               5                   10                  15
Arg Pro Arg Val Ser Leu Asp Pro Arg Val Ser Ile Tyr Ser Ala Arg
                20                  25                  30
Arg Pro Leu Leu Ala Arg Thr His Ile Gln Gly Arg Val Tyr Asn Phe
                35                  40                  45
Leu Glu Arg Pro Thr Gly Trp Lys Cys Phe Val Tyr His Phe Thr Val
```

```
            50                  55                  60
Phe Leu Ile Val Leu Val Cys Leu Ile Phe S er Val Leu Ser Thr Ile
 65                  70                  75                  80
Glu Gln Tyr Ala Ala Leu Ala Thr Gly Thr L eu Phe Trp Met Glu Ile
                 85                  90                  95
Val Leu Val Val Phe Phe Gly Thr Glu Tyr V al Val Arg Leu Trp Ser
                100                 105                 110
Ala Gly Cys Arg Ser Lys Tyr Val Gly Ile T rp Gly Arg Leu Arg Phe
                115                 120                 125
Ala Arg Lys Pro Ile Ser Ile Ile Asp Leu I le Val Val Ala Ser
130                 135                 140
Met Val Val Leu Cys Val Gly Ser Lys Gly G ln Val Phe Ala Thr Ser
145                 150                 155                 160
Ala Ile Arg Gly Ile Arg Phe Leu Gln Ile L eu Arg Met Leu His Val
                165                 170                 175
Asp Arg Gln Gly Gly Thr Trp Arg Leu Leu G ly Ser Val Val Phe Ile
                180                 185                 190
His Arg Gln Glu Leu Ile Thr Thr Leu Tyr I le Gly Phe Leu Gly Leu
                195                 200                 205
Ile Phe Ser Ser Tyr Phe Val Tyr Leu Ala G lu Lys Asp Ala Val Asn
210                 215                 220
Glu Ser Gly Arg Ile Glu Phe Gly Ser Tyr A la Asp Ala Leu Trp Trp
225                 230                 235                 240
Gly Val Val Thr Val Thr Thr Ile Gly Tyr G ly Asp Lys Val Pro Gln
                245                 250                 255
Thr Trp Val Gly Lys Thr Ile Ala Ser Cys P he Ser Val Phe Ala Ile
                260                 265                 270
Ser Phe Phe Ala Leu Pro Ala Gly Ile Leu G ly Ser Gly Phe Ala Leu
                275                 280                 285
Lys Val Gln Gln Lys Gln Arg Gln Lys His P he Asn Arg Gln Ile Pro
                290                 295                 300
Ala Ala Ala Ser Leu Ile Gln Thr Ala Trp A rg Cys Tyr Ala Ala Glu
305                 310                 315                 320
Asn Pro Asp Ser Ala Thr Trp Lys Ile Tyr V al Arg Lys Pro Ala Arg
                325                 330                 335
Ser His Thr Leu Leu Ser Pro Ser Pro Lys P ro Lys Lys Ser Val Met
                340                 345                 350
Val Lys Lys Lys Lys Phe Lys Leu Asp Lys A sp Asn Gly Met Ser Pro
                355                 360                 365
Gly Glu Lys Met Phe Asn Val Pro His Ile T hr Tyr Asp Pro Pro Glu
                370                 375                 380
Asp Arg Arg Pro Asp His Phe Ser Ile Asp G ly Tyr Asp Ser Ser Val
385                 390                 395                 400
Arg Lys Ser Pro Thr Leu Leu Glu Leu Ser T hr Pro His Phe Leu Arg
                405                 410                 415
Thr Asn Ser Phe Ala Glu Asp Leu Asp Leu G lu Gly Glu Thr Leu Leu
                420                 425                 430
Thr Pro Ile Thr His Val Ser Gln Leu Arg A sp His His Arg Ala Thr
                435                 440                 445
Ile Lys Val Ile Arg Arg Met Gln Tyr Phe V al Ala Lys Lys Lys Phe
                450                 455                 460
Gln Gln Ala Arg Lys Pro Tyr Asp Val Arg A sp Val Ile Glu Gln Tyr
465                 470                 475                 480
```

```
Ser Gln Gly His Leu Asn Leu Met Val Arg Ile Lys Glu Leu Gln Arg
                485                 490                 495

Arg Leu Asp Gln Ser Ile Gly Lys Pro Ser Leu Phe Ile Pro Ile Ser
            500                 505                 510

Glu Lys Ser Lys Asp Arg Gly Ser Asn Thr Ile Gly Ala Arg Leu Asn
        515                 520                 525

Arg Val Glu Asp Lys Val Thr Gln Leu Asp Gln Arg Leu Val Ile Ile
    530                 535                 540

Thr Asp Met Leu His Gln Leu Leu Ser Met Gln Gln Gly Gly Pro Thr
545                 550                 555                 560

Cys Asn Ser Arg Ser Gln Val Val Ala Ser Asn Glu Gly Gly Ser Ile
                565                 570                 575

Asn Pro Glu Leu Phe Leu Pro Ser Asn Ser Leu Pro Thr Tyr Glu Gln
            580                 585                 590

Leu Thr Val Pro Gln Thr Gly Pro Asp Glu Gly Ser Ser
        595                 600                 605

<210> SEQ ID NO 25
<211> LENGTH: 10
<212> TYPE: PRT
<213> ORGANISM: Artificial Sequence
<220> FEATURE:
<223> OTHER INFORMATION: Description of Artificial  Sequence:Signature
      sequence for a potassium channel
<223> OTHER INFORMATION: Xaa is any amino ac id

<400> SEQUENCE: 25

Arg Xaa Xaa Gln Xaa Xaa Arg Xaa Xaa Arg
  1               5                  10

<210> SEQ ID NO 26
<211> LENGTH: 2565
<212> TYPE: DNA
<213> ORGANISM: Homo sapiens

<400> SEQUENCE: 26
atggcattgg agttcccggc ggctaaccca gccggagggg acgcggcggc g gccggcgac      60 gaggagcgga aagtgggggct ggcgcccggc gacgtggagc aagtcaccttt g gcgctcggg    120 gccggagccg acaaagacgg gaccctgctg ctggagggcg gcggccgcga c gaggggcag     180 cggaggaccc gcagggcat cgggctcctg ccaagaccc gctgagccg c ccagtcaag       240 agaaacaacg ccaagtaccg gcgcatccaa actttgatct acgacgccct g gagagaccg   300 cggggctggg cgctgcttta ccacgcgttg gtgttcctga ttgtcctggg g tgcttgatt    360 ctggctgtcc tgaccacatt caaggagtat gagactgtct cgggagactg g cttctgtta  420 ctggagacat ttgctatttt catctttgga gccgagtttg ctttgaggat c tgggctgct    480 ggatgttgct gccgatacaa aggctggcgg ggccgactga agtttgccag g aagcccctg   540 tgcatgttgg acatctttgt gctgattgcc tctgtgccag tggttgctgt g ggaaaccaa   600 ggcaatgttc tggccacctc cctgcgaagc ctgcgcttcc tgcagatcct g cgcatgctg   660 cggatggacc ggagaggtgg cacctggaag cttctgggct cagccatctg t gcccacagc   720 aaagaactca tcacggcctg gtacatcggt ttcctgacac tcatccttttc t tcatttctt   780 gtctacctgg ttgagaaaga cgtcccagag gtggatgcac aaggagagga g atgaaagag   840 gagtttgaga cctatgcaga tgccctgtgg tgggcctga tcacactggc c accattggc    900 tatggagaca gacacccaa aacgtgggaa ggccgtctga ttgccgccac c ttttcctta    960
```

-continued

```
attggcgtct cctttttgc ccttccagcg ggcatcctgg ggtccgggct g gccctcaag      1020 gtgcaggagc aacaccgtca gaagcacttt gagaaaagga ggaagccagc t gctgagctc      1080 attcaggctg cctggaggta ttatgctacc aaccccaaca ggattgacct g gtggcgaca      1140 tggagatttt atgaatcagt cgtctctttt cctttcttca ggaaagaaca g ctggaggca      1200 gcatccagcc aaaagctggg tctcttggat cgggttcgcc tttctaatcc t cgtggtagc      1260 aatactaaag gaaagctatt taccccctctg aatgtagatg ccatagaaga a agtccttct      1320 aaagaaccaa agcctgttgg cttaaacaat aaagagcgtt ccgcacggc c ttccgcatg       1380 aaagcctacg ctttctggca gagttctgaa gatgccggga caggtgaccc c atggcggaa      1440 gacaggggct atgggaatga cttccccatc aagacatga tccccaccct g aaggccgcc      1500 atccgagccg tcagaattct acaattccgt ctctataaaa aaaattcaa g gagactttg      1560 aggccttacg atgtgaagga tgtgattgag cagtattctg ccgggcatct c gacatgctt      1620 tccaggataa agtaccttca gacgagaata gatatgattt cacccctgg a cctccctcc      1680 acgccaaaac acaagaagtc tcagaaaggg tcagcattca ccttcccatc c cagcaatct      1740 cccaggaatg aaccatatgt agccagacca tccacatcag aaatcgaaga c caaagcatg      1800 atggggaagt tgtaaaaagt tgaaagacag gttcaggaca tggggaagaa g ctggacttc      1860 ctcgtggata tgcacatgca acacatggaa cggttgcagg tgcaggtcac g gagtattac      1920 ccaaccaagg caccctcctc gccagctgaa gcagagaaga aggaggacaa c aggtattcc      1980 gatttgaaaa ccatcatctg caactattct gagacaggcc ccccggaacc a ccctacagc      2040 ttccaccagg tgaccattga caaagtcagc ccctatgggt tttttgcaca t gaccctgtg      2100 aacctgcccc gagggggacc cagttctgga aaggttcagg caactcctcc t cctcagca       2160 acaacgtatg tggagaggcc cacggtcctg cctatcttga ctcttctcga c tcccgagtg     2220 agctgccact cccaggctga cctgcaggc ccctactcgg accgaatctc c ccccggcag      2280 agacgtagca tcacgcgaga cagtgacaca cctctgtccc tgatgtcggt c aaccacgag     2340 gagctggaga ggtctccaag tggcttcagc atctcccagg acagagatga t tatgtgttc     2400 ggccccaatg gggggtcgag ctggatgagg gagaagcggt acctcgccga g ggtgagacg     2460 gacacagaca cggacccctt cacgcccagc ggctccatgc ctctgtcgtc c acagggat     2520 gggatttctg attcagtatg gacccttcc aataagccca tttaa               2565
```

<210> SEQ ID NO 27
<211> LENGTH: 854
<212> TYPE: PRT
<213> ORGANISM: Homo sapiens

<400> SEQUENCE: 27

```
Met Ala Leu Glu Phe Pro Ala Ala Asn Pro A la Gly Gly Asp Ala Ala
  1               5                  10                  15

Ala Ala Gly Asp Glu Glu Arg Lys Val Gly L eu Ala Pro Gly Asp Val
                 20                  25                  30

Glu Gln Val Thr Leu Ala Leu Gly Ala Gly A la Asp Lys Asp Gly Thr
             35                  40                  45

Leu Leu Leu Glu Gly Gly Gly Arg Asp Glu G ly Gln Arg Arg Thr Pro
         50                  55                  60

Gln Gly Ile Gly Leu Leu Ala Lys Thr Pro L eu Ser Arg Pro Val Lys
     65                  70                  75                  80

Arg Asn Asn Ala Lys Tyr Arg Arg Ile Gln T hr Leu Ile Tyr Asp Ala
```

```
                    85                  90                  95
Leu Glu Arg Pro Arg Gly Trp Ala Leu Leu Tyr His Ala Leu Val Phe
                100                 105                 110
Leu Ile Val Leu Gly Cys Leu Ile Leu Ala Val Leu Thr Thr Phe Lys
                115                 120                 125
Glu Tyr Glu Thr Val Ser Gly Asp Trp Leu Leu Leu Glu Thr Phe
                130                 135             140
Ala Ile Phe Ile Phe Gly Ala Glu Phe Ala Leu Arg Ile Trp Ala Ala
145                 150                 155                 160
Gly Cys Cys Cys Arg Tyr Lys Gly Trp Arg Gly Arg Leu Lys Phe Ala
                165                 170                 175
Arg Lys Pro Leu Cys Met Leu Asp Ile Phe Val Leu Ile Ala Ser Val
                180                 185                 190
Pro Val Val Ala Val Gly Asn Gln Gly Asn Val Leu Ala Thr Ser Leu
                195                 200                 205
Arg Ser Leu Arg Phe Leu Gln Ile Leu Arg Met Leu Arg Met Asp Arg
                210                 215                 220
Arg Gly Gly Thr Trp Lys Leu Leu Gly Ser Ala Ile Cys Ala His Ser
225                 230                 235                 240
Lys Glu Leu Ile Thr Ala Trp Tyr Ile Gly Phe Leu Thr Leu Ile Leu
                245                 250                 255
Ser Ser Phe Leu Val Tyr Leu Val Glu Lys Asp Val Pro Glu Val Asp
                260                 265                 270
Ala Gln Gly Glu Glu Met Lys Glu Glu Phe Glu Thr Tyr Ala Asp Ala
                275                 280                 285
Leu Trp Trp Gly Leu Ile Thr Leu Ala Thr Ile Gly Tyr Gly Asp Lys
                290                 295                 300
Thr Pro Lys Thr Trp Glu Gly Arg Leu Ile Ala Ala Thr Phe Ser Leu
305                 310                 315                 320
Ile Gly Val Ser Phe Phe Ala Leu Pro Ala Gly Ile Leu Gly Ser Gly
                325                 330                 335
Leu Ala Leu Lys Val Gln Glu Gln His Arg Gln Lys His Phe Glu Lys
                340                 345                 350
Arg Arg Lys Pro Ala Ala Glu Leu Ile Gln Ala Ala Trp Arg Tyr Tyr
                355                 360                 365
Ala Thr Asn Pro Asn Arg Ile Asp Leu Val Ala Thr Trp Arg Phe Tyr
                370                 375                 380
Glu Ser Val Val Ser Phe Pro Phe Arg Lys Glu Gln Leu Glu Ala
385                 390                 395                 400
Ala Ser Ser Gln Lys Leu Gly Leu Leu Asp Arg Val Arg Leu Ser Asn
                405                 410                 415
Pro Arg Gly Ser Asn Thr Lys Gly Lys Leu Phe Thr Pro Leu Asn Val
                420                 425                 430
Asp Ala Ile Glu Glu Ser Pro Ser Lys Glu Pro Lys Pro Val Gly Leu
                435                 440                 445
Asn Asn Lys Glu Arg Phe Arg Thr Ala Phe Arg Met Lys Ala Tyr Ala
                450                 455                 460
Phe Trp Gln Ser Ser Glu Asp Ala Gly Thr Gly Asp Pro Met Ala Glu
465                 470                 475                 480
Asp Arg Gly Tyr Gly Asn Asp Phe Pro Ile Glu Asp Met Ile Pro Thr
                485                 490                 495
Leu Lys Ala Ala Ile Arg Ala Val Arg Ile Leu Gln Phe Arg Leu Tyr
                500                 505                 510
```

```
Lys Lys Lys Phe Lys Glu Thr Leu Arg Pro Tyr Asp Val Lys Asp Val
            515                 520                 525
Ile Glu Gln Tyr Ser Ala Gly His Leu Asp Met Leu Ser Arg Ile Lys
    530                 535                 540
Tyr Leu Gln Thr Arg Ile Asp Met Ile Phe Thr Pro Gly Pro Pro Ser
545                 550                 555                 560
Thr Pro Lys His Lys Ser Gln Lys Gly Ser Ala Phe Thr Phe Pro
                565                 570                 575
Ser Gln Gln Ser Pro Arg Asn Glu Pro Tyr Val Ala Arg Pro Ser Thr
            580                 585                 590
Ser Glu Ile Glu Asp Gln Ser Met Met Gly Lys Phe Val Lys Val Glu
            595                 600                 605
Arg Gln Val Gln Asp Met Gly Lys Lys Leu Asp Phe Leu Val Asp Met
    610                 615                 620
His Met Gln His Met Glu Arg Leu Gln Val Gln Val Thr Glu Tyr Tyr
625                 630                 635                 640
Pro Thr Lys Gly Thr Ser Ser Pro Ala Glu Ala Glu Lys Lys Glu Asp
                645                 650                 655
Asn Arg Tyr Ser Asp Leu Lys Thr Ile Ile Cys Asn Tyr Ser Glu Thr
            660                 665                 670
Gly Pro Pro Glu Pro Pro Tyr Ser Phe His Gln Val Thr Ile Asp Lys
        675                 680                 685
Val Ser Pro Tyr Gly Phe Phe Ala His Asp Pro Val Asn Leu Pro Arg
    690                 695                 700
Gly Gly Pro Ser Ser Gly Lys Val Gln Ala Thr Pro Pro Ser Ser Ala
705                 710                 715                 720
Thr Thr Tyr Val Glu Arg Pro Thr Val Leu Pro Ile Leu Thr Leu Leu
                725                 730                 735
Asp Ser Arg Val Ser Cys His Ser Gln Ala Asp Leu Gln Gly Pro Tyr
            740                 745                 750
Ser Asp Arg Ile Ser Pro Arg Gln Arg Ser Ile Thr Arg Asp Ser
    755                 760                 765
Asp Thr Pro Leu Ser Leu Met Ser Val Asn His Glu Glu Leu Glu Arg
    770                 775                 780
Ser Pro Ser Gly Phe Ser Ile Ser Gln Asp Arg Asp Asp Tyr Val Phe
785                 790                 795                 800
Gly Pro Asn Gly Gly Ser Ser Trp Met Arg Glu Lys Arg Tyr Leu Ala
                805                 810                 815
Glu Gly Glu Thr Asp Thr Asp Thr Asp Pro Phe Thr Pro Ser Gly Ser
            820                 825                 830
Met Pro Leu Ser Ser Thr Gly Asp Gly Ile Ser Asp Ser Val Trp Thr
            835                 840                 845
Pro Ser Asn Lys Pro Ile
        850

<210> SEQ ID NO 28
<211> LENGTH: 120
<212> TYPE: PRT
<213> ORGANISM: mouse

<400> SEQUENCE: 28

Asp Leu His Ser Thr Trp Gln Tyr Tyr Glu Arg Thr Val Thr Val Pro
  1               5                  10                  15

Met Tyr Arg Leu Ile Pro Pro Leu Asn Gln Leu Glu Leu Leu Arg Asn
```

-continued

```
                20                     25                      30
Leu Lys Ser Lys Ser Gly Leu Thr Phe Arg Lys Glu Pro Gln Pro Glu
            35                      40                  45
Pro Ser Pro Ser Gln Lys Val Ser Leu Lys Asp Arg Val Phe Ser Ser
        50                      55                  60
Pro Arg Gly Met Ala Ala Lys Gly Lys Gly Ser Pro Gln Ala Gln Thr
 65                     70                  75                  80
Val Arg Arg Ser Pro Ser Ala Asp Gln Ser Leu Asp Asp Ser Pro Ser
                85                      90                  95
Lys Val Pro Lys Ser Trp Ser Phe Gly Asp Arg Ser Arg Thr Arg Gln
            100                     105                 110
Ala Phe Arg Ile Lys Gly Ala Ala
            115                 120
```